(12) United States Patent
Jensen et al.

(10) Patent No.: US 6,589,775 B1
(45) Date of Patent: Jul. 8, 2003

(54) DNA SEQUENCE ENCODING ENZYMES OF CLAVULANIC ACID BIOSYNTHESIS

(75) Inventors: Susan E. Jensen, Edmonton (CA); Kwamena A. Aidoo, Timberlea (CA); Ashish S. Paradkar, Edmonton (CA)

(73) Assignee: The Governors of the University of Alberta, Edmonton (CA)

( * ) Notice: Subject to any disclaimer, the term of this patent is extended or adjusted under 35 U.S.C. 154(b) by 0 days.

(21) Appl. No.: 09/385,040

(22) Filed: Aug. 30, 1999

Related U.S. Application Data

(63) Continuation-in-part of application No. 08/790,462, filed on Jan. 29, 1997, now abandoned, which is a continuation-in-part of application No. 08/567,801, filed on Dec. 6, 1995, now abandoned, which is a continuation of application No. 08/134,018, filed on Oct. 8, 1993, now abandoned.

(51) Int. Cl.$^7$ .................................................. C12N 1/20
(52) U.S. Cl. .............................. 435/252.35; 435/252.3; 435/320.1; 435/325; 435/410; 536/23.2
(58) Field of Search ...................... 435/252.35, 320.1, 435/252.3, 325, 410; 536/23.2

(56) References Cited

FOREIGN PATENT DOCUMENTS

EP     0 349 121     1/1990

OTHER PUBLICATIONS

Paradkar, A.S. et al, "Functional Analysis of the Gene Encoding the Clavaminate Synthase 2 Isoenzyme Involved in Clavulanic Acid Biosynthesis in *Streptomyces clavuligerus*", Journal of Bacteriology, vol. 177, No. 5, Mar. 1995, pp. 1307–1314.

Aidoo, K.A., et al., "Cloning, sequencing and disruption of a gene from *Streptomyces clavuligerus* involved in clavulanic acid biosynthesis", Gene, vol. 147, 1994, pp. 41–46.

Marsh, E.N. et al, "Two Isozymes of Clavaminate Synthase Central to Clavlulanic Acid Formation: Cloning and Sequencing Of Both Genes from *Streptomyces clavuligerus*", Biochemistry, vol. 31, 1992, pp. 12648–12657.

Ward, J.M. et al, "The biosynthetic genes for clavulanic acid and cephamycin production occur as a 'super–cluster' in three Streptomyces", FEMS Microbiology Letters 110, 1993, pp. 239–242.

*Primary Examiner*—Elizabeth Slobodyansky
(74) *Attorney, Agent, or Firm*—Jacobson Holman PLLC

(57) ABSTRACT

DNA sequences are provided which encode the enzymes required for clavulanic acid synthesis. A process is provided for producing clavulanic acid in a transformant of a non-clavulanate-producing host.

29 Claims, 28 Drawing Sheets

FIG. 1

| | Met | Glu | Arg | Ile | Asp | Ser | His | Val | Ser | Pro | Arg | |
|---|---|---|---|---|---|---|---|---|---|---|---|---|
| N-terminal amino acid sequence of CLA | Tyr | Ala | Gln | Ile | Pro | Thr | Phe | Met | Arg | (Leu) | Pro | His | Asp | (Asp) |
| Potential codons (DNA) | TAT | GCT | CAA | ATT | CCT | ACT | TTT | ATG | | | | |
| | C | C | G | C | C | C | C | | | | | |
| | | A | | A | A | A | | | | | | |
| | | G | | | G | G | | | | | | |
| Probe made = 24-mer oligonucleotide with 8-fold degeneracy | TAC | GCC | CAG | ATC | CCC | ACC | TTC | ATG | | | | |
| | | G | | | G | G | | | | | | |
| Actual DNA sequence | TAC | GCA | CAG | ATC | CCC | ACC | TTC | ATG | | | | |

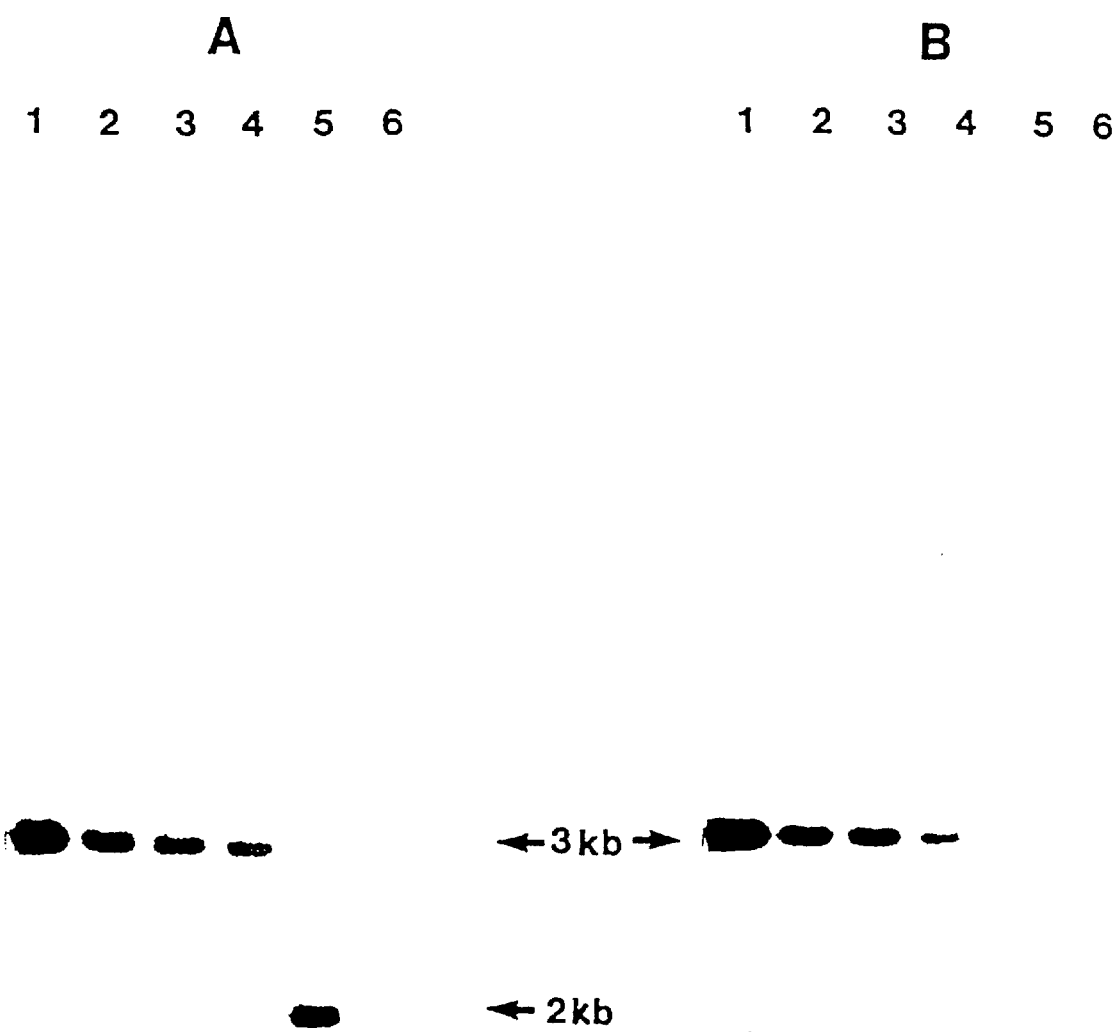

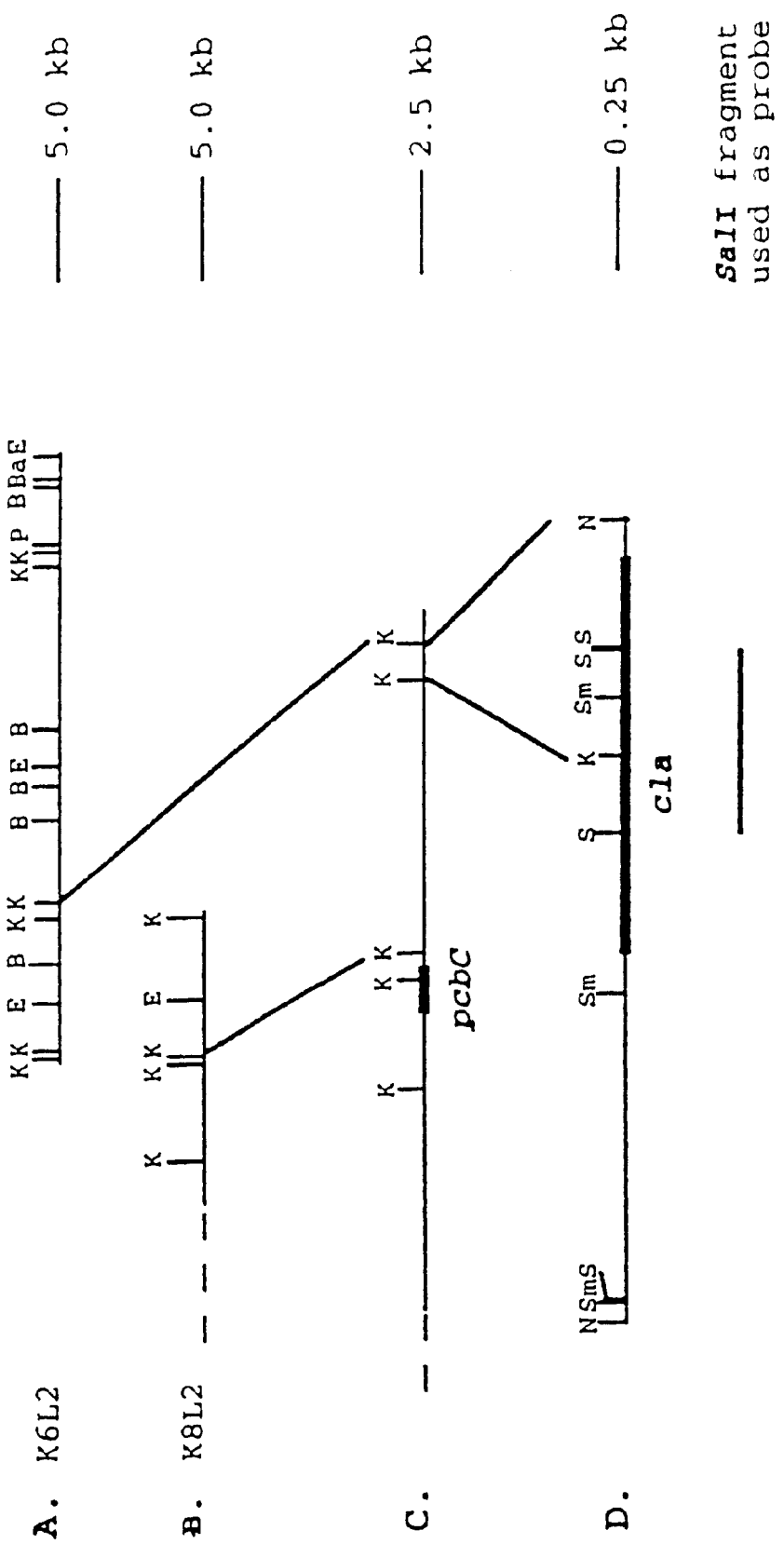

FIG. 8

```
            10         20         30         40         50         60
  1  MTHSDNYGDD PPQGRRRSRG RAATAVVAGL AVTVGLGYWG YTSLVADEKD SGDPEVEAAA   60
 61  GQFDTFLGAW EKGDAPTAAG LTDTPNAES AKVGGKEW LIKSVMTNLK PTKTEITAKT GEKNPEGEVE  120
121  IPFTVRMTLP GAGEYAWDST AKVGGKEW KVAFNTEMIH PQMVPGQTLA LKSRERADIL  180
181  DANGNVLQAA SIIGAVDPRT GKGSAGLQSR YDKQLTGGSG AARSVVILDR ESGQVVKKLT  240
241  GLKDTEGKPV KTTIDPRVQS AAAALEGSK KNAAIVAVDP ATGNILAAAN VPSGMNRALE  300
301  GRYPPGSTFK VVTTAALLQQ GMNPEERADC PKFAHVNGQS FENQDQFTLP AGSTFRDSFA  360
361  HSCNTFFVNS RSKLSESSLK QAAEAFGIGG TWDVGASTFD GSVPVSNSEN DKAASTIGQA  420
421  RVEASPLVMA SIAATVKQGE FKQPVLVPDA VKKPHQAPRM APGIVDSLRS MMRSTVTDGA  480
481  GDALRGLGGQ PHAKTGTAEF GTEKPPKTHA WMIGYQGDRN IAWSVLLEDG GSGGADAGPV  540
541  AAKFLSNLAA GZ                                                      552
            10         20         30         40         50         60
```

FIG. 9

```
              10         20         30         40         50         60
              |          |          |          |          |          |
  1  MSRVSTAPSG KPTAAHALLS RLRDHGVGKV FGVVGREAAS ILFDEVEGID FVLTRHEFTA   60
 61  GVAADVLARI TGRPQACWAT LGPGMINLST GIATSVLDRS PVIALAAQSE SHDIFPNDTH  120
121  QCLDSVAIVA PMSKYAVELQ RPHEITDLVD SAVNAAMTEP VGPSFISLPV DLLGSSEGID  180
181  TTVPNPPANT PAKPVGVVAD GWQKAADQAA ALLAEAKHPV LVVGAAAIRS GAVPAIRALA  240
241  ERLNIPVITT YIAKGVLPVG HELNYGAVTG YMDGILNFPA LQIMFAPVDL VLTVGYDYAE  300
301  DLRPSMWQKG IEKKTVRISP TVNPIPRVYR PDVDVVTDVL AFVEHFETAT ASFGAKQRHD  360
361  IEPLRARIAE FLADPETYED GMRVHQVIDS MNTVMEEAAE PGEGTIVSDI GFFRHYGVLF  420
421  ARADQPFGFL TSAGCSSFGY GIPAAIGAQM ARPDQPIFLI AGDGGFHSNS SDLETIARLN  480
481  LPIVTVVVNN DINGLIELYQ NIGHHRSHDP AVKFGGVDFV ALAEANGVDA TRAINREELL  540
541  AALRKGAELG RPFLIEVPVN YDFQPGGFGA LSIZ                              574
              |          |          |          |          |          |
              10         20         30         40         50         60
```

FIG. 10

```
         10         20         30         40         50         60
         |          |          |          |          |          |
  1  MGAPVLPAAF GFLASARTGG GRAPGPVFAT RGSHTDIDTP QGERSLAATL VHAPSVAPDR   60
 61  AVARSLTGAP TTAVLAGEIY NRDELLSVLP AGPAPEGDAE LVLRLLERYD LHAFRLVNGR  120
121  FATVVRTGDR VLLATDHAGS VPLYTCVAPG EVRASTEAKA LAAHRDPKGF PLADARRVAG  180
181  LTGVYQVPAG AVMDIDLGSG TAVTHRTWTP GLSRRILPEG EAVAAVRAAL EKAVAQRVTP  240
241  GDTPLVVLSG GIDSSGVAAC AHRAAGELDT VSMGTDTSNE FREARAVVDH LRTHREITI   300
301  PTTELLAQLP YAVWASESVD PDIIEYLLPL TALYRALDGP ERRILTGYGA DIPLGGMHRE  360
361  DRLPALDTVL AHDMATFDGL NEMSPVLSTL AGHWITHPYW DREVLDLLVS LEAGLKRRHG  420
421  RDKWVLRAAM ADALPAETVN RPKLGVHEGS GTTSSFSRLL LDHGVAEDRV HEAKRQVVRE  480
481  LFDLTVGGGR HPSEVDTDDV VRSVADRTAR GAAZ                              514
         |          |          |          |          |          |
         10         20         30         40         50         60
```

FIG. 11

```
             10         20         30         40         50         60
  1 VERIDSHVSP RYAQIPTFMR LPHDPQRGY  DVVVIGAPYD GGTSYRPGAR FGPQAIRSES   60
 61 GLIHGVGIDR GPGTFDLINC VDAGDINLTP FDMNIAIDTA QSHLSGLLKA NAAFLMIGGD  120
121 HSLTVAALRA VAEQHGPLAV VHLDAHSDTN PAFYGGRYHH GTPFRHGIDE KLIDPAAMVQ  180
181 IGIRGHNPKP DSLDYARGHG VRVVTADEFG ELGVGGTADL IREKVGQRPV YVSVDIDVVD  240
241 PAFAPGTGTP APGGLLSREV LALLRCVGDL KPVGFDVMEV SPLYDHGGIT SILATEIGAE  300
301 LLYQYARAHR TQLZ                                                    314
             10         20         30         40         50         60
```

FIG. 12

```
             10         20         30         40         50         60
             |          |          |          |          |          |
  1  MASPIVDCTP YRDELLALAS ELPEVPRADL HGFLDEAKTL AARLPEGLAA ALDTFNAVGS   60
 61  EDGYLLLRGL PVDDSELPET PTSTPAPLDR KRLVMEAMLA LAGRRLGLHT GYQELRSGTV  120
121  YHDVYPSPGA HYLSSETSET LLEFHTEMAY HILQPNYVML ACSRADHENR AETLVGSVRK  180
181  ALPLLDEKTR ARLFDRKVPC CVDVAFRGGV DDPGAIANVK PLYGDANDPF LGYDRELLAP  240
241  EDPADKEAVA HLSQALDDVT VGVKLVPGDV LIIDNFRTTH ARTPFSPRWD GKDRWLHRVY  300
301  IRTDRNGQLS GGERAGDTIS FSPRRZ                                       326
             |          |          |          |          |          |
             10         20         30         40         50         60
```

FIG. 13

```
             10         20         30         40         50         60
             |          |          |          |          |          |
  1  MSDSTPKTPR GFVVHTAPVG LADDGRDDFT VLASTAPATV SAVFTRSRFA GPSVVLCREA   60
 61  VADGQARGVV VLARNANVAT GLEGEENARE VREAVARALG LPEGEMLIAS TGVIGRQYPM  120
121  ESIREHLKTL EWPAGEGGFD RAARAIMTTD TRPKEVRVSV GGATLVGIAK GVGMLEPDMA  180
181  TLLTFFATDA RLDPAEQDRL FRRVMDRTFN AVSIDTDTST SDTAVLFANG LAGEVDAGEF  240
241  EEALHTAALA LVKDIASDGE GAAKLIEVQV TGARDDAQAK RVGKTVVNSP LVKTAVHGCD  300
301  PNWGRVAMAI GKCSDDTDID QERVTIRFGE VEVYPPKARG DQADDALRAA VAEHLRGDEV  360
361  VIGIDLAIAD GAFTVYGCDL TEGYVRLNSE YTTZ                              394
             |          |          |          |          |          |
             10         20         30         40         50         60
```

FIG. 14

```
         10         20         30         40         50         60
         |          |          |          |          |          |
  1  METTRSTTAD EGFDAGVRGV VAPTDAPGGT LRLVRTDDFD SLDPGNTYA YTWNFLRLIG   60
 61  RTLVTFDTAP GKAGQRLVPD LAESLGESSE DGRVWTYRLR EGLRYEDGTP VVSADIKHAI  120
121  ARSNYGTDVL GAGPTYFRHL LGTEYGGPWR EPDADGPVTL ETPDERTLVF RLREPFAGMD  180
181  LLATMPSTTP VPRDRDTGAE YRLRPVATGP YRIVSYTRGE LAVLEPNPHW DPETDPVRVQ  240
241  RASRIEVHLG KDPHEVDRML LAGEAHVDLA GFGVQPAAQE RILAEPELRA HADNPLTGFT  300
301  WTYCLSSRIA PFDNVHCRRA VQFATDKAAM QEAYGGAVGG DIATTLLPPT LDGYKHFDRY  360
361  PVGPEGTGDL EAARAEIKLA GMPDGFRTRI AARKDRLKEY RAAEALAAGL ARVGIEAEVL  420
421  DFPSGDYFDR YGGCPEYLRE HGIGILMFGW GADFPDGYGF LQQITDGRAI KERGNQMGE   480
481  LDDPEINALL DEGAQCADPA RRAEIWHRID QLIMDHAVIV PYLYPRSLLY RHPDTRNAFV  540
541  TGSFGMYDYV ALGAKZ                                                 556
         |          |          |          |          |          |
         10         20         30         40         50         60
```

FIG. 15

```
            10         20         30         40         50         60
  1  MEVARRTGVR HGTVERRLDR LDRIVGLPLT LRSRHTARLT TAGSRILVAG RRFFHQVDLA   60
 61  ARTHIFGHGS EAVDAPEVLS LVSTEPLLDE VVEDAAASLD LLLSVRHEAP HQVAAQLAGY  120
121  QVDAAYTWSL QSPRHSLERS VRTCEVLDDP LWVILPRDHP LAARREVSLA DLRDETWVSE  180
181  TGPGSEILVT RVFQLAGLTA PTRLHITGAS VARGILRRGD AIGLGSPTHP AVQDPSLVRR  240
241  SLAERPRRTT SLLVDPTIVP RALAGRLAAL IAEVQLRRFA EHHRDLLDEP WWAQWYAERT  300
301  GADARRFGAG PDQGSVPGQA EGRKLDVDDL HLLQAVARHG SINRAAVLS ISQSALTRRI  360
361  HRLEQSLGAR LLLRSPRGTS LTGPTRQFLR QLALYEAEFR EAALACRSVE RPLAQGHWPI  420
421  RRGVAAGARM SGZ                                                     433
            10         20         30         40         50         60
```

FIG. 16

```
      10         20         30         40         50         60
      |          |          |          |          |          |
  1 MPSALQGKVA LITGASSGIG EATARALAAE GAAVAIAARR VEKLRALGDE LTAAGAKVHV  60
 61 LELDVADRQG VDAAVASTVE ALGGLDILVN NAGIMLLGPV EDADITDWTR MIDINLLGLM 120
121 YMTRAALPHL LRSKGTVVQM SSIAGRVNVR NAAVYQATKF GVNAFSETLR QEVTERGVRV 180
181 VVIEPGITDT ELRGHITHTA TKEMYEQRIS QIRKLQAQDI AEAVRYAVTA PHHATVHELF 240
241 IRPTDQVZ                                                        248
      |          |          |          |          |          |
      10         20         30         40         50         60
```

FIG. 17

```
           10         20         30         40         50         60
            |          |          |          |          |          |
  1 MMNEAAPQSD QVAPAYPMHR VCPVDPPPQL AGLRSQKAAS RVTLWDGSQV WLVTSHAGAR   60
 61 AVLGDRRFTA VTSAPGFPML TRTSQLVRAN PESASFIRMD DPQHSRLRSM LTRDFLARRA  120
121 EALRPAVREL LDEILGGLVK GERPVDLVAG LTIPVPSRVI TLLFGAGDDR REFIEDRSAV  180
181 LIDRGYTPEQ VAKARDELDG YLRELVEERI ENPGTDLISR LVIDQVRPGH LRVEEMVPMC  240
241 RLLLVAGHGT TTSQASLSLL SLLTDPELAG RLTEDPALLP KAVEELLRFH STVQNGLARA  300
301 AVEDVQLDDV LIRAGEGVVL SLSAGNRDET VFPDPDRVDV DRDARRHLAF GHGMHQCLGQ  360
361 WLARVELEEI LAAVLRWMPG ARLAVPFEEL DFRHEVSSYG LGALPVTWZ             409
            |          |          |          |          |          |
           10         20         30         40         50         60
```

FIG. 18
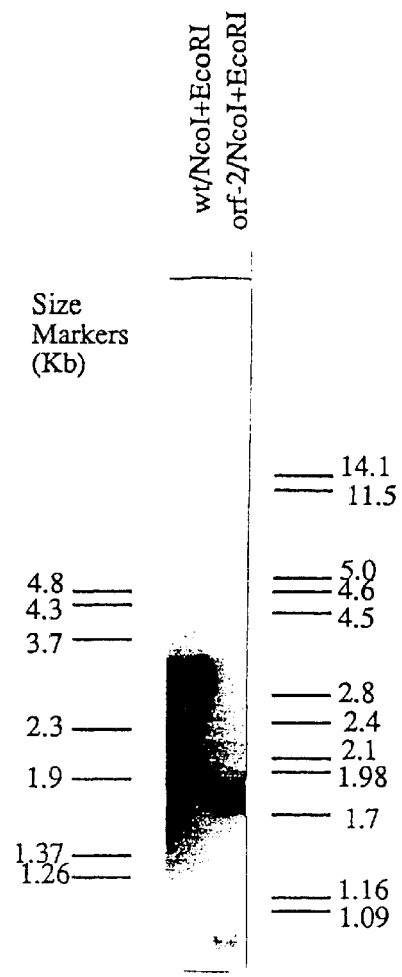
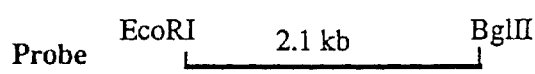
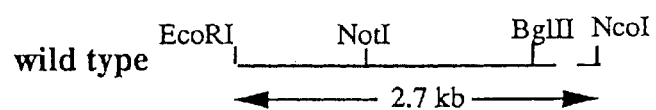
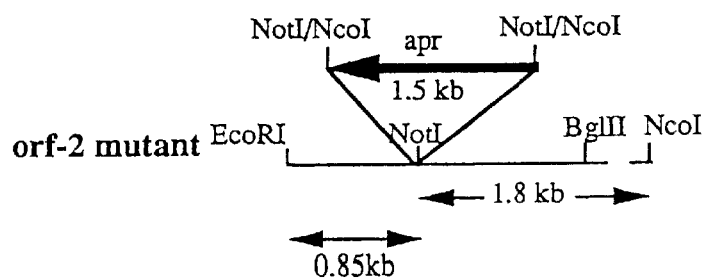

FIG. 21
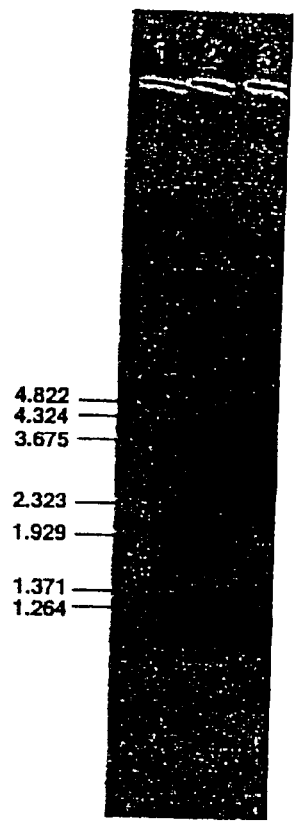
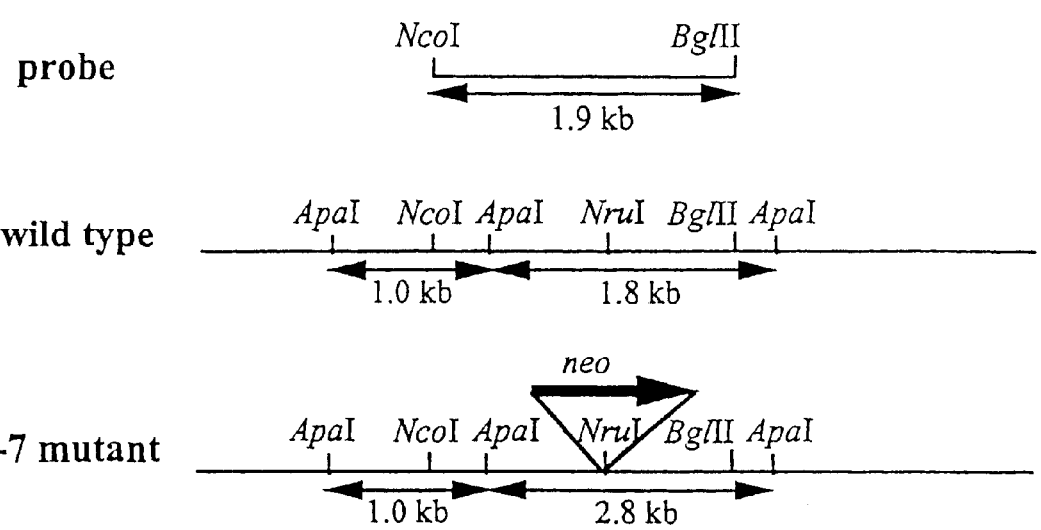

DNA SEQUENCE ENCODING ENZYMES OF CLAVULANIC ACID BIOSYNTHESIS

This invention is a continuation-in-part of application Ser. No. 08/790,462, filed Jan. 29, 1997, now abandoned which is a continuation-in-part of application Ser. No. 08/567,801, filed Dec. 6, 1995, now abandoned which is a continuation of application Ser. No. 08/134,018, filed Oct. 8, 1993, now abandonded.

This invention relates to methods for the production of the antibiotic, clavulanic acid.

BACKGROUND OF THE INVENTION

Clavulanic acid is a broad spectrum beta-lactamase inhibitor and is an important antibiotic for the treatment of infectious diseases. It is produced commercially by the gram-positive mycelial prokaryote *Streptomyces clavuligerus*, which also produces the β-lactam antibiotics penicillin N, desacetoxy cephalosphorin C and cephamycin C. Until recently, however, the pathway employed for clavulanic acid biosynthesis was much less well understood than the pathways leading to these other antibiotics.

Without knowledge of the pathway for clavulanic acid biosynthesis, it was not possible to isolate the genes coding for the key enzymes and to manipulate these genes to increase antibiotic yield or permit production of the antibiotic in heterologous systems.

One of the earliest enzymes of the pathway to be purified and characterised was clavaminic acid synthase. Two isozymes have now been identified and characterised (Marsh et al., (1992), Biochem., vol. 31, pp. 12648–657).

European Patent Application 0349121 describes a 6.8 kb Bgl II restriction fragment isolated from *S. clavuligerus* that encodes a portion of the genetic information involved in clavulanic acid synthesis. No further characterization of this fragment was performed nor was the utility of this fragment determined.

Marsh et al (1992, Biochem. vol 31, pp. 12648–657) cloned and sequenced two isozymes of clavaminate synthase cs1 and cs2 separated by 28 kb, however their location relative to the cephamycin and penicillin biosynthetic clusters was not determined. Ward and Hodgson (1993, FEMS Microbiol. Lett. vol 110, pp. 239–242) reported on the occurrence of a biosynthetic gene cluster for clavulanic acid. Aidoo et al (1994, Gene vol 147, pp. 41–46) cloned and sequenced cla the gene encoding a protein (possibly proclavaminic acid amidinohydrolase) involved in clavulanic acid production. They reported that this gene was upstream from and adjacent to an ORF with the identical sequence of cs2. Paradkar and Jensen (1995, J Bacteriol, vol 177, pp. 1307–1314) further analyzed a 6.6 kb Bgl II fragment from *S. clavuligerus* comprising cs2 and through gene disruption experiments demonstrated its role in clavulanic acid synthesis.

Until the work of the present inventors, the complete complement of genes required for clavulanic acid synthesis had not been identified.

The present inventors have now isolated, cloned and sequenced a 15 kb DNA fragment from *S. clavuligerus* which encodes 10 ORFs. Within this 15 kb of DNA lies an 11.6 kb Eco RI fragment which codes for eight proteins and enables the production of clavulanic acid by transformants of non-clavulanic-producing organisms. This 11.6 kb fragment includes 8 complete ORFs (ORFs 2 to 9), two of which have been previously characterized (Marsh et al 1992, Paradkar and Jensen 1995). ORF1, which is incomplete, is not involved in clavulanic acid synthesis, ORF4 encodes the CLA protein and ORF5 is cs2, encoding one of the isozymes of clavaminate synthase. The function of the other remaining ORFs within this 11.6 kb fragment or their role in clavulanic acid synthesis is unknown.

SUMMARY OF THE INVENTION

An isolated genomic DNA molecule of 15 kb is provided comprising the nucleotide sequence set out in SEQ ID NO:1. This DNA molecule comprises 10 ORFs, eight of which are involved in clavulanic acid synthesis. A process is provided for producing clavulanic acid in a transformant of a non-clavulanate-producing host.

The present invention provides isolated DNA molecules comprising the nucleotide sequence of SEQ ID NO: 15, 16, and 19 to 22.

Furthermore, the present invention is directed to DNA molecules comprising the nucleotide sequences that encode the amino acid sequence found in SEQ ID NO's: 4, 5, and 8 to 11.

This invention also embraces DNA molecules comprising a nucleotide sequence of ORFs 2, 3, 6, 7, 8 and 9 and their associated non-transcribed regions. Such isolated DNA molecules have the nucleotide sequences found in SEQ ID NO's: 15, 16 and 19 to 22.

This invention also embraces DNA molecules comprising the nucleotide sequences encoding the amino acid sequences of SEQ ID NO:'s 4, 5, and 8 to 11. These amino acid sequences correspond to the expression products of ORFs 2, 3, 6, 7, 8 and 9 as defined in SEQ ID NO's: 4, 5 and 8 to 11.

This invention is also directed to recombinant vectors that comprise DNA molecules as defined above where hosts that have been transformed with these recombinant vectors.

This invention is also directed to the process for producing clavulanic acid in a non-clavulantic acid producing host that comprises transforming the host with a DNA molecule as defined above and culturing the host under suitable conditions to produce clavulanic acid.

Furthermore, this invention is directed to processes for enhancing clavulanic acid production in a clavulanic acid producing host comprising transforming the host with a DNA molecule as defined above.

DESCRIPTION OF DRAWINGS

The invention, as exemplified by a preferred embodiment, is described with reference to the accompanying drawings in which:

FIG. 1 shows the N terminal amino acid sequence of CLA (amino acid residues 1–25 of SEQ ID NO:6), the potential codon corresponding with this sequence (SEQ ID NO:24) and the nucleotide sequence of a probe (SEQ ID NO:25) directed to the underlined region of the sequence. The nucleotide sequence of the actual sequence is defined in SEQ ID NO:1, specifically nucleotides 5687–5710 of SEQ ID NO:1, 3665–3678 of SEQ ID NO:13, or 34–57 of SEQ ID NO:17.

FIG. 6 shows a Southern blot of NcoI digests of genomic DNA from five presumptive mutants (lanes 1–5) and from wild-type *S. clavuligerus* (lane 6). Panel A: membranes probed with cla-specific probe. Panel B: membranes probed with tsr-specific probe.

FIG. 7 shows restriction enzyme maps of *S. clavuligerus* DNA inserts in cosmids. FIG. 7(A). Restriction enzyme map of cosmid K6L2. FIG. 7(B). Partial restriction enzyme map of cosmid K8L2. FIG. 7(C). Restriction map of cosmids K6L2 and K8L2 indicating location of pcbC gene in relation to cla. FIG. 7(D). The 2.0 kb NcoI fragment encompassing the cla gene used in generating nested deletions for sequencing. Abbreviations: Ba, BamHI; B,BglII; E,EcoR1; K,KpnI; N, NcoI; S,SalI; and Sm,SmaI.

FIG. 8 shows the deduced amino acid sequence (SEQ ID NO:3) of ORF1.

FIG. 9 shows the deduced amino acid sequence (SEQ ID NO:4) of ORF2.

FIG. 10 shows the deduced amino acid sequence (SEQ ID NO:5) of ORF3.

FIG. 11 shows the deduced amino acid sequence (SEQ ID NO:6) of ORF4.

FIG. 12 shows the deduced amino acid sequence (SEQ ID NO:7) of ORF5.

FIG. 13 shows the deduced amino acid sequence (SEQ ID NO: 8) of ORF6.

FIG. 14 shows the deduced amino acid sequence (SEQ ID NO :9) of ORF7.

FIG. 15 shows the deduced amino acid sequence (SEQ ID NO:10) of ORF8.

FIG. 16 shows the deduced amino acid sequence (SEQ ID NO:11) of ORF9.

FIG. 17 shows the deduced amino acid sequence (SEQ ID NO:12) of ORF10.

FIGS. 18 to 23. The upper panel shows the results of Southern hybridizations using the probes and gene fragments as set forth in the restriction maps of the lower panel.

FIG. 18 shows the construction of the orf-2 mutant.

FIG. 19 shows the construction of the orf-3 mutant.

FIG. 20 shows the construction of the orf-6 mutant.

FIG. 21 shows the construction of the orf-7 mutant.

FIG. 22 shows the construction of the orf-8 mutant.

FIG. 23 shows the construction of the orf-9 mutant.

DETAILED DESCRIPTION OF THE INVENTION

Figure 2:
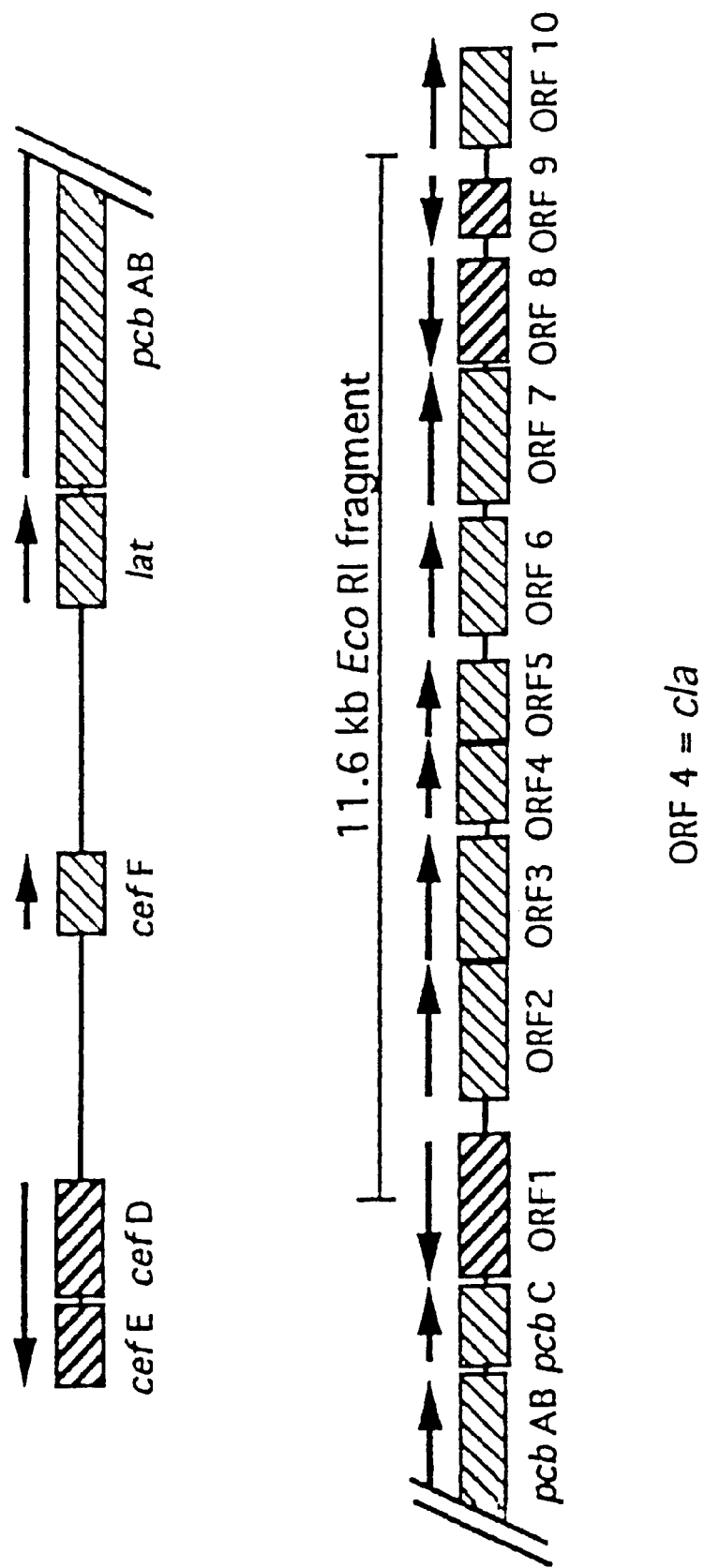
FIG. 2 shows the location of the open reading frames downstream from pcbC.
Figure 3:
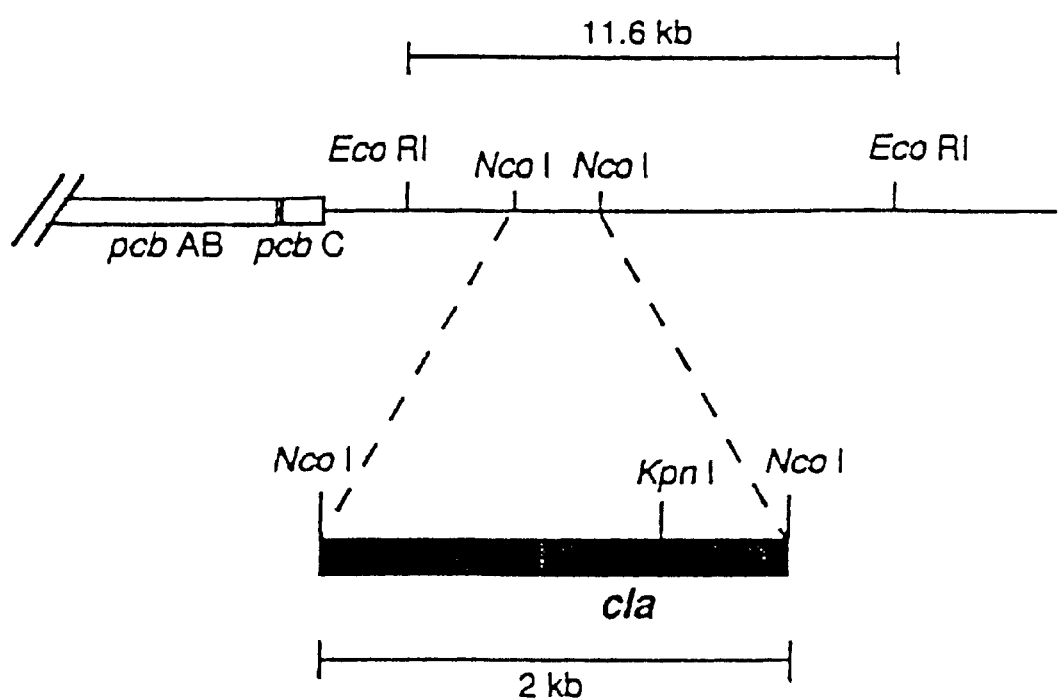
FIG. 3 shows a partial restriction map in the region surrounding cla (ORF4), SEQ ID NO:6.
Figure 4:
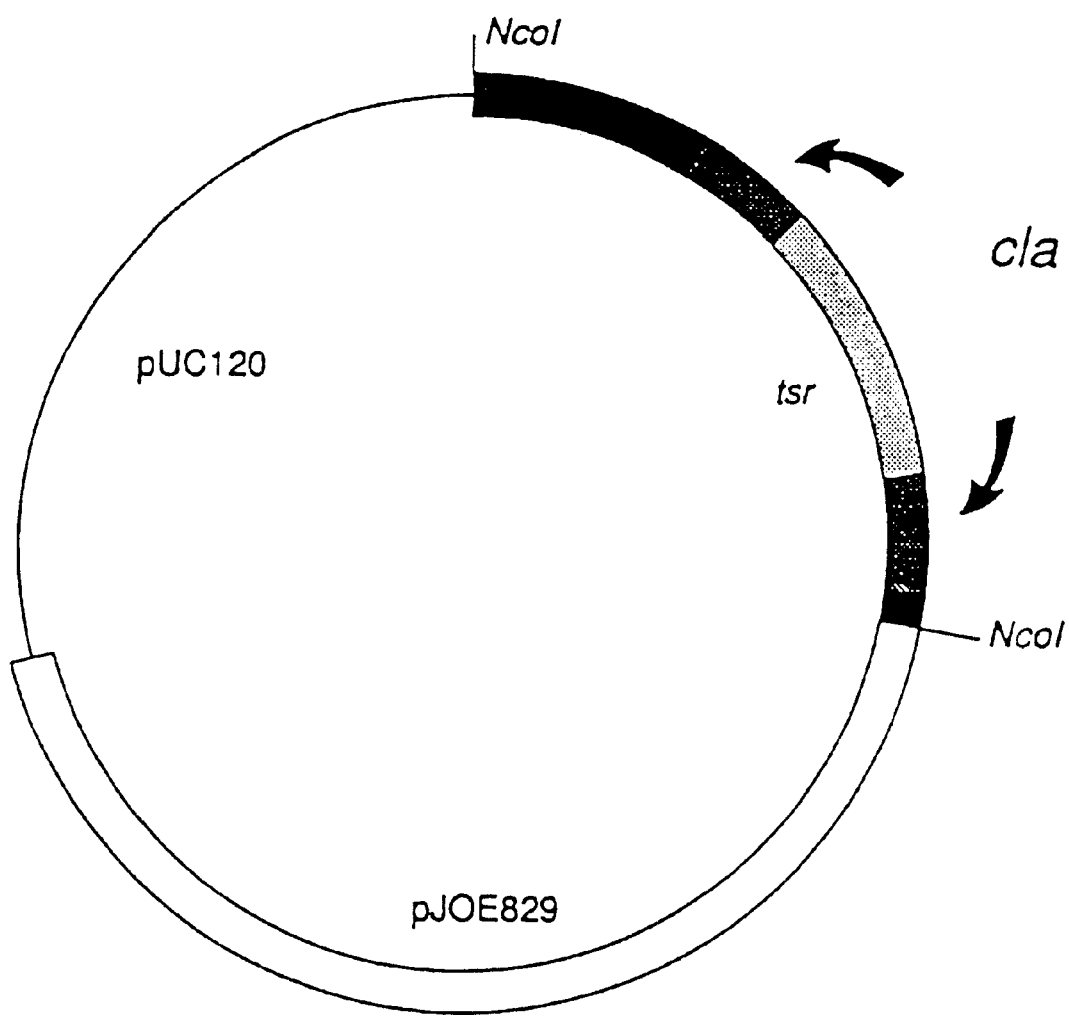
FIG. 4 shows a shuttle vector used for disruption of the cla gene.

Production of penicillin and cephamycin antibiotics in *S. clavuligerus* starts with the conversion of lysine to α-aminoadipic acid (Madduri et al., (1989), J. Bacteriol., v. 171, pp. 299–302; (1991), J. Bacteriol., v. 173, pp. 985–988). α-Aminoadipic acid then condenses with cysteine and valine to give δ-(L-α-aminoadipyl)-L cysteinyl-D-valine (ACV) by the action of aminoadipyl cysteinyl-valine synthetase (ACVS). ACV is converted by isopenicillin N synthase (IPNS) to isopenicillin N, and, through a series of reactions, to desacetoxycephalosporin C and ultimately to cephamycin C (Jensen et al., (1984), Appl. Microbiol. Biotechnol., v. 20, pp 155–160).

The ACVS of *S. clavuligerus* has been purified and partially characterized by three separate groups, and estimates of its molecular weight vary from 350,000 to 500,000 Da (Jensen et al., (1990) J. Bacteriol., v. 172, pp. 7269–7271; Schwecke et al., (1992), Eur. J. Biochem., v. 205, pp. 687–694; Zhang and Demain, (1990), Biotech Lett., v. 12, pp. 649–654). During their purification, Jensen et al. observed a 32,000 Da protein which co-purified with ACVS despite procedures which should remove small molecular weight components. It has now been found that this protein is not related to ACVS but rather to clavulanic acid biosynthesis. It has been designated CLA.

In accordance with one embodiment of the invention, the present inventors have identified, cloned and sequenced the gene (cla) encoding this protein.

In accordance with a further embodiment of the invention, the inventors have cloned and sequenced a 15 kb stretch of genomic DNA from *S. clavuligerus* which includes the cla gene. Within this 15 kb sequence, the inventors have identified an 11.6 kb DNA fragment which, when introduced into the non-clavulanate producer *S. lividans* as described in Example 4, enabled that species to produce clavulanic acid. This indicates that the 11.6 kb fragment contains all the genetic information required for clavulanate production.

As will be understood by those skilled in the art, the identification of the DNA sequence encoding the enzymes required for clavulanate synthesis will permit genetic manipulations to modify or enhance clavulanate production. For example, clavulanate production by *S. clavuligerus* may be modified by introduction of extra copies of the gene or genes for rate limiting enzymes or by alteration of the regulatory components controlling expression of the genes for the clavulanate pathway.

Heterologous organisms which do not normally produce clavulanate may also be enabled to produce clavulanate by introduction, for example, of the 11.6 kb DNA sequence of the invention by techniques which are well known in the art, as exemplified herein by the production of *S. lividans* strains capable of clavulanate synthesis. Such heterologous production of clavulanic acid provides a means of producing clavulanic acid free of other contaminating clavams which are produced by *S. clavuligerus*.

Suitable vectors and hosts will be known to those skilled in the art; suitable vectors include pIJ702, pJOE829 and pIJ922 and suitable hosts include *S. lividans, S. parvulus, S. griseofulvus, S. antibioticus* and *S. lipmanii*.

Additionally, the DNA sequences of the invention enable the production of one or more of the enzymes of the clavulanate pathway by expression of the relevant gene or genes in a heterologous expression system.

The DNA sequences coding for one or more of the pathway enzymes may be introduced into suitable vectors and hosts by conventional techniques known to those skilled in the art. Suitable vectors include pUC118/119 and pET-11 and suitable hosts include many organisms, including *E. coli* strains such as MV1193 and BL21(DE3).

An oligonucleotide probe (SEQ ID NO:25) based on the N-terminal amino acid sequence of CLA (amino acid residues 1–25 of SEQ ID NO:6) was constructed as shown in FIG. 1 and was used to isolate the gene coding for the protein from S. clavuligerus, as described in Example 1.

The gene was found to be located in the S. clavuligerus chromosome about 5.7 kb downstream of pcbC, the gene which encodes isopenicillin N synthase. The gene contains a 933 bp open reading frame (ORF), encoding a protein of molecular weight 33,368. The deduced amino acid sequence was compared to database sequences and showed greatest similarity to enzymes associated with arginine metabolism, notably agmatine, ureohydrolase and arginases.

When an internal fragment of the cla gene was labelled and used to probe restriction endonuclease digests of genomic DNA from a variety of other Streptomyces and related species, evidence of homologous sequences was seen only in other clavulanic acid or clavam metabolite producers, including Streptomyces jumonjinensis, Streptomyces lipmanii and Streptomyces antibioticus. No cross reactivity was seen to the β-lactam producing species Nocardia lactamdurans, Streptomyces griseus or Streptomyces cattleya, nor to any of a variety of other Streptomyces species which do not produce β-lactam compounds, including S. fradiae ATCC 19609, S. venezuelae 13s and S. griseofulvus NRRL B-5429.

Disruption of the cla gene, as described in Example 3, led to loss of the ability to synthesise clavulanic acid.

A 15 kb DNA sequence extending downstream from pcbC was cloned and sequenced as described in Example 5. The nucleotide sequence is shown in SEQ ID NO:1. When this (SEQ ID NO:1) sequence information was analysed for percent G+C as a function of codon position (Bibb et al., (1984), Gene, v. 30, pp. 157–166), ten complete ORFs were evident, as shown in FIG. 2. ORF 4 corresponds to cla. ORF 1,7 & 8 are oriented in the opposite direction to pcbC. ORFs 2–6 and ORF 10 are all oriented in the same direction as pcbC. ORFs 2 and 3, and ORFs 4 and 5 are separated by very short intergenic regions suggesting the possibility of transcriptional and translational coupling. Table 1 summarises the nucleotide sequences and lengths of ORFs 1–10.

TABLE 1

| ORF # | Start location (bp) | End location (bp) | Length (bp) | Size of ORF (aa residues) | SEQ ID NO. |
|---|---|---|---|---|---|
| 1* | 1764 | 109 | 1656 | 552 | 14 |
| 2 | 2257 | 3978 | 1722 | 574 | 15 |
| 3 | 3981 | 5522 | 1542 | 514 | 16 |
| 4 | 5695 | 6636 | 942 | 314 | 17 |
| 5 | 6652 | 7629 | 978 | 326 | 18 |
| 6 | 7936 | 9117 | 1182 | 394 | 19 |
| 7 | 9282 | 10949 | 1668 | 556 | 20 |
| 8* | 12337 | 11039 | 1299 | 433 | 21 |
| 9* | 13406 | 12663 | 744 | 248 | 22 |
| 10 | 13810 | 15036 | 1227 | 409 | 23 |

*Asterisks denote ORFs which are oriented in the opposite direction.

When the predicted amino acid sequences of proteins encoded by ORFs 1–10 were compared to protein sequence databases, some similarities were noted in addition to the already mentioned similarity between CLA and enzymes of arginine metabolism. ORF 1 (SEQ ID NO's: 3 and 14) showed a low level of similarity to penicillin binding proteins from several different microorganisms which are notable for their resistance to β-lactam compounds.

An EcoRI fragment of the 15 kb DNA sequence, containing 11.6 kb DNA, was cloned into a high copy number shuttle vector and introduced into S. lividans, as described in Example 4. Of seventeen transformants examined, two were able to produce clavulanic acid, indicating that the 11.6 kb fragment contains all the necessary genetic information for clavulanic acid production.

This 11.6 kb fragment encompasses ORF 2 to ORF 9 of the 15 kb DNA sequence.

ORF 2 (SEQ ID NO's:4 and 15) shows a high degree of similarity to acetohydroxyacid synthase (AHAS) enzymes from various sources. AHAS catalyses an essential step in the biosynthesis of branched chain amino acids. Since valine is a precursor of penicillin and cephamycin antibiotics, and valine production is often subject to feedback regulation, it is possible that a deregulated form of AHAS is produced to provide valine during the antibiotic production phase. Alternatively, an AHAS-like activity may be involved in clavulanic acid production. While the presently recognized intermediates in the clavulanic acid biosynthetic pathway do not indicate a role for AHAS, the final step in the biosynthetic pathway, conversion of clavaminic acid to clavulanic acid, requires NADPH, and either pyruvate or α-ketobutyrate as well as other cofactors (Elson et al., (1987), J. Chem. Soc. Chem. Commun., pp. 1739–1740). It is striking that these same substrates and cofactors are required for AHAS activity. Perhaps the conversion of clavaminate to clavulanate actually involves several steps, one of which is catalyzed by an AHAS-like activity. ORFs 3 (SEQ ID NO's:5 and 16) does not show a significant similarity to any proteins in the data bases. ORF 6 (SEQ ID NO's:8 and 19) shows similarity to ornithine acetyltransferase. Ornithine has been suggested to be the immediate precursor of a 5-C fragment of the clavulanic acid skeleton, but the details of the reaction required for the incorporation of ornithine are unknown. ORF 7 (SEQ ID NO's:9 and 20) shows weak similarity to protein XP55 from S. lividans, and a lower level of similarity to oligopeptide binding proteins from various other species. Similarly, ORF 8 (SEQ ID NO:10 and 21) shows weak similarity to several transcription activator proteins, and ORF 9 (SEQ ID NO's:11 and 22) shows weak similarity to ribitol 5 PO$_4$ dehydrogenase-type enzymes. ORF 10 (SEQ ID NO:12 and 23) shows a high similarity to cytochrome P450 type enzymes from other Streptomyces species.

ORF5 has now been identified as the gene for clavaminate synthase II (Marsh (1993) supra).

Figure 5:
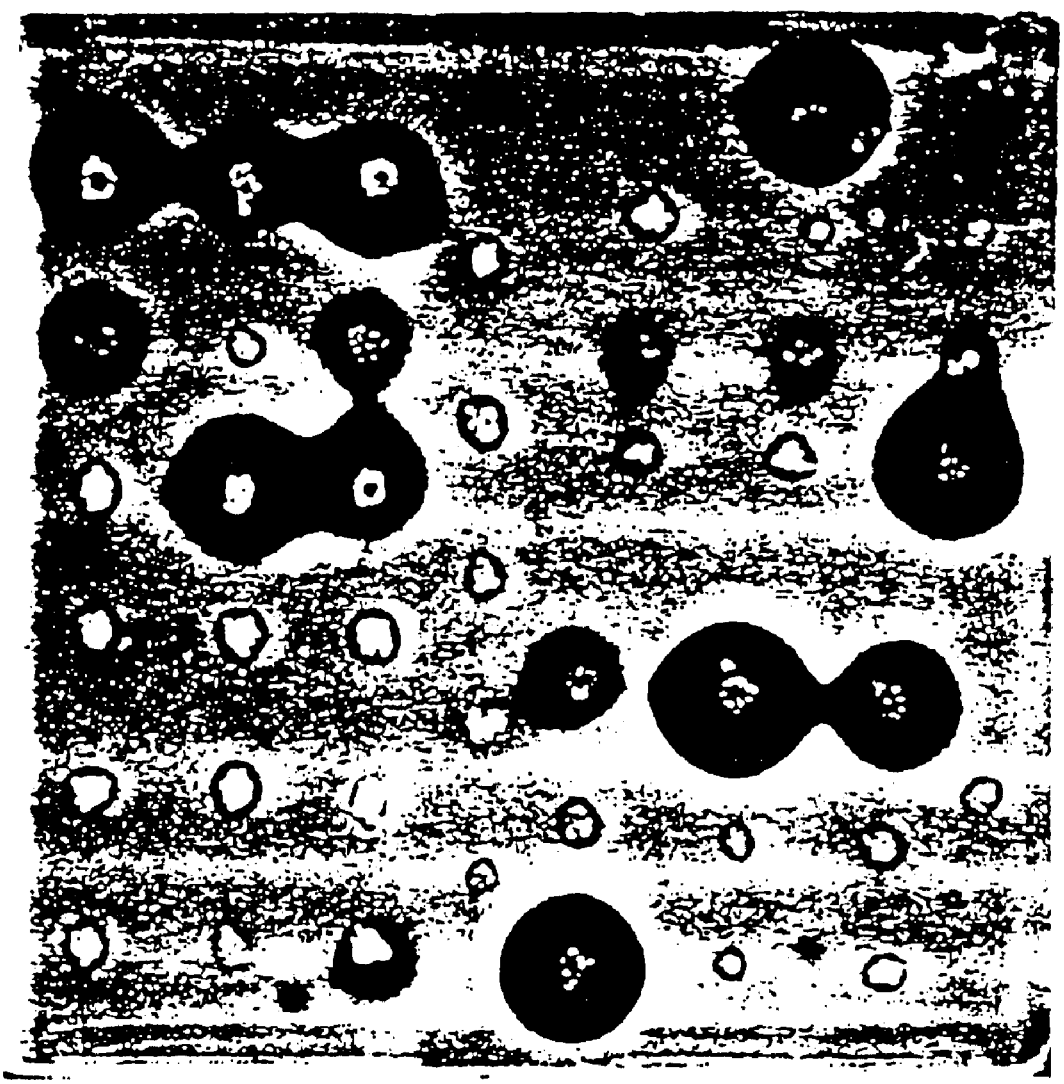
FIG. 5 shows a photograph of an agar plate bearing cultures of *S. lividans* transformants.

When a plasmid isolated from one of the two clavulanic acid-producing transformants was retransformed into S. lividans, about 40–45% of the resulting colonies were able to produce clavulanic acid, as shown in FIG. 5.

EXAMPLES

Example 1

Bacterial Strains, Vectors and Growth Conditions

Streptomyces clavuligerus NRRL 3585, Stretomyces jumonjinenisis NRRL 5741, Streptomyces lipmanii NRRL 3584, Streptomyces griseus NRRL 3851, Nocardia lactamdurans NRRL 3802 and Streptomyces cattleya NRRL 3841 were provided by the Northern Regional Research Laboratories, Peoria, Ill. Streptomyces antibioticus ATCC 8663 and Streptomyces fradiae ATCC 19609 were obtained from the American Type Culture Collection. Streptomyces lividans strains 1326 and TK24 were provided by D. A. Hopwood (John Innes Institute, Norwich, U.K.), Streptomyces venezuelae 13s and Streptomyces griseofuscus NRRL B-5429 were obtained from L. C. Vining (Department of Biology, Dalhousie University, Halifax, N. S.). Cultures were maintained on either MYM (Stuttard (1982) J. Gen. Microbiol., v. 128, pp. 115–121) or on a modified R5 medium (Hopwood et al. (1985) in "Genetic Manipulation of Streptomyces: a laboratory manual", John Innes Foundation, U.K.) containing maltose instead of glucose and lacking sucrose (R5-S). *Escherichia coli* MV1193 (Zoller and Smith (1987) Methods in Enzymology, v. 154, pp. 329–349), used as recipient for all of the cloning and subcloning experiments, was grown in Luria Broth (LB; Sambrook et al. (1989) in "Molecular Cloning: a laboratory manual", Cold Spring Harbour, N.Y.) or on LB agar (1.5%) plates containing ampicillin (50 µg/mL) or tetracycline (10 µg/mL). The cloning vectors pUC118 and pUC119 (Vieira and Messing (1987) Methods in Enzymology, v. 153, pp. 3–11) were provided by J. Vieira. (Waksman Institute of Microbiology, Rutgers University, Piscataway, N.J.). The plasmid vector pJOE829 was generously provided by J. Altenbuchner (University of Stuttgart, Stuttgart, Germany). The plasmid pIJ702 was obtained from the American Type Culture Collection. Restriction enzymes were purchased from Boehringer Mannheim, and used according to the manufacturers' specifications.

Separation of CLA from ACVS

CLA was previously characterized as a 32,000 Da molecular weight protein present in preparations of highly purified ACVS (Jensen et al. (1990), supra). The small size of CLA suggested that its co-purification with ACVS resulted from a physical association between the two proteins.

ACVS and CLA were resolved by applying a 0.2 ml sample of purified ACVS containing CLA onto a Superose 6 HR 10/30 (Pharmacia), which was equilibrated and eluted in 0.1 M MOPS buffer, pH 7.5 containing 0.05 M KCl, 1 mM dithiothreitol, and 20% glycerol, at a flow rate of 0.25 ml/min.

Comparison of the CLA retention time with those of molecular weight standards indicated that the native molecular weight of CLA was in excess of 270 kDa. The difference in molecular weight between native and denatured forms of CLA suggests that the native protein exists as an oligomer of eight identical subunits.

Isolation of Gene (cla) for CLA

N-terminal amino acid sequence information for CLA was obtained by electrophoretically transferring the protein from SDS polyacrylamide gels onto Immobilon membranes (Millipore Ltd.,) and submitting the material to the Protein Microsequencing Laboratory (University of Victoria,) for analysis. Information obtained for 25 amino acids at the N-terminus (amino acid residues 1–25 of SEQ ID NO:6) was used to prepare a 24 mer oligonucleotide probe (SEQ ID NO:25) with 8-fold degeneracy to the amino acid sequence underlined in FIG. 1. The amino acids in brackets indicate ambiguities in the N terminal sequence. The actual DNA sequence from the cloned fragment is indicated in SEQ ID No:1.

The probe was designed as an 8-fold degenerate mixture of oligonucleotides to take into consideration the biased codon usage of streptomyces (Wright and Bibb (1992), Gene, v. 113, pp. 55–65).). End-labelled probe was then used to screen a cosmid library of *S. clavuligerus* genomic DNA fragments.

A library of *S. clavuligerus* genomic DNA fragments (15–22 kb size fractionated fragments) was constructed as previously described (Doran et al. (1990), J. Bacteriol, v. 172, pp. 4909–4918). Using the cosmid vector pLAFR3. A collection of 1084 isolated *E. coli* colonies contained recombinant cosmids was screened for the presence of cla using the 24-mer mixed oligonucleotide probe (FIG. 1) which had been end-labelled with [$\gamma$-$^{32}$P]dATP and polynucleotide kinase (Boehringer Mannheim). Colony hybridization and subsequent washing was performed as described by Sambrook et al., (1989), at 55° C. with a final wash in 0.2×SSC (IX SSC, 0.15M NaCl and 0.015M sodium citrate) and 0.1% SDS.

Five colonies which gave strong hybridization signals were isolated from the panel of 1084 clones, and restriction analysis showed that the positive clones contained overlapping fragments of DNA. Two clones, K6L2 and K8L2, with sequences that spanned about 40 kb of the *S. clavuligerus* genome, were chosen for further analysis. Clone K8L2 contained about 22 kb of *S. clavuligerus* genomic DNA and included a portion of cla and all of the pcbC gene which encodes IPNS in the penicillin/cephamycin biosynthetic pathway. A restriction map of K6L2 is shown in FIG. 7. Within the approximately 27 kb of DNA contained in K6L2, the oligonucleotide probe hybridized to a 2.0 kb NcoI fragment which was subsequently found to contain the entire cla gene. Hybridization studies, restriction mapping and DNA sequence analysis revealed that cla was situated 5.67 kb downstream of the pcbC gene of *S. clavuligerus* (FIG. 7).

DNA Sequencing and Analysis

Ordered sets of deletions were generated (Henikoff, 1984) extending across the cla region of the 2.0 kb NcoI fragment (FIG. 7(C)). The deletion generated fragments were sequenced in both orientations by the dideoxynucleotide chain termination method of (Sanger et al. (1977), P.N.A.S., v. 74, pp. 5463–5467) using Sequenase (version 2.0) DNA polymerase (United States Biochemical Corporation). Areas of compression in the sequence band pattern were relieved by carrying out reactions using 7-deaza-dGTP in place of dGTP. The nested deletion fragments resided either in pUC118 or pUC119, and were sequenced using the commercially available universal primers.

The nucleotide sequence data were analyzed for the presence of restriction sites, open reading frames (ORFs) and codon usage by the PC-Gene programme (Intelligenetics Corp.). Similarly searches were accomplished with the FASTA program searching the GenPept database (release number 71) available through GenBank (Pearson and Lipman (1988), P.N.A.S., v. 85, pp. 2444–2448).

An ORF at 939 bp with a potential ribosome site 9 bp from the GTG start codon was found which encoded a putative protein with a molecular weight of 33,368 Da. This value is in close agreement to the molecular weight estimated for CLA by SDS-PAGE (Jensen et al., 1990). The analysis of percent G+C as a function of codon position (FRAME analysis), using the algorithm of Bibb et al., (1984), indicated the presence of a typical streptomycete ORF (data not shown) with a G+C content of 70%. Computer aided data base searches for sequences similar to cla revealed a high degree of similarity to agmatine ureohydrolase (40.5% identity over 291 amino acids) and somewhat lower similarity to arginases (29.6% identity over 135 amino acids to arginases from yeast and rat). The *S. clavuligerus* CLA sequence was aligned with the *E. coli* AUH sequence by the FASTA program described above. The AUH sequence had previously been aligned with the three ARG sequences (Szumanski & Boyle (1990), J. Bacteriol., v. 172, pp. 538–547). Identical matches in two or more sequences are indicated with upper case letters.

Example 2

DNA Hybridization

Genomic DNA preparations from various Streptomyces species were isolated as described by Hopwood et al. (1985). For interspecies DNA hybridization analysis, 2.0 µg amounts of genomic DNA preparations were digested with NcoI for 16 h, and electrophoresed in 1.0% agarose gels. The separated DNA fragments were then transferred onto nylon membranes (Hybond-N, Amersham) and hybridized with a cla specific probe prepared by labelling an internal 459 bp SalI fragment (FIG. 1) with [$\alpha^{32}$P]DAPT by nick translation. Hybridization was done as described by Sambrook et al., (1989). Hybridization membranes were washed twice for 30 min in 2×SSC; 0.1% SDS and once for 30 min in 0.1×SSC; 0.1% SDS at 65° C.

Sequences Homologous to cla in Other Streptomycetes

Three of six producers of β-lactam antibiotics, S. clavuligerus, s. lipmanii and S. jumonjinesis showed positive hybridization signals whereas S. cattleya, S. griseus, and N. lactamdurans did not (data not shown). None of the nonproducing strains examined, S. venezuelae, S. lividans, S. fradiae, S. antibioticus and S. griseofuscus gave any signal. All of the streptomycetes that gave positive signals were producers of clam-type metabolites (Elson et al., 1987).

Example 3

Disruption of the Genomic cla Gene

A 2.0 kb NcoI fragment that contained the entire cla gene was digested at its unique KpnI site and the ends made blunt by treatment with the Klenow fragment of E. coli DNA polymerase I. A thiostrepton resistance gene (tsr), isolated as a 1085 bp BclI fragment from pIJ702 and cloned into the BamHI site of pUC118 was excised as a SmaI/XbaI fragment and the ends made blunt as above and ligated into the KpnI site of cla. The ligation mixture was introduced into E. coli MV1193 and the transformants screened for the presence of the tsr gene by colony hybridization (Sambrook et al., 1989).

Replacement of the chromosomal cla gene by a copy disrupted by the insertion of tsr, at an internal KpnI site, was achieved by double recombination. Successful gene replacement was apparent when the 2.0 kb NcoI fragment which carries cla in the wild type organism was replaced by a 3.0 kb NcoI fragment due to the insertion of the 1.0 kb tsr gene in the mutants. Four of the five mutants tested showed the expected increase in the size of the NcoI fragments, and the larger NcoI fragments also hybridized with a tsr specific probe. The fifth mutant was apparently a spontaneous theostrepton resistant mutant.

Antibiotic Assay

The agar diffusion assay was used for determining both penicillin/cephamycin and clavulanic acid production. S. clavuligerus strains to be assayed were grown in 10 ml. amounts of Trypticase Soy Broth (TSB; Baltimore Biological Laboratories) medium with 1.0% starch for 48 h. The cultures were washed twice with 10.3% sucrose and once with MM (Jensen et al. (1982), J. Antibiot., v. 35, pp. 483–490) and the mycelium resuspended in 10.0 mL of MM. Two milliliters of washed cell suspension was inoculated into 100 mL of MM and incubated at 28° C. for 48 h. The cultures were harvested by centrifugation, and the supernatants were assayed for both penicillin/cephamycin and clavulanic acid using bioassay procedures described previously (Jensen et al. (1982), supra).

All of the resulting colonies with disrupted cla genes grew equally well on minimal medium and complex media and produced as much penicillin and cephamycin as did the wild-type, but produced no clavulanic acid (data not shown). HPLC analysis of cell supernatants confirmed the inability of the disrupted cla mutants to synthesize any clavulanic acid (data not shown).

Example 4

Protoplast Formation and Transformation

E. coli competent cell preparation and transformation were as described by Sambrook et al., (1989). Protoplasts of S. clavuligerus were, prepared, transformed and regenerated as described by Bailey et al. (1984), Bio/Technology, v. 2, pp. 808–811, with the following modifications. Dextrin and arginine in the regeneration medium were replaced by starch and sodium glutamate respectively. Protoplasts were heat shocked at 43° C. for 5 min prior to the addition of DNA. Standard procedures were used for protoplasting and transformation of S. lividans (Hopwood et al. (1985)).

The 11.6 kb EcoR1 fragment from K6L2 (FIG. 7) was cloned into the EcoR1 site of pCAT-119. pCAT-119 is derivative of pUC119 which was prepared by insertionally inactivating the ampicillin resistance gene of pUC119 by the insertion of a chloramphenicol acetyltransferase gene (Jensen et al. (1989), Genetics & Molec. Biol. of Ind. Microorg., pp. 239–245 Ed. Hershberger, Amer. Soc. Microbiol). The PCAT-119 plasmid carrying the 11.6 kb fragment was then digested with PstI and ligated to the Streptomyces plasmid pIJ702, which had also been digested with PstI. The resulting bifunctional plasmid carrying the 11.6 kb insert was capable of replicating in either E. coli (with selection for chloramphenicol resistance) or in S. lividans (with selection for thiostrepton resistance). The ligation mixture was transformed to E. coli. Plasmid DNA was isolated from several of the chloramphenicol resistant transformants and analyzed by agarose gel electrophoresis to ensure that the proper plasmid construct was obtained. This isolated plasmid material from E. coli was then transformed into S. lividans as described by Hopwood and transformants were selected by plating onto R2YE medium containing thiostrepton at a concentration of 50 μg/ml.

Thiostrepton resistant S. lividans transformants carrying the bifunctional plasmid with the 11.6 kb insert were patched onto MYM agar plates and allowed to incubate for 48 h at 28° C. before they were overlayered with molten soft nutrient agar containing penicillin G at a concentration of 1 μg/ml and inoculated with Staphylococcus aureus N-2 as indicator organism (Jensen, 1982). (S. aureus N-2 was obtained form the Department of Microbiology Culture Collection, University of Alberta. Any organism which produces a β-lactamase sensitive to clavulanic acid may be used as indicator organism.) Zones of inhibition which appeared around the S. lividans colonies upon incubation overnight at 30° C. were evidence of clavulanic acid production. Clavulanic acid-producing colonies were found amongst these initial S. lividans transformants at a frequency of about 12%. When plasmid DNA was isolated from one of these clavulanic acid-producing transformants and re-introduced into S. lividans, the frequency of clavulanic acid production in these 2nd round transformants was about 40–45%. FIG. 5 shows a photograph of an agar plate bearing 2nd. round transformants. Zones of inhibition are seen as clear areas in the agar; these appear on the photograph as dark circular areas.

Example 5

Sequencing of 15 kb DNA Fragment

Ordered sets of deletions were generated as described in Example 1 using fragments of the DNA insert from the cosmid clone K6L2 (FIG. 7) and subcloned into the E. coli plasmids pUCI118 and pUC119. Overlapping fragments were chosen which extended from the end of the pcbC gene downstream for a distance of about 15 kb ending at the BglII site. The deletion generated fragments were sequenced in both orientations as described in Example 1. The sequence is shown in SEQ ID NO:1.

Example 6

Gene Disruption of the ORFs Contained within the 12 kb Fragment

Gene disruption experiments were conducted on the various open reading frames (ORF) to determine if a particular ORF was involved in clavulanic acid production or not. In order to determine the role of the various ORFs in clavulanic acid biosynthesis, mutants disrupted in one of the ORFs were constructed by a gene replacement procedure based on that described in Paradkar and Jensen (*Journal of Bacteriology*, March 1995, Vol. 177, no. 5, pages 1307 to 1314).

In all cases, either an apramycin-resistance gene cassette (apr), or a neomycin resistance gene cassette (neo) was used to disrupt the genes encoded within the 12-kb DNA fragment. Before use, unless otherwise indicated, the apr-cassette was modified by adding NcoI restriction sites to both ends. This modification of the apr-cassette has been described in Paradkar and Jensen (*Journal of Bacteriology*, March 1995, Vol. 177, no. 5, pages 1307 to 1314). Since four NcoI sites are present within the 12 kb fragment and present within ORFs 3, 5, 6, and 8, respectively, insertion of the apr-cassette within the NcoI sites created a series of plasmids (called pCATL2) with disruptions in ORFs 3, 5, 6, or 8. The plasmids containing these fragments are referred to as pCATL2orf3, pCATL2orf5, pCATL2orf6, and pCATL2orf8, respectively. The construction of pCATL2orf5 has been previously disclosed (Paradkar and Jensen, *Journal of Bacteriology*, March 1995, Vol. 177, no. 5, pages 1307 to 1314). From each of these plasmids, a smaller fragment carrying only the disrupted gene and some flanking sequence (see details below) was subcloned and finally inserted into the Streptomyces vector pIJ486 (obtained from David A Hopwood, John Innes Institute) for transformation into *S. clavuligerus*. All routine manipulations involved in subcloning were done in *Escherichia coli* using standard cloning vectors, such as pUC119, pBluescript SK+etc. Since ORF2, ORF7 and ORF9 do not contain NcoI sites, the disruptions of these ORFs were done in a slightly different manner. The preparation of ORF2, ORF3, ORF6, ORF7, ORF8 and ORF9 disruption mutants are described in more detail below.

Construction of the Insertional Mutants

1. ORF2 Mutant

NotI-NcoI linker oligonucleotides were added to both ends of the apr gene cassette, and then this modified apr gene fragment was inserted into the NotI site within ORF2 carried on a 2.1-kb EcoRI-BglII fragment. Subsequently, the EcoRI-BglII fragment carrying the disrupted ORF2 was inserted into pIJ486.

Genomic DNA isolated from the wild type (wt) and from an ORF2 mutant was digested with EcoRI and NcoI, and then probed with a 2.1-kb EcoRI-BglII fragment (FIG. 18). The 2.7 kb hybridizing fragment present in the wild type has been replaced with a 1.8 kb fragment in the mutant. A 0.85 kb fragment is also expected to hybridize to the probe in the mutant, but owing to the conditions of electrophoresis under which the gel was that smaller fragment was not retained on the gel. The sizes of the remaining hybridizing fragments are consistent with the replacement of the wild type ORF2 with the apr-disrupted ORF2.

2. ORF3 Mutant

The apr cassette (with NcoI sites on each end) was inserted into the NcoI site within ORF3 carried on a 4 kb EcoRI-KpnI fragment. The fragment carrying the disrupted ORF3 was then subcloned into pIJ486.

Figure 19:
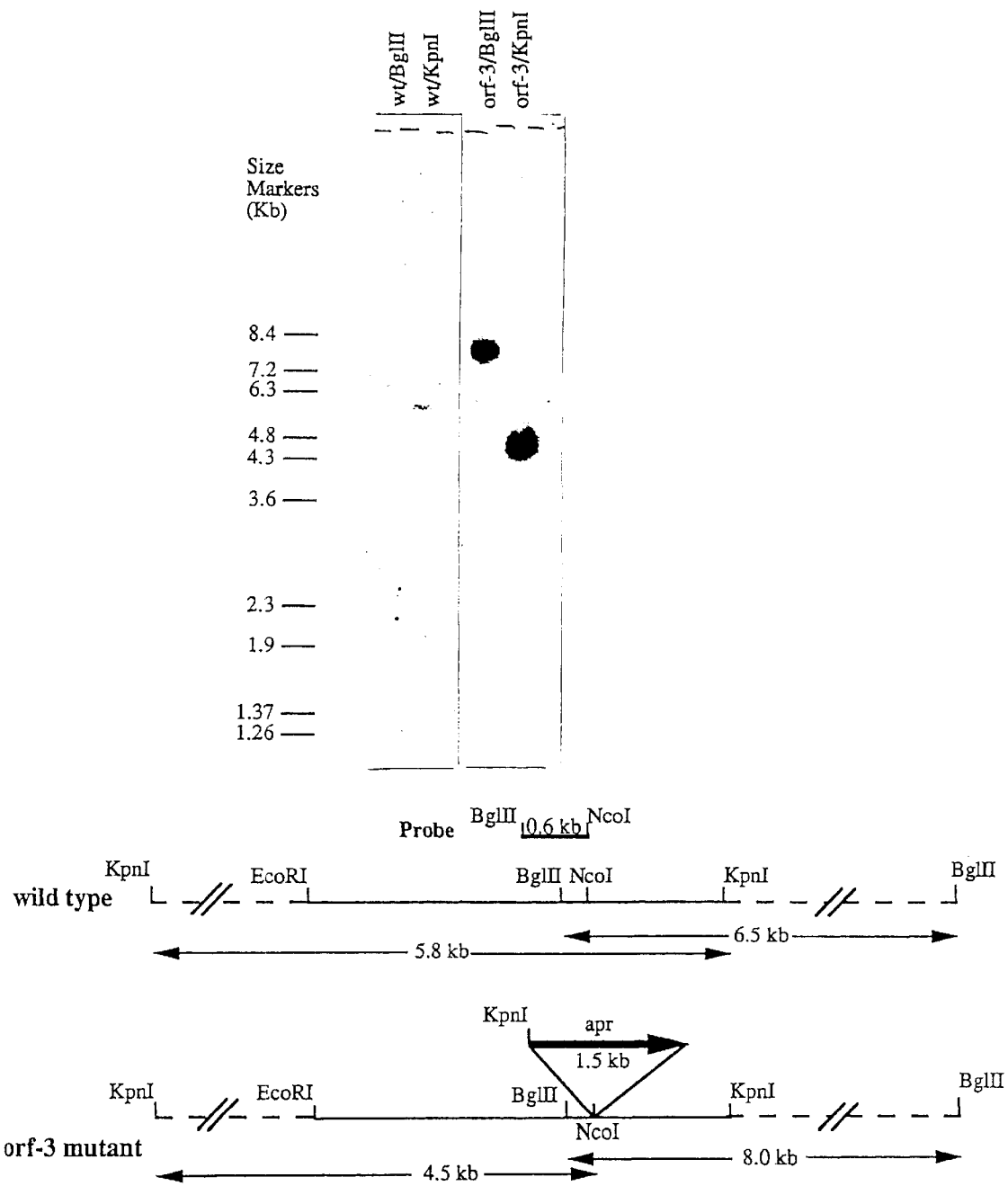

Genomic DNA from the wild type (wt) and from an ORF3 mutant was digested separately with BglII, and with KpnI, and probed with a 0.6-kb BglII-NcoI fragment (FIG. 19). In the BglII digests, the 6.5 kb hybridizing fragment present in the wild type has been replaced with 8 kb fragment in the mutant, while in the KpnI digests, the 5.8 kb fragment has been replaced with a 4.5 kb fragment. The sizes of these hybridizing fragments are consistent with the replacement of the wild type ORF3 with the apr-disrupted ORF3.

3. ORF6 Mutant

An 8-kb BglII fragment carrying the disrupted ORF6 was subcloned from pCATL2orf6 into pIJ486.

Figure 20:
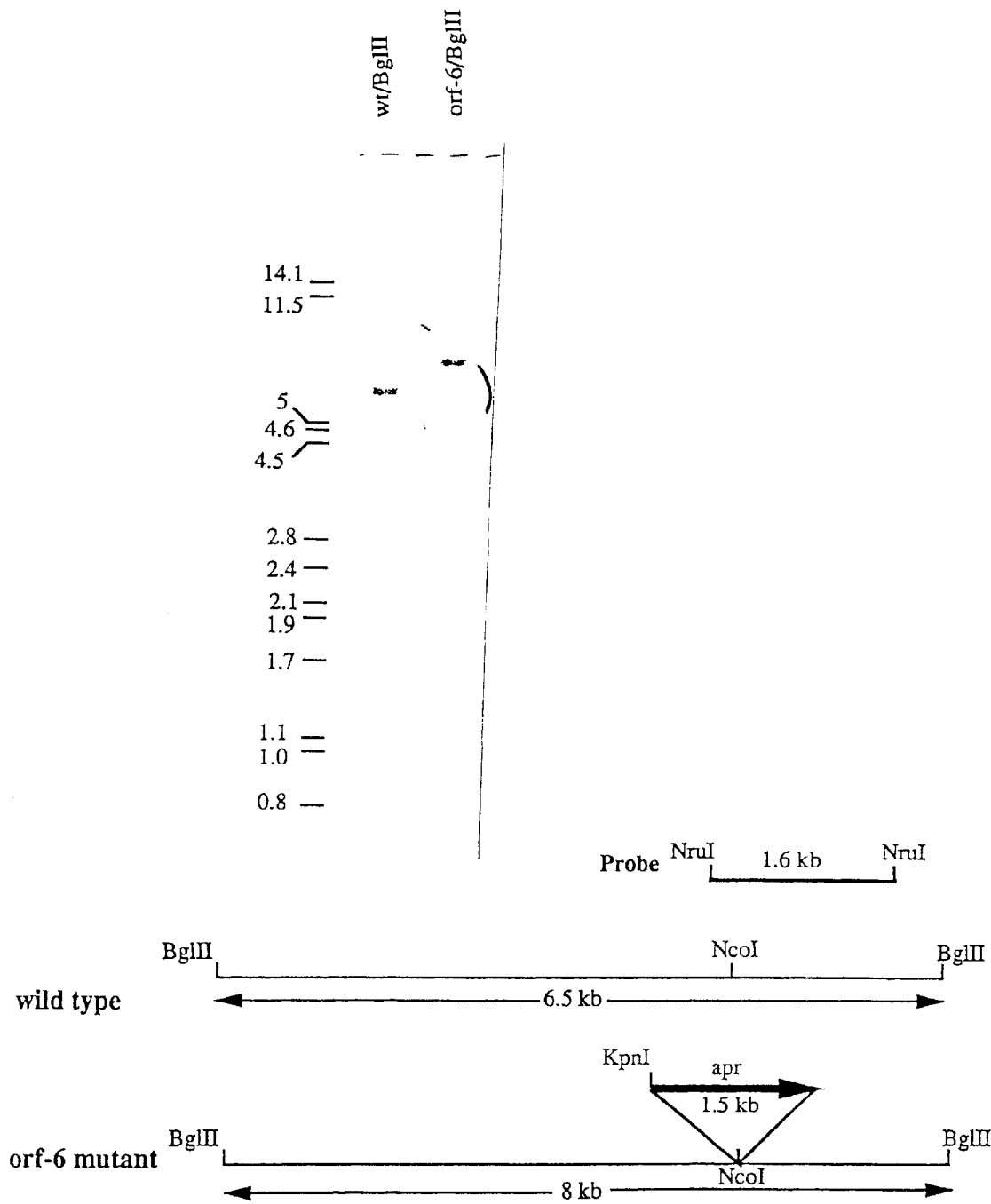

Genomic DNA from the wild type (wt) and from an ORF6 mutant was digested with BglII, and probed with a 1.6-kb NruI fragment (FIG. 20). The 6.5 kb hybridizing fragment present in the wild type has been replaced with an 8 kb fragment in the mutant. The sizes of these hybridizing fragments are consistent with the replacement of the wild type ORF6 with the apr-disrupted ORF6.

4. ORF7 Mutant

The NruI site from the polylinker of the plasmid vector pSL1180 (Pharmacia) was eliminated by digesting with enzymes flanking the NruI site and religating the resulting plasmid. A 1.9 kb BglII-NcoI fragment of *S. clavuligerus* DNA encompassing the ORF7 gene was then cloned into the modified pSL1180 plasmid vector. The neomycin resistance cassette was removed from pFDNEO-S (Denis, F., and R. Brzezinski. 1991. An improved aminoglycoside resistance gene cassette for use in Gram-negative bacteria and Streptomyces. FEMS Microbiol. Lett. 81:261–264), made blunt-ended by treatment with the Klenow fragment of DNA polymerase, and then introduced into the NruI site of the cloned ORF7 gene. The Streptomyces plasmid pJOE829 (Aidoo et al., 1994, Gene 147: 1–46.) was ligated to the vector carrying the disrupted ORF7 gene to allow the creation of a shuttle vector. This gene disruption construct was then used to generate an ORF7 mutant using a gene replacement procedure based on that described in Paradkar and Jensen (*Journal of Bacteriology*, 1995, 177:1307–1314.)

Putative ORF7 disruptant mutants were selected on the basis of their neomycin resistant, hygromycin sensitive phenotype. The identity of the mutants was confirmed by Southern analysis. Genomic DNA from the wild type (wt) and the orf7 mutant was digested with ApaI, and probed with a 1.9 kb NcoI+BglII fragment (FIG. 21). Both the wt and the orf7 mutant gave two hybridizing ApaI bands. The mutant (FIG. 21 lane 3) gave a 1 kb and a 2.8 kb band whereas the wt (FIG. 21 lane 2) gave a 1 kb and a 1.8 kb band. The sizes of the hybridizing fragments are consistent with the replacement of the wild type orf7 with the neo-disrupted orf7.

5. ORF8 Mutant

A 2.9 kb BglII-EcoRI fragment carrying the disrupted ORF8 was subcloned from pCATL2orf8 into pIJ486.

Figure 22:
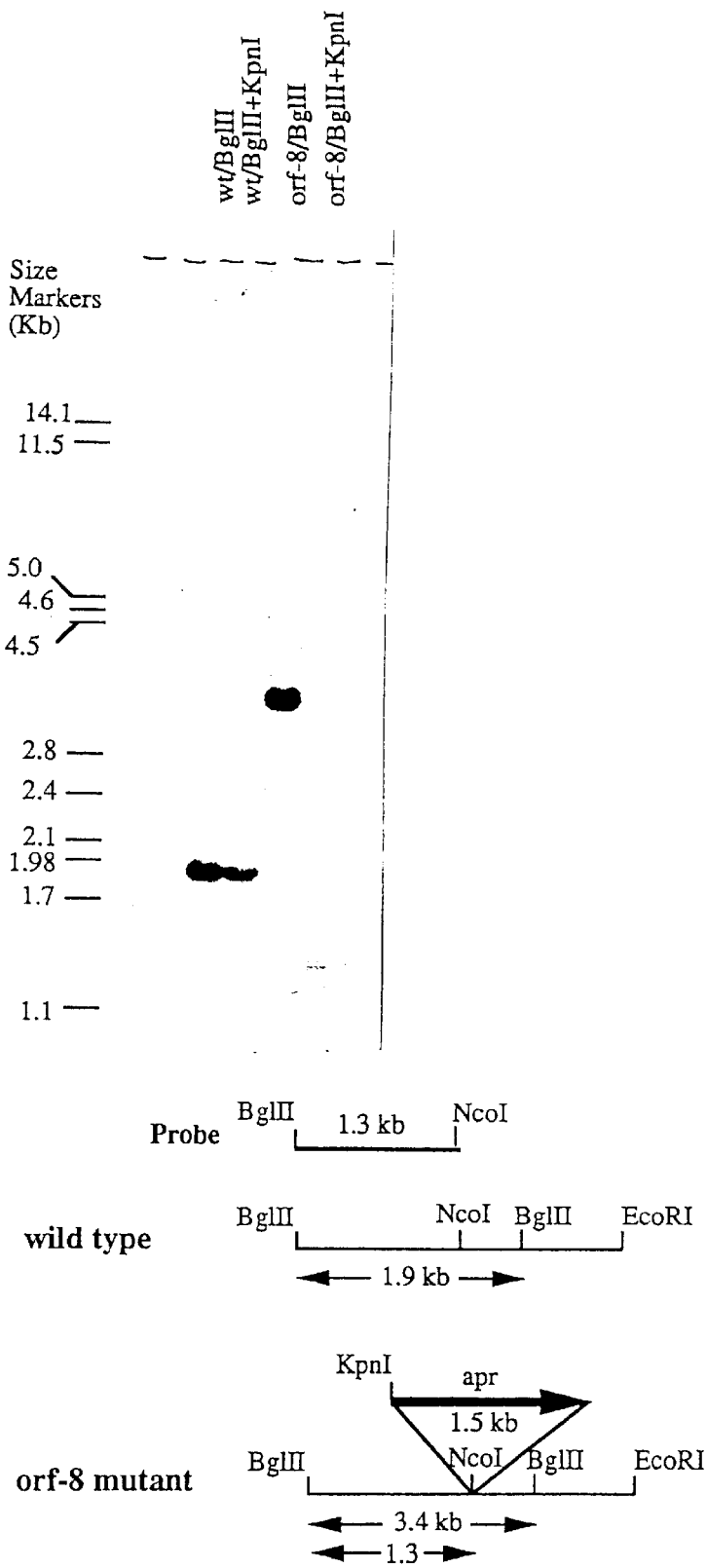
Figure 23:
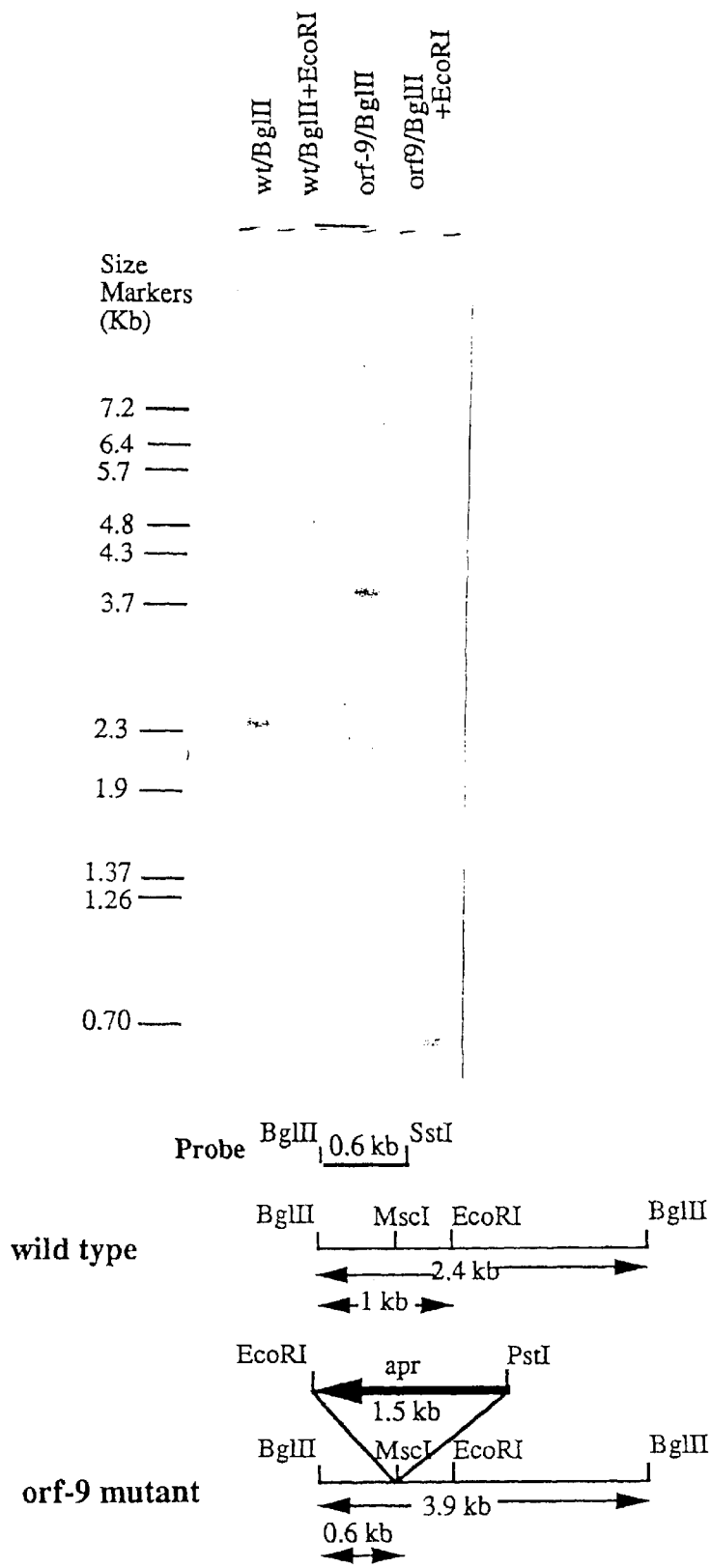
Figure 24A:
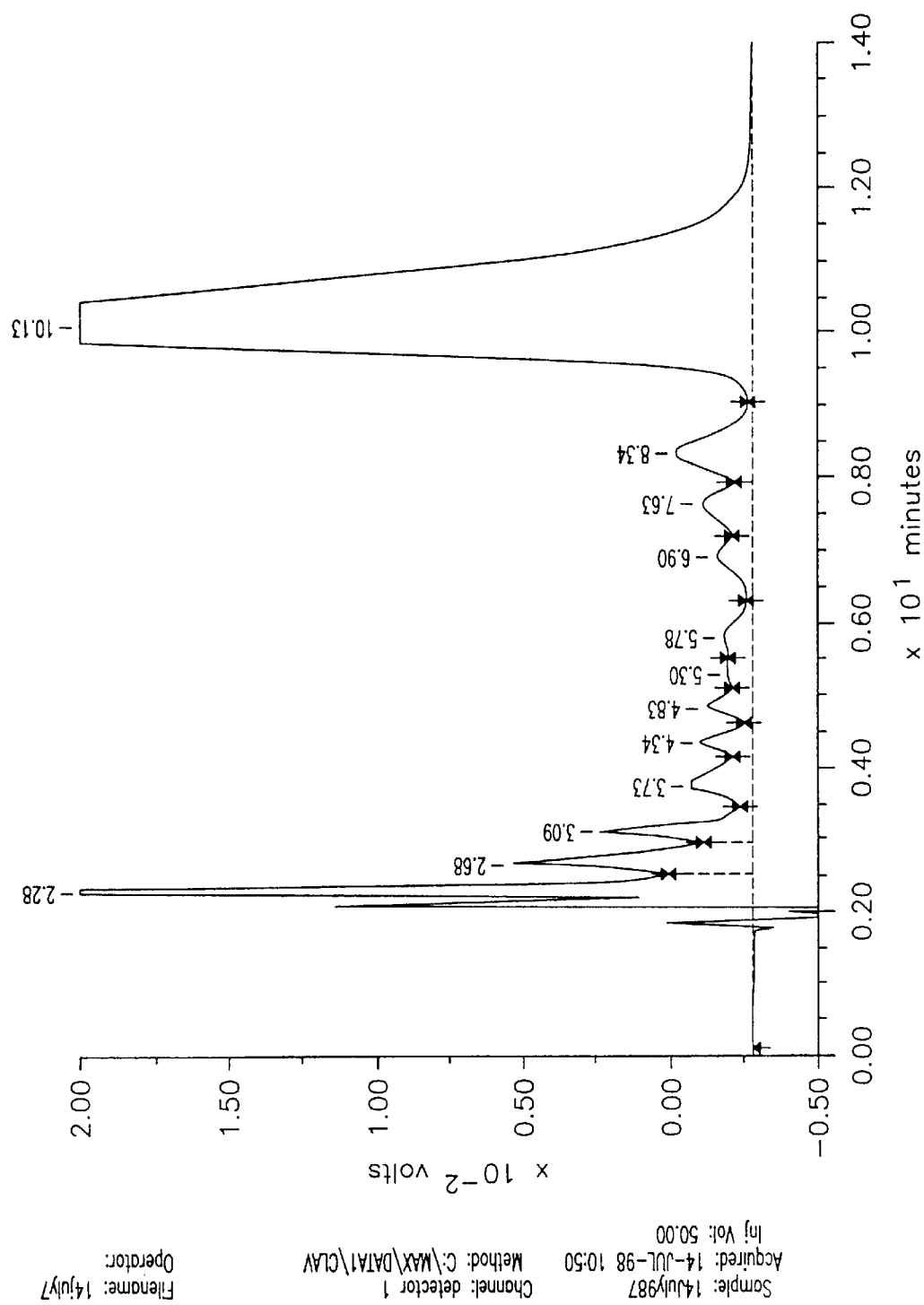
FIG. 24(A) and (B) show elution profiles of culture supernatants obtained from wild type (FIG. 24(A) or ORF7 gene disruption mutant (FIG. 24(B)). During this analysis, Clavulanic acid eluted with a retention time of approximately 10.13 min.
Figure 24B:
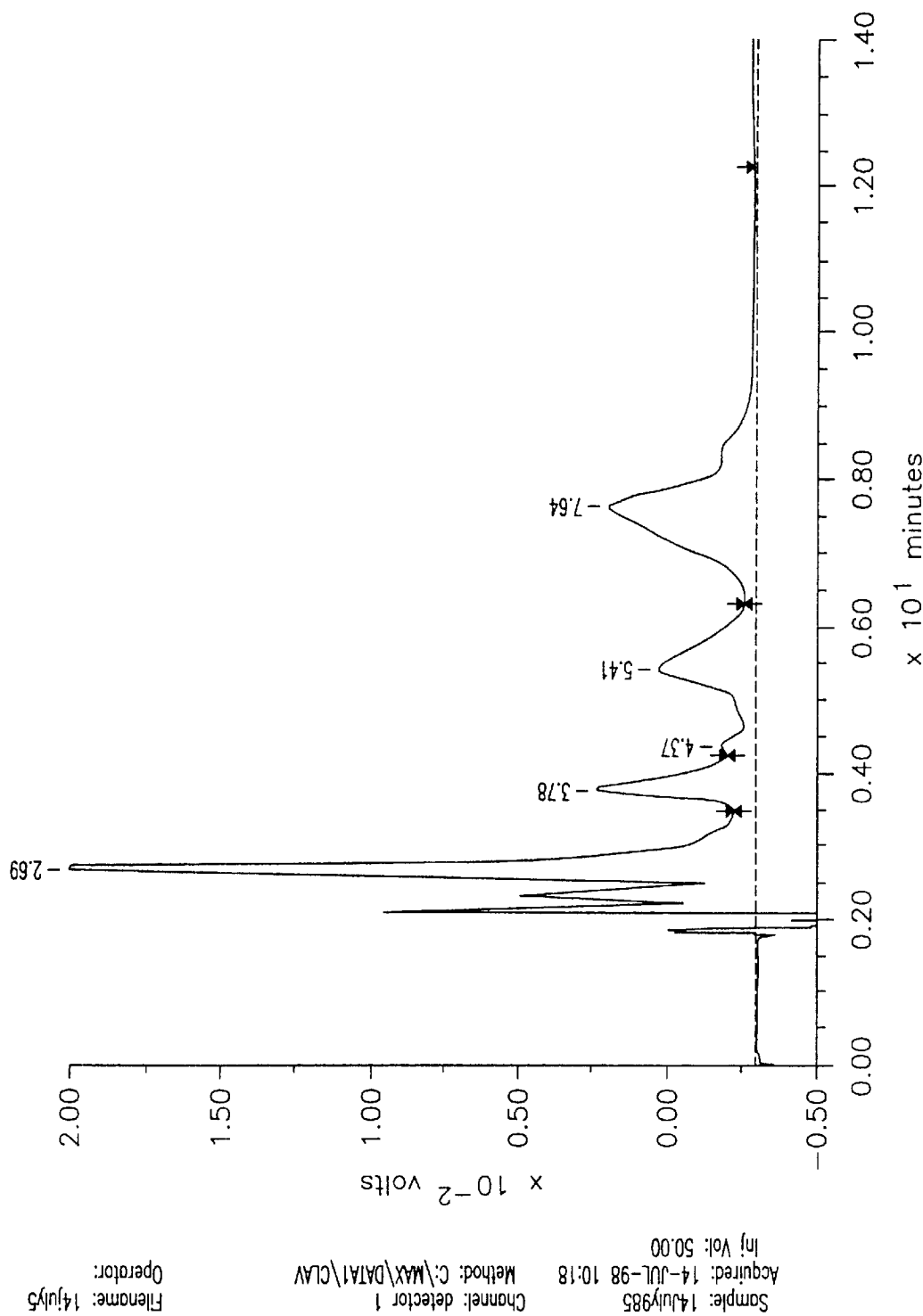
FIG. 24, high pressure liquid chromatography (HPLC) analysis of clavulanic acid in culture supernatants. Culture supernatants from 96 hour Starch-Asparagine medium-grown cultures of either wild type *S. clavuligerus*, or one of the gene disruption mutants were analyzed by HPLC.
FIGS. 24(C), (D) and (E), show elution profiles of clavulanic acid standard (FIG. 24(C)) and culture supernatants obtained from wild type (FIG. 24(D)) and ORF8 disruption mutant (FIG. 24(E)). During this analysis, clavulanic acid eluted with a retention time of approximately 9.1 min. Differences in retention times are due to the use of different columns between analysis of the samples. Similar HPLC profiles were seen for all of the other disruption mutants, including ORF2, ORF3, ORF6 or ORF9, and indicate that none of the mutants produced clavulanic acid under these culture conditions.
Figure 24C:
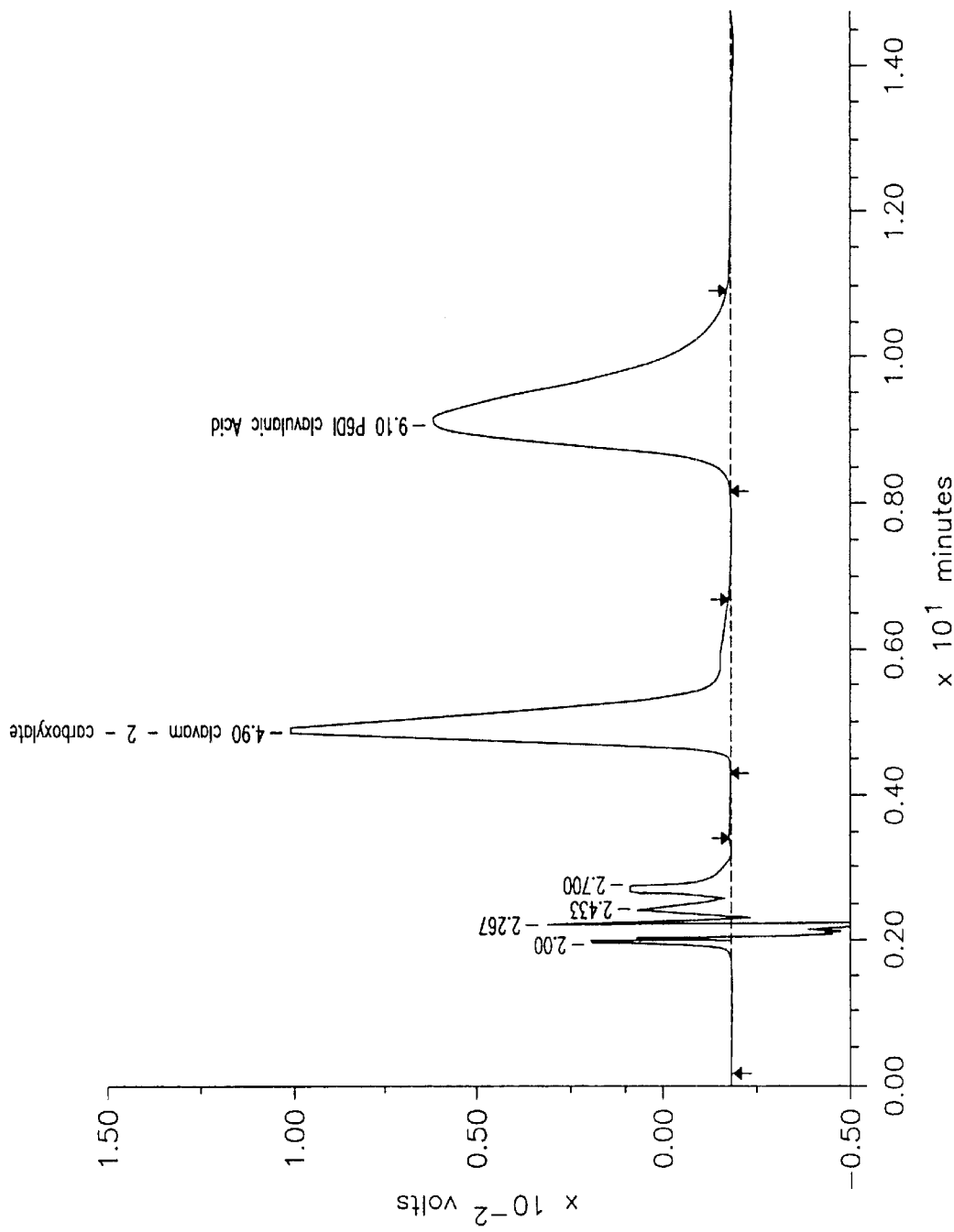
Figure 24D:
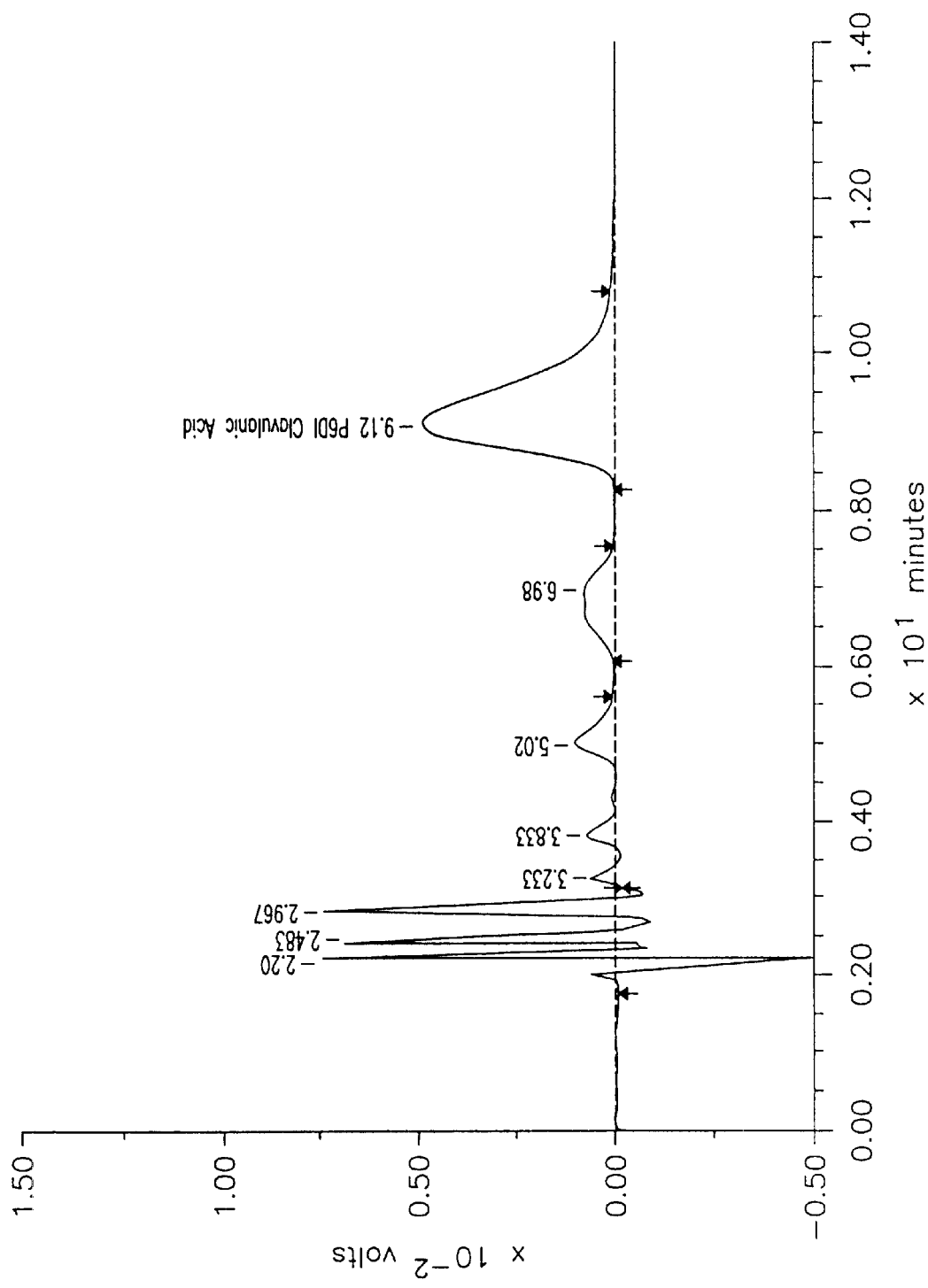
Figure 24E:
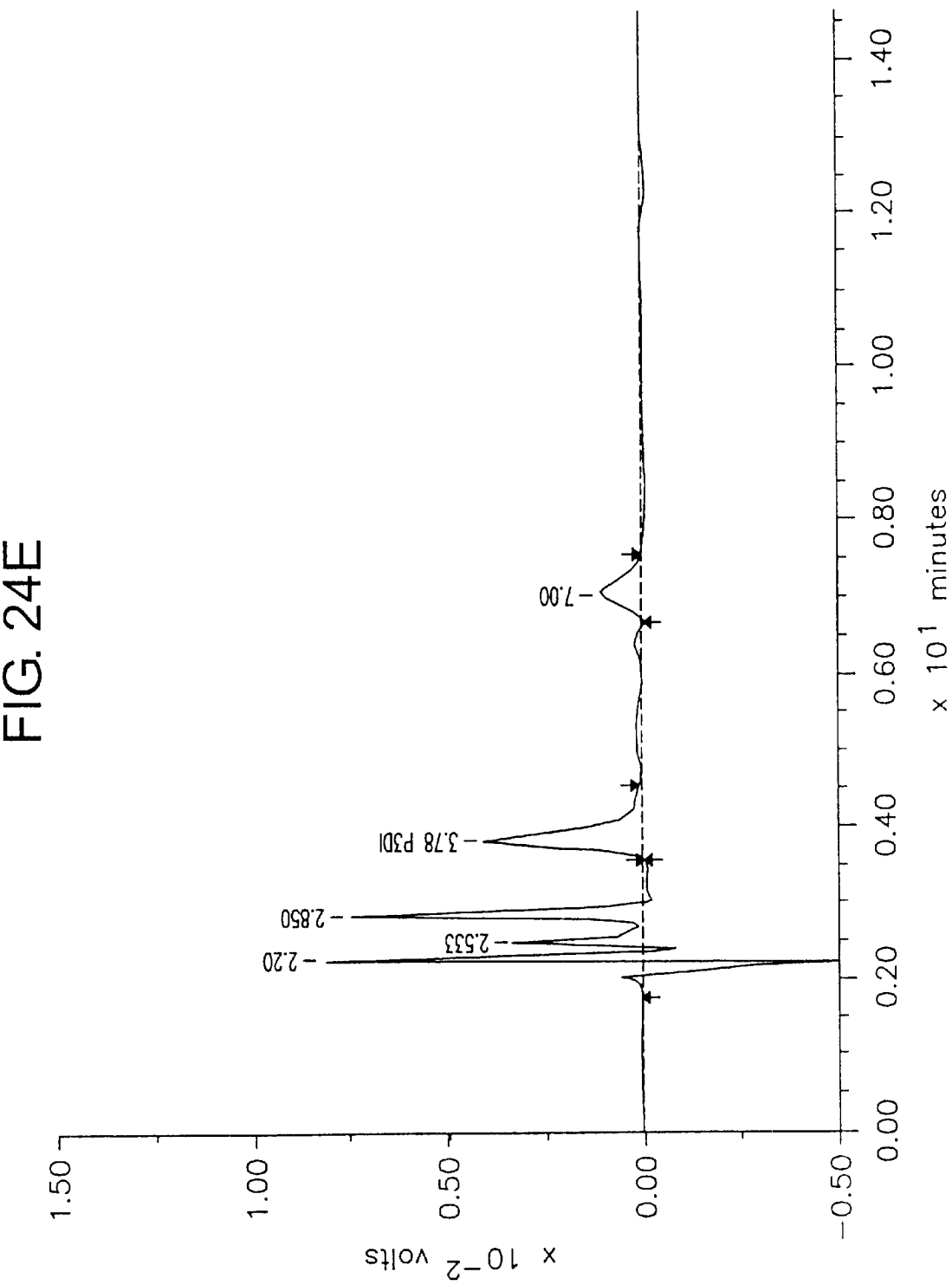

Genomic DNA from the wild type (wt) and from an ORF8 mutant was digested with BglII, and also with both BglII and KpnI, and probed with a 1.3 kb BglII-NcoI fragment (FIG. 22). In the BglII digests, the 1.9 kb hybridizing fragment present in the wild type has been replaced with a 3.4 kb fragment in the mutant, while in the BglII/KpnI digests, the 1.9-kb fragment has been replaced with a 1.3 kb fragment. The sizes of these hybridizing fragments are consistent with the replacement of the wild type ORF8 with the apr-disrupted ORF8.

6. ORF9 Mutant

The apr gene cassette was first cloned as an EcoRI-PstI fragment into the *E. coli* vector Pbluescript, and re-isolated as an EcoRV-SmaI fragment. This fragment was then inserted into the MscI site present in ORF9 contained within a 2.4 kb BglII fragment. Subsequently, the 4 kb fragment carrying the disrupted ORF9 was inserted into pIJ486.

Genomic DNA from the wild type (wt) and an ORF9 mutant was digested with BglII, and with both BglII and EcoRI, and probed with a 0.6-kb BglII-SstI fragment (FIG.

23). In the BglII digests, the 2.4 kb hybridizing fragment present in the wild type has been replaced with a 3.9 kb fragment in the mutant, while in the BglII-EcoRI digests, the 1-kb fragment has been replaced with a 0.6 kb fragment. In BglII-EcoRI digests of the ORF9 mutant genomic DNA another 3.3-kb EcoRI-BglII fragment might have been expected to hybridize to the probe, but failure to see this fragment can be attributed to the fact that the probe has only approximately 50 bp of sequence homologous to the expected fragment. Since the post-hybridization washes were carried out under stringent conditions this small amount of homology might not be sufficient to give a hybridizing band. Nevertheless, the sizes of other hybridizing fragments are consistent with the replacement of the wild type ORF9 with the apr disrupted ORF9.

The Effect of Mutations within the ORF's of the 12kb Fragment on Clavulanic Acid Synthesis 1. Bioassay The bioassay used to monitor clavulanic acid production in the gene disruption mutants has already been described above in Example 3 under the heading Antibiotic assay. The results are summarized in Table II below:

TABLE II

| Strain | No Penicillin | Penicillin G (1 $\mu$/ml) |
| --- | --- | --- |
| wild type | 0 mm | 28 mm |
| ORF2 | 0 mm | 0 mm |
| ORF3 | 0 mm | 0 mm |
| ORF6 | 0 mm | 0 mm |
| ORF7 | 0 mm | 0 mm |
| ORF8 | 0 mm | 0 mm |
| ORF9 | 0 mm | 0 mm |

If a zone of inhibition is obtained in the presence of penicillin but not in the absence thereof or if the size of the zones in the presence of penicillin is greater than the zones without penicillin, it is indicative of a β-lactamase inhibitory activity of clavulanic acid. The bioassay thus showed that transformants containing mutants with insertion in any one of the ORF2, ORF3, ORF6, ORF7, ORF8 or ORF9 failed to produce β-lactamase inhibitory activity of clavulanic acid, thus indicating that each of these ORFs are involved in the production of clavulanic acid.

2. HPLC Analysis

The amount of clavulanic acid produced by each transformant was also quantitated in each sample by HPLC. This assay was done to confirm the presence or absence of clavulanic acid production, within the cultured supernatants produced from each gene disruption mutant.

Culture Conditions for the Growth of Wild Type and the Mutants for Clavulanic Acid Production Spores of transformants containing insertional mutations within either ORF2, ORF3, ORF6, ORF8 or ORF9 were first inoculated into 20 mL Trypticase Soy Broth containing 1% starch, and the culture was grown shaking for 48 hours at 28° C. which served as a seed culture. Seed cultures were then used at 1% inoculum to inoculate 20 ml Starch Asparagine medium the composition of which has been described earlier (Paradkar and Jensen (1995), J Bacteriol Vol. 177, pp. 1307–1314), and the culture was grown in the same conditions as the seed culture. For ORF7 cultures, spores were inoculated into 25 ml Trypticase Soy broth containing 1% maltose to produce the seed culture, which was used at 2% inoculum to inoculate 25 ml Starch Asparagine medium as outlined above. Supernatants (0.1 mL) were obtained from 96 hour cultures, and derivatized with 25 $\mu$L of imidazole reagent. Subsequently, a 50 $\mu$L aliquot of the derivatized sample was analyzed by HPLC.

The high pressure liquid chromatography assay was conducted as described in Foulstone and Reading (1982, Antimicrob. Agents Chemother. 22:753–762).

Analysis was performed with a model M-45 pump, model 712 WISP automated sample injector, and model 480 variable-wavelength UV detector, all from Millipore Waters (Mississauga, Ontario, Canada). Samples (100 $\mu$l) were mixed with imidazole reagent (25 $\mu$l) and incubated at room temperature for 15 min to form imidazole-derivatized clavulanic acid. Derivatized samples (50 $\mu$l) were analyzed on a reverse-phase column ($\mu$Bondapak-C18) with an isocratic buffer system consisting of 0.1 M $KH_2PO_4$-6% methanol, PH 3.2 (adjusted with $H_3PO_4$).

The HPLC chromatograms of culture supernatants from transformants containing an insertional mutation within ORF2, ORF3, ORF6, ORF7, ORF8 or ORF9 and of the wild type were obtained. An example of these results is illustrated in FIG. 24, which represents HPLC profiles of wild type (FIG. 24(A) wild type control for ORF7, or FIG. 24(D), wild type control for ORF8) and ORF7 (FIG. 24(B), or the ORF8 (FIG. 24 (E)) insertion mutants. As can be seen from FIG. 24, clavulanic acid was detected in the supernatant of the wild type as a peak, at a retention time of approximately 10.13 minutes (FIG. 24(B)) or 9.1 minutes (FIG. 24(C)). An authentic sample of clavulanic acid, obtained just prior to the analysis of the ORF8 data also gave a retention time of approximately 9.1 minutes (FIG. 24(C)). The amount of clavulanic acid produced by the wild type was determined by integrating the clavulanic acid peak in the wild type supernatant. No clavulanic acid was detected in the supernatants of any of the insertion mutants.

All citations are incorporated herein by reference. The present invention is not limited to the features of the embodiments described herein, but includes all variations and modifications within the scope of the claims.

We claim:

1. An isolated DNA molecule consisting of the nucleotide sequence selected from the group consisting of SEQ ID NO:15, 16, 19, 20, 21, and 22.

2. The isolated DNA molecule of claim 1 consisting of the nucleotide sequence of SEQ ID NO:15.

3. The isolated DNA molecule of claim 1 consisting of the nucleotide sequence of SEQ ID NO:16.

4. The isolated DNA molecule of claim 1 consisting of the nucleotide sequence of SEQ ID NO:19.

5. The isolated DNA molecule of claim 1 consisting of the nucleotide sequence of SEQ ID NO:20.

6. The isolated DNA molecule of claim 1 consisting of the nucleotide sequence of SEQ ID NO:21.

7. The isolated DNA molecule of claim 1 consisting of the nucleotide sequence of SEQ ID NO:22.

8. An isolated DNA molecule consisting of a nucleotide sequence encoding the amino acid sequence selected from the group consisting of SEQ ID NO:4, 5, 8, 9, 10 and 11.

9. The isolated DNA molecule of claim 8 consisting of the nucleotide sequence encoding the amino acid sequence of SEQ ID NO:4.

10. The isolated DNA molecule of claim 8 consisting of the nucleotide sequence encoding the amino acid sequence of SEQ ID NO:5.

11. The isolated DNA molecule of claim 8 consisting of the nucleotide sequence encoding the amino acid sequence of SEQ ID NO:8.

12. The isolated DNA molecule of claim 8 consisting of the nucleotide sequence encoding the amino acid sequence of SEQ ID NO:9.

13. The isolated DNA molecule of claim 8 consisting of the nucleotide sequence encoding the amino acid sequence of SEQ ID NO:10.

14. The isolated DNA molecule of claim 8 consisting of the nucleotide sequence encoding the amino acid sequence of SEQ ID NO:11.

15. An isolated DNA molecule comprising the nucleotide sequence of SEQ ID NO: 15 and 16, and excluding other reading frames.

16. An isolated DNA molecule comprising the nucleotide sequence of SEQ ID NO: 19, 20, 21 and 22, and excluding other reading frames.

17. A recombinant vector comprising at least one of the isolated DNA molecules of claim 1.

18. A recombinant vector comprising at least one of the isolated DNA molecules of claim 8.

19. A host cell transformed with a recombinant vector in accordance with claim 17.

20. A host cell in accordance with claim 19 which is a Streptomycete.

21. A host cell in accordance with claim 20 which is a *S. lividans*.

22. A host cell in transformed with a recombinant vector in accordance with claim 18.

23. A host cell in accordance with claim 22 which is a Streptomycete.

24. A host cell in accordance with claim 23 which is a *S. lividans*.

25. An isolated DNA molecule consisting of the nucleotide sequence of nucleotides 2257–5522 of SEQ ID NO:1.

26. An isolated DNA molecule consisting of the nucleotide sequence of nucleotides 7936–13406 of SEQ ID NO:1.

27. The isolated DNA molecule consisting of the nucleotide sequence of nucleotides 1765–5694 of SEQ ID NO: 1.

28. The isolated DNA molecule consisting of the nucleotide sequence of nucleotides 7630–13809 of SEQ ID NO: 1.

29. The isolated DNA molecule consisting of the nucleotide sequence of nucleotides 2257–13406 of SEQ ID NO: 1.

* * * * *

SEQUENCE LISTING

<160> NUMBER OF SEQ ID NOS: 25

<210> SEQ ID NO 1
<211> LENGTH: 15120
<212> TYPE: DNA
<213> ORGANISM: Streptomyces clavuligerus

<400> SEQUENCE: 1
gcggaaccgg ccgcccctga gcggggcggc cgggaaggaa acgggccggt cgtcccctcg      60

```
ggaggggggcg gccggcccgt ccggtgcgcg cggtgggtgc ggcgcgggtc agccggccgc    120
gaggttgctg aggaacttcg cggcgacggg cccgcgtcg cgccgcccg acccgccgtc    180 ctccagcagg accgaccagg cgatgttccg gtcgccctgg tagccgatca tccaggcgtg    240
cgtcttcggc ggcttctcgg tgccgaactc ggcggtaccg gtcttggcgt gcggctgtcc    300
gccgaggccc cgcagggcgt cgccggcgcc gtcggtgacg gtcgaacgca tcatggaacg    360
cagcgagtcg acgatgcccg gggccatccg ggggcctgg tgcggcttct tgaccgcgtc    420
gggcaccagc acgggctgct tgaactcgcc ctgcttgacg gtggcggcga tggaggccat    480 caccagggc gacgcctcga ccctggcctg tccgatggtg gacgcggcct tgtcgttctc    540
gctgttggag acgggacgc tgccgtcgaa ggtggaggcg ccgacgtccc aggtgccgcc    600
gatgccgaag gcttcggcgg cctgcttcag gctggactcg gagagcttgc tgcgggagtt    660
gacgaagaac gtgttgcagg agtgggcgaa gctgtcccgg aaggtcgagc ccgcgggcag    720
cgtgaactgg tcctggttct cgaagctctg gccgttgaca tgggcgaact cgggcagtc    780 ggcccgctcc tccgggttca tccctgctg gagcagggcc gcggtggtga ccaccttgaa    840
ggtggagccg ggcgggtagc ggccctccag cgcgcggttc atgccggagg gcacgttcgc    900
ggcggccagg atgttgccgg tggcggggtc gacggcgacg atcgccgcgt tcttcttcga    960
gccctccagg gccgccgcgg cggcggactg gacccgcggg tcgatggtgg tcttcaccgg   1020
cttgccctcg gtgtccttga ggccggtgag cttcttgacc acctggccgg actcacggtc   1080
caggatcacg accgagcgcg ccgcgccgga ccgccggtg agctgcttgt cgtagcggga   1140
ctggaggccc gccgagccct tgccggtcct ggggtcgacc gcgccgatga tggaggcggc   1200
ctggaggaca ttgccgttgg cgtcgaggat gtccgcgcgc tcccgcgact tgagggcgag   1260
ggtctgcccc ggaaccatct gcggatggat catctcggtg ttgaacgcga ccttccactc   1320
cttgccgccg ccgacgacct tcgcggtgga gtcccaggcg tactccccgg ccccggggag   1380
ggtcattctg acgtgaacg gtatctccac ctcgccctcg gggttcttct ccccggtctt   1440
ggcggtgatc tccgtcttcg tcggcttgag gttggtcatg acggatttga tcagcgactc   1500
ggcgttgtcc ggggtgtccg tcagcccggc ggccgtcggg gcgtcgccct tctcccaggc   1560
gccgaggaag gtgtcgaact gtccggccgc cgcctccacc tcgggtcgc ccgaatcctt   1620 ctcgtcggca accaggctgg tgtaacccca atagccgagc cccaccgtca cggccagccc   1680
ggcgaccacc gcggtggccg cccggccacg ggagcggcgc ctgccctgcg gcgggtcatc   1740
gccatagttg tcggaatgcg tcatggggcc aggctatgcg ggcgccctct ttccctcctc   1800
cccggatacc gcgtttcagg acagtcaagg ggccgaacgg agggctggac cagccgctca   1860
gcggcccgtt cccaccccctt gggggaagc ggcacccgga aggtgaccga ggcaacatcc   1920
atggaaaggg gagcgaatcg gtcgccgagt tcaccgcgat tggagtagac ctctgaaagc   1980
gtgacagcgg ggagtagcga caaaacggtc agacccctga agggaattga ctgaattcca   2040
tcgattgatt gtgcgaatcc agggaagccg agcgaattga agtcatcggg ttcggcgacg   2100
gatgggcggt tcggccacgc accgtcactc ttcgtcccct cttcacaaga actcccgata   2160
cgtggagaag agagcgtgaa gagcgcgtcc ggtcagggtt gccgagaacc gtccaccatg   2220
acggagcctg gtactgacgg agtctggaga ccgctcatgt cccgtgtatc gaccgccccc   2280
agcggcaagc ctaccgccgc tcacgccctc ctgtcacggt tgcgtgatca cggtgtgggg   2340
aaggtgtttg gggttgtcgg ccgagaggcc gcgtcgattc tcttcgacga ggtcgagggg   2400
```

```
atcgacttcg ttctgacccg ccacgagttc accgcggqtg tcgccgctga tgtcctcgcg   2460
cggatcaccg gtcgccccca ggcgtgctgg gccaccctgg ccccggtat gaccaacctc    2520 tccaccggta tcgccacgtc cgtcctggac cgctcgccgg tcatcgcgct cgccgcgcag   2580
tcggagtcgc acgacatctt cccgaacgac acccaccagt gcctggactc ggtggcgatc   2640
gtcgccccga tgtccaagta cgccgtggag ctccagcggc ccacgagat caccgacctc    2700 gtcgactccg ccgtgaacgc ggccatgacc gagccggtcg ggccctcctt catctccctc   2760
ccggtggacc tgctcggctc ctccgagggc atcgacacca ccgtcccaa cccgccggcg    2820 aacaccccgg cgaaaccggt cggcgtcgtc gccgacggct ggcagaaggc cgccgaccag   2880
gccgccgccc tgctcgccga ggccaagcac ccggtgctcg tcgtcggagc ggccgcgatc   2940
cgctcgggcg ccgtcccggc gatccgcgcc ctggccgagc gcctgaacat cccggtcatc   3000
acgacctaca tcgccaaggg tgtcctgccg gtcggccacg agctgaacta cggcgccgtc   3060
accggctaca tggacggcat cctcaacttc ccggcgctcc agaccatgtt cgccccggtg   3120
gacctcgtcc tcaccgtcgg ctacgactac gccgaggacc tgcgcccgtc catgtggcag   3180
aagggcatcg agaagaagac cgtccgtatc tccccgacgg tcaacccgat ccccgggtc    3240 taccggcccg acgtcgacgt cgtcaccgac gtcctcgcct tcgtggagca cttcgagacc   3300
gcgaccgcct ccttcgggc caagcagcgc cacgacatca gccgctgcg cgcccggatc     3360 gcggagttcc tggccgaccc ggagacctac gaggacggca tgcgcgtcca ccaggtcatc   3420
gactccatga acaccgtcat ggaggaggcc gccgagcccg gcgagggcac gatcgtctcc   3480
gacatcggct tcttccgtca ctacggtgtg ctcttcgccc gcgccgacca gcccttcggc   3540
ttcctcacct cggcgggctg ctccagcttc ggctacggca tccccgccgc catcggcgcc   3600
cagatggccc gccggacca gccgaccttc ctcatcgcgg gtgacggcgg cttccactcc    3660
aacagctccg acctggagac catcgcccgg ctcaacctgc cgatcgtgac cgtcgtcgtc   3720
aacaacgaca ccaacggcct gatcgagctg taccagaaca tcggtcacca ccgcagccac   3780
gacccggcgt tcaagttcgg cggcgtcgac ttcgtcgcgc tcgccgaggc caacggtgtc   3840
gacgccaccc gcgccaccaa ccgcgaggag ctgctcgcgg ccctgcgcaa gggtgccgag   3900
ctgggtcgtc cgttcctcat cgaggtcccg gtcaactacg acttccagcc gggcggcttc   3960
ggcgccctga gcatctgatc atgggggcac cggttcttcc ggctgccttc gggttcctgg   4020
cctccgcccg aacgggcggg ggccgggccc ccggccggt cttcgcgacc cggggcagcc    4080
acaccgacat cgacacgccc caggggagc gctcgctcgc ggcgaccctg gtgcacgccc     4140
cctcggtcgc gcccgaccgc gcggtggcgc gctccctcac cggcgcgccc accaccgcgg   4200
tgctcgccgg tgagatctac aaccgggacg aactcctctc cgtgctgccc gccggacccg   4260
cgccggaggg ggacgcggag ctggtcctgc ggctgctgga acgctatgac ctgcatgcct   4320
tccggctggt gaacgggcgc ttcgcgaccg tggtgcggac cggggaccgg tcctgctcg    4380 ccaccgacca cgccggttcg gtgccgctgt acacctgtgt ggcgccgggc gaggtccggg   4440
cgtccaccga ggccaaggcg ctcgccgcgc accgcgaccc gaagggcttc ccgctcgcgg   4500
acgcccgccg ggtcgccggt ctgaccggtg tctaccaggt gcccgcgggc gccgtgatgg   4560
acatcgacct cggctcgggc accgccgtca cccaccgcac ctggaccccg ggcctctccc   4620
gccgcatcct gccggagggc gaggccgtcg cggccgtgcg ggccgcgctg gagaaggccg   4680
tcgcccagcg ggtcaccccc ggcgacaccc cgttggtggt gctctccggc ggaatcgact   4740 cctccgggt cgcggcctgt gcgcaccggg cggccgggga actggacacg gtgtccatgg    4800
```

-continued

```
gcaccgacac gtccaacgag ttccgcgagg cccgggcggt cgtcgaccat ctgcgcaccc   4860
ggcaccggga gatcaccatc ccgaccaccg agctgctggc gcagctcccg tacgcggtgt   4920
gggcctccga gtcggtggac ccggacatca tcgagtacct gctcccctg acagcgctct    4980
accgggcgct cgacgggccg gagcgccgca tcctcaccgg gtacgcgcg gacatccccc    5040
tcggggcat gcaccgcgag gaccggctgc ccgcgctgga caccgttctc gcgcacgaca    5100
tggccacctt cgacgggctg aacgagatgt ccccggtgct gtccacgctg gcggggcact   5160
ggaccaccca cccgtactgg gaccgggagg tcctcgatct gctggtctcg ctggaggccg   5220
ggctcaagcg gcggcacggc cgggacaagt gggtgctgcg cgccgcgatg gccgacgccc   5280
tcccggcgga gaccgtcaac cggcccaagc tgggcgtcca cgagggctcg ggcaccacgt   5340
cctcgttctc ccggctgctg ctggaccacg tgtcgccga ggaccgcgtc cacgaggcga    5400
agcggcaggt ggtgcgcgag ctgttcgatc tcacggtcgg gggcggacgg cacccctccg   5460
aggtggacac cgacgatgtg gtgcgctccg tggccgaccg gaccgcgcgg ggggcggcct   5520
agtcccgcca cggggagccc gccggacgcc ggacccgcgc gggacccgta cccggggccg   5580
cccgcggact ccggcgcacc ggcacccctg tcccccaccc gttgacgacc gtcggccctc   5640
ggccctcgcg gcccctgacg accgtcgccc gattcccagg agggagctga aagcgtggag   5700
cgcatcgact cgcacgtttc accccgctac gcacagatcc ccaccttcat gcgcctgccg   5760
cacgatcccc agccccgcgg ctatgacgtg gtggtcatcg agccccta cgacggggc     5820
accagctacc gtcccggcgc ccggttcggc ccccaggcca tccgcagtga gtcgggcctc   5880
atccacggtg tcggcatcga ccggggcccc ggcacgttcg acctgatcaa ctgtgtcgac   5940
gccggggaca tcaatctgac gccgttcgac atgaacatcg cgatcgacac ggcgcagagc   6000
catctgtcgg gcctgctgaa ggccaacgcc gcctttctga tgatcggcgg cgaccactcg   6060
ctgacggtgg ccgccctgcg cgcggtcgcg gagcagcacg gcccgctcgc cgtggtgcac   6120
ctggacgcgc actccgacac caacccggcc ttctacgggg gccggtacca ccacggcacc   6180
cccttccggc acgggatcga cgagaagctg atcgacccgg cggcgatggt ccagatcggc   6240
atccggggcc acaacccgaa gccggactcg ctcgactacg cccggggcca cggcgtccgg   6300
gtggtcacgg cggacgagtt cggcgagctg ggggtgggcg ggaccgccga cctcatccgc   6360
gagaaggtcg gccagcggcc cgtgtacgtc tcggtcgaca tcgacgtggt cgaccccgcc   6420
ttcgcccccg gtacgggcac gcccgcgccg ggcgggctcc tctcgcgcga ggtgctggcg   6480
ctgctgcgct gcgtgggtga cctgaagccg gtcggcttcg acgtgatgga ggtgtcaccc   6540
ctctacgacc acgcgggat cacttcgatc ctggccacgg agatcggtgc ggaactgctc   6600
taccagtacg cccgagccca cagaacccag ttgtgaagga cacatcgtgt catggcctct   6660
ccgatagttg actgcacccc gtaccgcgac gagctgctcg cgctcgcctc cgagcttccc   6720
gaggtgccgc gcgcggacct ccatggcttc ctcgacgagg cgaagacgct ggccgcccgt   6780
ctccccggagg ggctggccgc cgctctcgac accttcaacg ccgtgggcag cgaggacggt   6840
tatctgctgc tgcgcgggct gcccgtcgac gacagcgagc tgcccgagac gccgacctcc   6900
accccggccc cgctggaccg caagcggctg gtgatggagg ccatgctcgc gctggccggc   6960
cgccggctcg gtctgcacac ggggtaccag gagctgcgct cgggcacggt ctaccacgac   7020
gtgtacccgt cgcccggcgc gcactacctg tcctcggaga cctccgagac gctgctggag   7080
ttccacacgg agatggcgta ccacatcctc cagccgaact acgtcatgct ggcctgctcc   7140
```

```
cgcgcggacc acgagaaccg ggcggagacg ctggtcggct cggtccgcaa ggcgctgccc    7200
ctgctggacg agaagacccg ggcccgtctc ttcgaccgca aggtgccctg ctgcgtggac    7260
gtggccttcc gcggcggggt cgacgacccg ggcgcgatcg ccaacgtcaa gccgctctac    7320
ggggacgcga acgacccgtt cctcgggtac gaccgcgagc tgctggcgcc ggaggacccc    7380
gcggacaagg aggccgtcgc ccatctgtcc caggcgctcg acgatgtgac cgtcggggtg    7440
aagctcgtcc ccggtgacgt cctcatcatc gacaacttcc gcaccacgca cgcgcggacg    7500
ccgttctcgc cccgctggga cgggaaggac cgctggctgc accgcgtcta catccgcacc    7560
gaccgcaatg acagctctct cggcggcgag cgcgcgggcg acaccatctc gttctcgccg    7620
cgccgctgag cccggctccc cgaggccctg gccccggcg ccggaaccgg ctcccggtcc    7680
tgcccctca cccgccgcgc gggtgagggg gcaggcccct tgtgccggg tgccgtgcgt    7740
cctgcgaggg tgccggggcg gggggacgg cggaggtgcc cggcggccgg gtgccgtgcg    7800
ccgcccgtgg gtgctgtaca gcactccgtg tgccgtgcgc caccccgtgc ataaatttgc    7860
cactctatgg gaataatgc agagtgcgac gggtgaggcc gtcgccgtgc cctttccgtg    7920
acaggagacg ctgacatgtc cgacagcaca ccgaagacgc cccggggatt cgtggtgcac    7980
acggcgccgg tgggcctggc cgacgacggc cgcgacgact tcaccgtcct cgcctccacc    8040
gccccggcca ccgtgagcgc cgtcttcacc cgctcccgct tcgccgggcc gagcgtcgtg    8100
ctgtgccggg aggcggtggc cgacgggcag gcgcgcggtg tggtggtgct ggcccgcaac    8160
gcgaatgtcg cgaccggcct ggagggcgag gagaacgcgc gcgaggtgcg cgaggccgtc    8220
gccccgggccc tcgggctgcc ggagggcgag atgctgatcg cctccaccgg ggtgatcggc    8280
cggcagtacc cgatggagag catccgggag cacctcaaga cgctggagtg gccccgccggg    8340
gagggcggct tcgaccgcgc ggcccgcgcc atcatgacga ccgacacccg gcccaaggag    8400
gtccgggtca gcgtcggcgg ggcgaccctc gtgggcatcg ccaagggcgt cggcatgctg    8460
gagcccgaca tggcgacgct gctgaccttc ttcgccacgg acgcccggct ggacccggcc    8520
gagcaggacc gcctcttccg ccgggtcatg gaccgcacct tcaacgcggt cagcatcgac    8580
accgacacct ccaccagcga cacggcggtg ctgttcgcca acggcctggc gggcgaggtc    8640
gacgccgggg agttcgagga ggcgctgcac acggcggcgc tggccctggt caaggacatc    8700
gcgagcgacg gcgagggcgc ggccaagctg atcgaggtcc aggtcaccgg cgcccgcgac    8760
gacgcccagg ccaagcgggt cggcaagacc gtcgtcaact cccgttggt gaagaccgcc    8820
gtgcacggct gcgaccccaa ctggggccgg gtcgccatgg cgatcggcaa gtgctcggac    8880
gacaccgaca tcgaccagga gcgggtgacg atccgcttcg gcgaggtcga ggtctatccg    8940
ccgaaggccc ggggcgacca ggccgacgac gcgctgcggg ccgccgtcgc ggagcatctg    9000
cggggcgacg aggtggtcat cgggatcgac ctcgccatcg cggacgggggc cttcaccgtc    9060
tacggctgcg acctcaccga gggctatgtc cggctgaact cggagtacac cacctgatcc    9120
ccggacaggg aacgggccgc cgccccgttc cctgtccgct cccgtcccgt gtggttatac    9180
cgaccgttcc ccggctatgc gcacgggacg gagcggcccc cgccgggccc cgcccggccg    9240
cacgatgagg ggcgatgcaa ggtgacgagg gcaggaggga catggagacc actcggtcga    9300
cgaccgcgga cgagggcttc gacgccgggg tacggggagt ggtcgcgccg accgacgccc    9360
cggggcggac gctgcggctg gtccgcacgg acgacttcga ctcgctcgac cccggcaaca    9420
cgtactacgc ctacacctgg aacttcctcc ggctcatcgg ccggacgctg gtcaccttcg    9480
acaccgcgcc gggcaaggcg ggccagcggc tcgtgcccga cctcgccgag tcgctgggcg    9540
```

-continued

```
agtcctccga ggacggccgg gtctggacct accggctgcg cgagggcctg cgctacgagg   9600
acggcacgcc ggtcgtctcg gccgacatca agcacgccat cgcccgcagc aactacggca   9660
ccgatgtcct gggcgccggt ccgacctact tccgccacct cctgggcacc gagtacggcg   9720
gcccctggcg ggagccggac gccgacggac cggtgacgct ggagacccccg gacgagcgga   9780
cgctggtctt ccgctgcgg gagccgttcg cggggatgga tctgctggcg accatgccgt   9840
ccaccacccc cgtgccgcgc gaccgggaca ccggcgccga gtaccggctg cggcccgtgg   9900
cgaccggccc gtaccggatc gtctcgtaca cccgggggcga gctggccgtc ctggagccca   9960
atccgcactg ggaccccgag accgacccgg tgcgcgtcca gcgcgcctcc cggatcgagg  10020
tgcacctcgg caaggacccg cacgaggtgg accgcatgct gctggcgggc gaggcccatg  10080
tggacctcgc gggcttcggt gtgcagcccg cggcccagga gcgcatcctc gccgagccgg  10140
agctgcgcgc gcacgcggac aacccgctga ccggcttcac ctggatctac tgcctgtcga  10200
gccggatcgc cccgttcgac aatgtgcact gccggcgggc cgtgcagttc gccaccgaca  10260
aagcggccat gcaggaggcg tacgcgggcg cggtgggcgg cgacatcgcg accaccctgc  10320
tgcccccgac cctcgacggc tacaagcact tcgaccgcta cccggtcggc cccgagggca  10380
ccggcgacct ggaggccgcc cgcgccgagc tgaagctggc cgggatgccc gacggcttcc  10440
gcaccaggat cgccgcccgc aaggaccggc tcaaggagta ccgggccgcc gaggcgctgg  10500
ccgccgggct cgcccgggtc ggcatcgagg cggaggtgct ggacttcccg tcgggcgact  10560
acttcgaccg ctacggcggc tgcccggagt atctgcgcga gcacgggatc gggatcatca  10620
tgttcggctg gggcgccgac ttccccgacg gatacggctt cctccagcag atcaccgacg  10680
ggcgcgcgat caaggagcgc ggcaaccaga acatgggcga gctggacgac ccggagatca  10740
acgcgctgct ggacgagggg gcgcagtgcg ccgaccggc gcggcgcgcg gagatctggc  10800
accgcatcga ccagctcacg atggaccacg cggtcatcgt tccgtatctg tacccgcggt  10860
ccctgctcta ccggcacccg gacacccgca acgccttcgt caccggctcc ttcgggatgt  10920
acgactacgt ggcgctcggc gcgaagtgag cacgggtccg gccccgggga ccgtatgtcc  10980
cggggccgga ccccgcccgt tccccgcccg gtccggtccg gacccggtcg cggcccgctc  11040
agccggacat ccgggcccccg ccgcgacccc gcgccggat cggccagtgg ccctgcgcca  11100
ggggccgttc cacgctgcgg caggcgagag cggcctcgcg gaactccgcc tcgtacagcg  11160
cgagctggcg caggaactgc cgggtcgggc cggtcaggct ggtccccgc gggctgcgca  11220
gcagcagccg ggcgccgagg gactgctcca gccggtgaat ccggcgggtg agcgccgact  11280
ggctgatcga cagcaccgcc gcggcccggt tgatgctgcc gtgccgggcc acggcctgga  11340
gcagatggag atcgtccaca tccagtttgc ggccctcggc ctggccgggc acggagccct  11400
ggtcgggtcc cgccccgaag cggcgggcgt ccgcgccggt gcgctccgcg taccactgcg  11460
cccaccaggg ctcgtccagc aggtcgcggt ggtgttcggc gaagcgccgg agctggacct  11520
cggcgatcag cgcggccagc cgtccgcca gcgcccgggg cacgatggtg gggtcgacga  11580
gcagactcgt ggtgcggcgc gggcgctccg ccagggagcg gcgcaccagc gagggtcct  11640
gcaccgccgg gtgggtgggc gagccgagac ctatcgcgtc cccgcggcgc aggatgcccc  11700
gggcaaccga tgcccccgtg atgtggagcc gggtgggcgc ggtgagcccg ccagctgga  11760
agacacgtgt caccaggatc tccgagccgg gtccgtctc ggacacccag gtctcgtccc  11820
gcagatcggc gagcgagacc tcccgccggg cggccagcgg atggtcccgg ggcaggatca  11880
```

-continued

```
cccacagcgg gtcgtccagc acctcacagg tgcgcacgga ccgctccagg ctgtgccggg    11940
gggactggag gctccaggtg taggccgcgt ccacctggta gcccgccagt tgggcggcga    12000
cctggtgcgg ggcctcgtgc cggaccgaca gcagcaggtc cagcgaggcc gccgcgtcct    12060
ccaccacctc gtcgagcagg ggttccgtgg agaccagcga cagcacctcc ggggcgtcca    12120
cggcctcgga gccatggccg aagatatgcg tccgcgcggc caggtcgacc tggtggaaga    12180
accgccgccc ggcgacgagg atgcgggagc ccgcggtggt cagccgggcc gtgtggcggc    12240
tgcgcagggt cagcgggagg ccgacgatcc ggtccagccg gtcgagtctg cgctccacgg    12300
tgccgtgccg gacacccgtc cgccgggcca cttccatgag gtctccgcag tgtcccaccg    12360
cgtccagtaa agacagatcg catcggctga caccagcaga cgtcggttct gacccgagag    12420
acaatgtcgg ttccctttc cgtcaaggac tgtaccgctg aattgtccga agtggctctt    12480
gaattgcttc ggaatcgatc ctaggcagcc ccgctcttcg gattctcctc gccgggaagc    12540
ggaacgcgcc cggccggatg gcgggcgcgc tccgggcgcc gtcccgggaa cggggacggg    12600
ggcacggcac ggccggccac ccggtccggg cgcgcggcgt ggacctggtc ggcggacggg    12660
tgtcagacct ggtcggtggg gcgtatgaag atctcgtgga cggtcgcgtg gtgcggcgcg    12720 gtcacgcgcgt agcggaccgc ctccgcgatg tcctgggcct ggagcttgcg gatctggctg    12780
atccgctgct cgtacatctc cttggtggcg gtgtgggtga tgtggccgcg cagctccgtg    12840
tcggtggtgc ccggctcgat gacgacgacc cgcaccccgc gctcggtgac ctcctggcgc    12900
agcgtctcgc tgaacgcgtt cacaccgaac ttcgtggcct ggtagacggc cgcgttgcgg    12960
acgttcaccc ggcccgcgat cgaggacatc tgcaccacgg tgcccttgct gcgcagcaga    13020
tggggaaggg ccgcccgggt catgtacatc aggcccagga gattggtgtc gatcatccgg    13080
gtccagtcgg tggtgtcggc gtcctccacc gggccgagca gcatgatccc ggcgttgttg    13140
acgaggatgt cgaggccgcc cagcgcctcg acggtggagg cgacgcggc gtccacccc    13200 tgccggtcgg cgacgtcgag ttcgaggaca tggaccttcg ccccggcggc ggtcagctcg    13260
tcacccaggg cgcgcagctt ctcgaccgg cgcgcggcga tggccacggc ggcgccctcg    13320
gcggccaggg cgcgggccgt ggcctcgccg atgcccgagc tcgcgcccgt gatgagcgcg    13380
actttcccct ggagtgcgga tggcatcatt tcctccacat ggtgctgcga tcgtggtgag    13440
cgtatgaaga aggggtgaga cctgccgtgc cggggcgggt tccgtacgcc ggaccgttgc    13500
ggtgggcacg gccgaccggg tacgatggcg cgcagttccc cggggagttc ccggggaatg    13560
gtgaataccg cggcgctctc cgatggtctt cggaggacac ccggggattc accgggaatc    13620
agcggccgga gttctccccg tccacggcag acgctatcag cgtcgcattc cccggtgaat    13680
tcccttcggt ggaccgggtt atgactgttt ccgccgggtt atgcgcgccg ccccggcgga    13740
ccggccaccc gccggggggc tgcggcagat tgggcgccac gacatggcgc gagcagcgat    13800
cggcggtgga tgatgaacga ggcagcgcct cagtccgacc aggtggcacc ggcgtatccg    13860
atgcaccggg tctgcccggt cgacccgccc cgcaactgg ccgggctgcg gtcccagaag    13920
gccgcgagcc gggtgacgct gtgggacggc agccaggtgt ggctggtgac ctcgcacgcc    13980
ggggcccggg ccgtcctggg cgaccgccgc ttcaccgcgg tgacgagcgc gcccggcttc    14040
ccgatgctga cccgcacctc ccaactggtg cgcgccaacc cggagtcggc gtcgttcatc    14100
cgcatggacg acccgcagca ctcccggctg cgctcgatgc tcacccggga cttcctggcc    14160
cgccgcgccg aggcgctgcg ccccgcgtg cgggagctgc tggacgagat cctgggcggg    14220
ctggtgaagg gggagcggcc ggtcgacctg gtcgccggac tgacgatccc ggtgccctcg    14280
```

```
cgggtcatca ccctgctctt cggcgccggt gacgaccgcc gggagttcat cgaggaccgc   14340
agcgcggtcc tcatcgaccg cggctacacc ccggagcagg tcgccaaggc ccgggacgaa   14400
ctcgacggct atctgcggga gctggtcgag gagcggatcg agaacccggg caccgacctg   14460
atcagccggc tcgtcatcga ccaggtgcgg ccggggcatc tgcgggtcga ggagatggtc   14520
ccgatgtgcc ggctgctgct ggtggccggt cacggcacca ccaccagcca ggcgagcctg   14580
agcctgctca gcctgctcac cgaccccggag ctggccgggc gcctcaccga ggacccggcc   14640
ctgctgccca aggcggtcga ggagctgctg cgcttccact ccatcgtgca gaacgggctg   14700
gcccgtgccg cggtggagga cgtccagctc gacgatgtgc tcatccgggc gggcgagggc   14760
gtggtgctgt cgctgtcggc gggcaaccgg gacgagacgt tcttccccga cccggaccgg   14820
gtggacgtgg accgcgacgc ccgccgccat ctcgccttcg gccacggcat gcaccagtgc   14880
ctgggccagt ggctggcccg ggtggagctg gaggagatcc tcgccgcggt gctgcgctgg   14940
atgcccggtg cccggctcgc ggtgcccttc gaggagctgg acttccgtca tgaggtgtcc   15000
agttacggcc tcggcgccct cccggtgacc tggtgagcgg cgtggagcgg ctgaccgtcg   15060
tcctcgacgc gtcggcctgc tgcgcgatgg ggcgctgcgc ggccacggcc ccgagatct    15120
```

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:PRIMER

<400> SEQUENCE: 2
tacgcccaga tccccacctt catg     24

<210> SEQ ID NO 3
<211> LENGTH: 552
<212> TYPE: PRT
<213> ORGANISM: Streptomyces clavuligerus

<400> SEQUENCE: 3

```
Met Thr His Ser Asp Asn Tyr Gly Asp Asp Pro Pro Gln Gly Arg Arg
  1               5                  10                  15

Arg Ser Arg Gly Arg Ala Ala Thr Ala Val Val Ala Gly Leu Ala Val
                 20                  25                  30

Thr Val Gly Leu Gly Tyr Trp Gly Tyr Thr Ser Leu Val Ala Asp Glu
             35                  40                  45

Lys Asp Ser Gly Asp Pro Glu Val Glu Ala Ala Gly Gln Phe Asp
     50                  55                  60

Thr Phe Leu Gly Ala Trp Glu Lys Gly Asp Ala Pro Thr Ala Ala Gly
 65                  70                  75                  80

Leu Thr Asp Thr Pro Asp Asn Ala Glu Ser Leu Ile Lys Ser Val Met
                 85                  90                  95

Thr Asn Leu Lys Pro Thr Lys Thr Glu Ile Thr Ala Lys Thr Gly Glu
            100                 105                 110

Lys Asn Pro Glu Gly Glu Val Glu Ile Pro Phe Thr Val Arg Met Thr
            115                 120                 125

Leu Pro Gly Ala Gly Glu Tyr Ala Trp Asp Ser Thr Ala Lys Val Val
        130                 135                 140

Gly Gly Gly Lys Glu Trp Lys Val Ala Phe Asn Thr Glu Met Ile His
145                 150                 155                 160
```

```
Pro Gln Met Val Pro Gly Gln Thr Leu Ala Leu Lys Ser Arg Glu Arg
            165                 170                 175
Ala Asp Ile Leu Asp Ala Asn Gly Asn Val Leu Gln Ala Ala Ser Ile
            180                 185                 190
Ile Gly Ala Val Asp Pro Arg Thr Gly Lys Gly Ser Ala Gly Leu Gln
            195                 200                 205
Ser Arg Tyr Asp Lys Gln Leu Thr Gly Ser Gly Ala Ala Arg Ser
210                 215                 220
Val Val Ile Leu Asp Arg Glu Ser Gly Gln Val Val Lys Lys Leu Thr
225                 230                 235                 240
Gly Leu Lys Asp Thr Glu Gly Lys Pro Val Lys Thr Ile Asp Pro
            245                 250                 255
Arg Val Gln Ser Ala Ala Ala Ala Leu Glu Gly Ser Lys Lys Asn
            260                 265                 270
Ala Ala Ile Val Ala Val Asp Pro Ala Thr Gly Asn Ile Leu Ala Ala
            275                 280                 285
Ala Asn Val Pro Ser Gly Met Asn Arg Ala Leu Glu Gly Arg Tyr Pro
            290                 295                 300
Pro Gly Ser Thr Phe Lys Val Val Thr Thr Ala Ala Leu Leu Gln Gln
305                 310                 315                 320
Gly Met Asn Pro Glu Glu Arg Ala Asp Cys Pro Lys Phe Ala His Val
            325                 330                 335
Asn Gly Gln Ser Phe Glu Asn Gln Asp Gln Phe Thr Leu Pro Ala Gly
            340                 345                 350
Ser Thr Phe Arg Asp Ser Phe Ala His Ser Cys Asn Thr Phe Phe Val
            355                 360                 365
Asn Ser Arg Ser Lys Leu Ser Glu Ser Ser Leu Lys Gln Ala Ala Glu
            370                 375                 380
Ala Phe Gly Ile Gly Gly Thr Trp Asp Val Gly Ala Ser Thr Phe Asp
385                 390                 395                 400
Gly Ser Val Pro Val Ser Asn Ser Glu Asn Asp Lys Ala Ala Ser Thr
            405                 410                 415
Ile Gly Gln Ala Arg Val Glu Ala Ser Pro Leu Val Met Ala Ser Ile
            420                 425                 430
Ala Ala Thr Val Lys Gln Gly Glu Phe Lys Gln Pro Val Leu Val Pro
            435                 440                 445
Asp Ala Val Lys Lys Pro His Gln Ala Pro Arg Met Ala Pro Gly Ile
            450                 455                 460
Val Asp Ser Leu Arg Ser Met Met Arg Ser Thr Val Thr Asp Gly Ala
465                 470                 475                 480
Gly Asp Ala Leu Arg Gly Leu Gly Gly Gln Pro His Ala Lys Thr Gly
            485                 490                 495
Thr Ala Glu Phe Gly Thr Glu Lys Pro Pro Lys Thr His Ala Trp Met
            500                 505                 510
Ile Gly Tyr Gln Gly Asp Arg Asn Ile Ala Trp Ser Val Leu Leu Glu
            515                 520                 525
Asp Gly Gly Ser Gly Gly Ala Asp Ala Gly Pro Val Ala Ala Lys Phe
            530                 535                 540
Leu Ser Asn Leu Ala Ala Gly Glx
545                 550

<210> SEQ ID NO 4
<211> LENGTH: 574
<212> TYPE: PRT
```

-continued

<213> ORGANISM: Streptomyces clavuligerus

<400> SEQUENCE: 4

```
Met Ser Arg Val Ser Thr Ala Pro Ser Gly Lys Pro Thr Ala Ala His
  1               5                  10                  15

Ala Leu Leu Ser Arg Leu Arg Asp His Gly Val Gly Lys Val Phe Gly
                 20                  25                  30

Val Val Gly Arg Glu Ala Ala Ser Ile Leu Phe Asp Glu Val Glu Gly
             35                  40                  45

Ile Asp Phe Val Leu Thr Arg His Glu Phe Thr Ala Gly Val Ala Ala
 50                  55                  60

Asp Val Leu Ala Arg Ile Thr Gly Arg Pro Gln Ala Cys Trp Ala Thr
 65                  70                  75                  80

Leu Gly Pro Gly Met Thr Asn Leu Ser Thr Gly Ile Ala Thr Ser Val
                 85                  90                  95

Leu Asp Arg Ser Pro Val Ile Ala Leu Ala Ala Gln Ser Glu Ser His
                100                 105                 110

Asp Ile Phe Pro Asn Asp Thr His Gln Cys Leu Asp Ser Val Ala Ile
                115                 120                 125

Val Ala Pro Met Ser Lys Tyr Ala Val Glu Leu Gln Arg Pro His Glu
130                 135                 140

Ile Thr Asp Leu Val Asp Ser Ala Val Asn Ala Ala Met Thr Glu Pro
145                 150                 155                 160

Val Gly Pro Ser Phe Ile Ser Leu Pro Val Asp Leu Leu Gly Ser Ser
                165                 170                 175

Glu Gly Ile Asp Thr Thr Val Pro Asn Pro Ala Asn Thr Pro Ala
                180                 185                 190

Lys Pro Val Gly Val Val Ala Asp Gly Trp Gln Lys Ala Ala Asp Gln
                195                 200                 205

Ala Ala Ala Leu Leu Ala Glu Ala Lys His Pro Val Leu Val Val Gly
                210                 215                 220

Ala Ala Ala Ile Arg Ser Gly Ala Val Pro Ala Ile Arg Ala Leu Ala
225                 230                 235                 240

Glu Arg Leu Asn Ile Pro Val Ile Thr Thr Tyr Ile Ala Lys Gly Val
                245                 250                 255

Leu Pro Val Gly His Glu Leu Asn Tyr Gly Ala Val Thr Gly Tyr Met
                260                 265                 270

Asp Gly Ile Leu Asn Phe Pro Ala Leu Gln Thr Met Phe Ala Pro Val
                275                 280                 285

Asp Leu Val Leu Thr Val Gly Tyr Asp Tyr Ala Glu Asp Leu Arg Pro
290                 295                 300

Ser Met Trp Gln Lys Gly Ile Glu Lys Lys Thr Val Arg Ile Ser Pro
305                 310                 315                 320

Thr Val Asn Pro Ile Pro Arg Val Tyr Arg Pro Asp Val Asp Val Val
                325                 330                 335

Thr Asp Val Leu Ala Phe Val Glu His Phe Glu Thr Ala Thr Ala Ser
                340                 345                 350

Phe Gly Ala Lys Gln Arg His Asp Ile Glu Pro Leu Arg Ala Arg Ile
                355                 360                 365

Ala Glu Phe Leu Ala Asp Pro Glu Thr Tyr Glu Asp Gly Met Arg Val
370                 375                 380

His Gln Val Ile Asp Ser Met Asn Thr Val Met Glu Glu Ala Ala Glu
385                 390                 395                 400
```

Pro Gly Glu Gly Thr Ile Val Ser Asp Ile Gly Phe Phe Arg His Tyr
            405                 410                 415

Gly Val Leu Phe Ala Arg Ala Asp Gln Pro Phe Gly Phe Leu Thr Ser
            420                 425                 430

Ala Gly Cys Ser Ser Phe Gly Tyr Gly Ile Pro Ala Ala Ile Gly Ala
            435                 440                 445

Gln Met Ala Arg Pro Asp Gln Pro Thr Phe Leu Ile Ala Gly Asp Gly
450                 455                 460

Gly Phe His Ser Asn Ser Ser Asp Leu Glu Thr Ile Ala Arg Leu Asn
465                 470                 475                 480

Leu Pro Ile Val Thr Val Val Asn Asn Asp Thr Asn Gly Leu Ile
            485                 490                 495

Glu Leu Tyr Gln Asn Ile Gly His His Arg Ser His Asp Pro Ala Val
            500                 505                 510

Lys Phe Gly Gly Val Asp Phe Val Ala Leu Ala Glu Ala Asn Gly Val
            515                 520                 525

Asp Ala Thr Arg Ala Thr Asn Arg Glu Glu Leu Leu Ala Ala Leu Arg
530                 535                 540

Lys Gly Ala Glu Leu Gly Arg Pro Phe Leu Ile Glu Val Pro Val Asn
545                 550                 555                 560

Tyr Asp Phe Gln Pro Gly Gly Phe Gly Ala Leu Ser Ile Glx
            565                 570

<210> SEQ ID NO 5
<211> LENGTH: 514
<212> TYPE: PRT
<213> ORGANISM: Streptomyces clavuligerus

<400> SEQUENCE: 5

Met Gly Ala Pro Val Leu Pro Ala Ala Phe Gly Phe Leu Ala Ser Ala
1               5                   10                  15

Arg Thr Gly Gly Gly Arg Ala Pro Gly Pro Val Phe Ala Thr Arg Gly
            20                  25                  30

Ser His Thr Asp Ile Asp Thr Pro Gln Gly Glu Arg Ser Leu Ala Ala
        35                  40                  45

Thr Leu Val His Ala Pro Ser Val Ala Pro Asp Arg Ala Val Ala Arg
    50                  55                  60

Ser Leu Thr Gly Ala Pro Thr Thr Ala Val Leu Ala Gly Glu Ile Tyr
65                  70                  75                  80

Asn Arg Asp Glu Leu Leu Ser Val Leu Pro Ala Gly Pro Ala Pro Glu
                85                  90                  95

Gly Asp Ala Glu Leu Val Leu Arg Leu Leu Glu Arg Tyr Asp Leu His
            100                 105                 110

Ala Phe Arg Leu Val Asn Gly Arg Phe Ala Thr Val Val Arg Thr Gly
        115                 120                 125

Asp Arg Val Leu Leu Ala Thr Asp His Ala Gly Ser Val Pro Leu Tyr
    130                 135                 140

Thr Cys Val Ala Pro Gly Glu Val Arg Ala Ser Thr Glu Ala Lys Ala
145                 150                 155                 160

Leu Ala Ala His Arg Asp Pro Lys Gly Phe Pro Leu Ala Asp Ala Arg
                165                 170                 175

Arg Val Ala Gly Leu Thr Gly Val Tyr Gln Val Pro Ala Gly Ala Val
            180                 185                 190

Met Asp Ile Asp Leu Gly Ser Gly Thr Ala Val Thr His Arg Thr Trp
        195                 200                 205

```
Thr Pro Gly Leu Ser Arg Arg Ile Leu Pro Glu Gly Glu Ala Val Ala
    210                 215                 220
Ala Val Arg Ala Ala Leu Glu Lys Ala Val Ala Gln Arg Val Thr Pro
225                 230                 235                 240
Gly Asp Thr Pro Leu Val Val Leu Ser Gly Gly Ile Asp Ser Ser Gly
                245                 250                 255
Val Ala Ala Cys Ala His Arg Ala Ala Gly Glu Leu Asp Thr Val Ser
                260                 265                 270
Met Gly Thr Asp Thr Ser Asn Glu Phe Arg Gly Ala Arg Ala Val Val
                275                 280                 285
Asp His Leu Arg Thr Arg His Arg Glu Ile Thr Ile Pro Thr Thr Glu
            290                 295                 300
Leu Leu Ala Gln Leu Pro Tyr Ala Val Trp Ala Ser Glu Ser Val Asp
305                 310                 315                 320
Pro Asp Ile Ile Glu Tyr Leu Leu Pro Leu Thr Ala Leu Tyr Arg Ala
                325                 330                 335
Leu Asp Gly Pro Glu Arg Arg Ile Leu Thr Gly Tyr Gly Ala Asp Ile
                340                 345                 350
Pro Leu Gly Gly Met His Arg Glu Asp Arg Leu Pro Ala Leu Asp Thr
                355                 360                 365
Val Leu Ala His Asp Met Ala Thr Phe Asp Gly Leu Asn Glu Met Ser
            370                 375                 380
Pro Val Leu Ser Thr Leu Ala Gly His Trp Thr Thr His Pro Tyr Trp
385                 390                 395                 400
Asp Arg Glu Val Leu Asp Leu Leu Val Ser Leu Glu Ala Gly Leu Lys
                405                 410                 415
Arg Arg His Gly Arg Asp Lys Trp Val Leu Arg Ala Ala Met Ala Asp
                420                 425                 430
Ala Leu Pro Ala Glu Thr Val Asn Arg Pro Lys Leu Gly Val His Glu
            435                 440                 445
Gly Ser Gly Thr Thr Ser Ser Phe Ser Arg Leu Leu Leu Asp His Gly
450                 455                 460
Val Ala Glu Asp Arg Val His Glu Ala Lys Arg Gln Val Val Arg Glu
465                 470                 475                 480
Leu Phe Asp Leu Thr Val Gly Gly Arg His Pro Ser Glu Val Asp
                485                 490                 495
Thr Asp Asp Val Val Arg Ser Val Ala Asp Arg Thr Ala Arg Gly Ala
                500                 505                 510
Ala Glx

<210> SEQ ID NO 6
<211> LENGTH: 314
<212> TYPE: PRT
<213> ORGANISM: Streptomyces clavuligerus

<400> SEQUENCE: 6

Val Glu Arg Ile Asp Ser His Val Ser Pro Arg Tyr Ala Gln Ile Pro
 1               5                  10                  15
Thr Phe Met Arg Leu Pro His Asp Pro Gln Pro Arg Gly Tyr Asp Val
                20                  25                  30
Val Val Ile Gly Ala Pro Tyr Asp Gly Gly Thr Ser Tyr Arg Pro Gly
            35                  40                  45
Ala Arg Phe Gly Pro Gln Ala Ile Arg Ser Glu Ser Gly Leu Ile His
        50                  55                  60
```

```
Gly Val Gly Ile Asp Arg Gly Pro Gly Thr Phe Asp Leu Ile Asn Cys
 65                  70                  75                  80

Val Asp Ala Gly Asp Ile Asn Leu Thr Pro Phe Asp Met Asn Ile Ala
                 85                  90                  95

Ile Asp Thr Ala Gln Ser His Leu Ser Gly Leu Leu Lys Ala Asn Ala
                100                 105                 110

Ala Phe Leu Met Ile Gly Gly Asp His Ser Leu Thr Val Ala Ala Leu
            115                 120                 125

Arg Ala Val Ala Glu Gln His Gly Pro Leu Ala Val Val His Leu Asp
130                 135                 140

Ala His Ser Asp Thr Asn Pro Ala Phe Tyr Gly Gly Arg Tyr His His
145                 150                 155                 160

Gly Thr Pro Phe Arg His Gly Ile Asp Glu Lys Leu Ile Asp Pro Ala
                165                 170                 175

Ala Met Val Gln Ile Gly Ile Arg Gly His Asn Pro Lys Pro Asp Ser
                180                 185                 190

Leu Asp Tyr Ala Arg Gly His Gly Val Arg Val Thr Ala Asp Glu
            195                 200                 205

Phe Gly Glu Leu Gly Val Gly Thr Ala Asp Leu Ile Arg Glu Lys
210                 215                 220

Val Gly Gln Arg Pro Val Tyr Val Ser Val Asp Ile Asp Val Val Asp
225                 230                 235                 240

Pro Ala Phe Ala Pro Gly Thr Gly Thr Pro Ala Pro Gly Gly Leu Leu
                245                 250                 255

Ser Arg Glu Val Leu Ala Leu Leu Arg Cys Val Gly Asp Leu Lys Pro
                260                 265                 270

Val Gly Phe Asp Val Met Glu Val Ser Pro Leu Tyr Asp His Gly Gly
            275                 280                 285

Ile Thr Ser Ile Leu Ala Thr Glu Ile Gly Ala Glu Leu Leu Tyr Gln
            290                 295                 300

Tyr Ala Arg Ala His Arg Thr Gln Leu Glx
305                 310

<210> SEQ ID NO 7
<211> LENGTH: 326
<212> TYPE: PRT
<213> ORGANISM: Streptomyces clavuligerus

<400> SEQUENCE: 7

Met Ala Ser Pro Ile Val Asp Cys Thr Pro Tyr Arg Asp Glu Leu Leu
  1               5                  10                  15

Ala Leu Ala Ser Glu Leu Pro Glu Val Pro Arg Ala Asp Leu His Gly
                 20                  25                  30

Phe Leu Asp Glu Ala Lys Thr Leu Ala Ala Arg Leu Pro Glu Gly Leu
             35                  40                  45

Ala Ala Ala Leu Asp Thr Phe Asn Ala Val Gly Ser Glu Asp Gly Tyr
         50                  55                  60

Leu Leu Leu Arg Gly Leu Pro Val Asp Asp Ser Glu Leu Pro Glu Thr
 65                  70                  75                  80

Pro Thr Ser Thr Pro Ala Pro Leu Asp Arg Lys Arg Leu Val Met Glu
                 85                  90                  95

Ala Met Leu Ala Leu Ala Gly Arg Arg Leu Gly Leu His Thr Gly Tyr
                100                 105                 110

Gln Glu Leu Arg Ser Gly Thr Val Tyr His Asp Val Tyr Pro Ser Pro
```

```
            115                 120                 125
Gly Ala His Tyr Leu Ser Ser Glu Thr Ser Glu Thr Leu Leu Glu Phe
            130                 135                 140
His Thr Glu Met Ala Tyr His Ile Leu Gln Pro Asn Tyr Val Met Leu
145                 150                 155                 160
Ala Cys Ser Arg Ala Asp His Glu Asn Arg Ala Glu Thr Leu Val Gly
                165                 170                 175
Ser Val Arg Lys Ala Leu Pro Leu Leu Asp Glu Lys Thr Arg Ala Arg
                180                 185                 190
Leu Phe Asp Arg Lys Val Pro Cys Cys Val Asp Val Ala Phe Arg Gly
            195                 200                 205
Gly Val Asp Asp Pro Gly Ala Ile Ala Asn Val Lys Pro Leu Tyr Gly
        210                 215                 220
Asp Ala Asn Asp Pro Phe Leu Gly Tyr Asp Arg Glu Leu Leu Ala Pro
225                 230                 235                 240
Glu Asp Pro Ala Asp Lys Glu Ala Val Ala His Leu Ser Gln Ala Leu
                245                 250                 255
Asp Asp Val Thr Val Gly Val Lys Leu Val Pro Gly Asp Val Leu Ile
            260                 265                 270
Ile Asp Asn Phe Arg Thr Thr His Ala Arg Thr Pro Phe Ser Pro Arg
            275                 280                 285
Trp Asp Gly Lys Asp Arg Trp Leu His Arg Val Tyr Ile Arg Thr Asp
    290                 295                 300
Arg Asn Gly Gln Leu Ser Gly Gly Glu Arg Ala Gly Asp Thr Ile Ser
305                 310                 315                 320
Phe Ser Pro Arg Arg Glx
                325

<210> SEQ ID NO 8
<211> LENGTH: 394
<212> TYPE: PRT
<213> ORGANISM: Streptomyces clavuligerus

<400> SEQUENCE: 8

Met Ser Asp Ser Thr Pro Lys Thr Pro Arg Gly Phe Val Val His Thr
1               5                   10                  15
Ala Pro Val Gly Leu Ala Asp Asp Gly Arg Asp Asp Phe Thr Val Leu
                20                  25                  30
Ala Ser Thr Ala Pro Ala Thr Val Ser Ala Val Phe Thr Arg Ser Arg
            35                  40                  45
Phe Ala Gly Pro Ser Val Val Leu Cys Arg Glu Ala Val Ala Asp Gly
        50                  55                  60
Gln Ala Arg Gly Val Val Leu Ala Arg Asn Ala Asn Val Ala Thr
65                  70                  75                  80
Gly Leu Glu Gly Glu Glu Asn Ala Arg Glu Val Arg Glu Ala Val Ala
                85                  90                  95
Arg Ala Leu Gly Leu Pro Glu Gly Glu Met Leu Ile Ala Ser Thr Gly
            100                 105                 110
Val Ile Gly Arg Gln Tyr Pro Met Glu Ser Ile Arg Glu His Leu Lys
        115                 120                 125
Thr Leu Glu Trp Pro Ala Gly Glu Gly Gly Phe Asp Arg Ala Ala Arg
    130                 135                 140
Ala Ile Met Thr Thr Asp Thr Arg Pro Lys Glu Val Arg Val Ser Val
145                 150                 155                 160
```

```
Gly Gly Ala Thr Leu Val Gly Ile Ala Lys Gly Val Gly Met Leu Glu
                165                 170                 175

Pro Asp Met Ala Thr Leu Leu Thr Phe Phe Ala Thr Asp Ala Arg Leu
            180                 185                 190

Asp Pro Ala Glu Gln Asp Arg Leu Phe Arg Arg Val Met Asp Arg Thr
        195                 200                 205

Phe Asn Ala Val Ser Ile Asp Thr Asp Thr Ser Thr Ser Asp Thr Ala
    210                 215                 220

Val Leu Phe Ala Asn Gly Leu Ala Gly Glu Val Asp Ala Gly Glu Phe
225                 230                 235                 240

Glu Glu Ala Leu His Thr Ala Ala Leu Ala Leu Val Lys Asp Ile Ala
                245                 250                 255

Ser Asp Gly Glu Gly Ala Ala Lys Leu Ile Glu Val Gln Val Thr Gly
            260                 265                 270

Ala Arg Asp Asp Ala Gln Ala Lys Arg Val Gly Lys Thr Val Val Asn
        275                 280                 285

Ser Pro Leu Val Lys Thr Ala Val His Gly Cys Asp Pro Asn Trp Gly
    290                 295                 300

Arg Val Ala Met Ala Ile Gly Lys Cys Ser Asp Asp Thr Asp Ile Asp
305                 310                 315                 320

Gln Glu Arg Val Thr Ile Arg Phe Gly Glu Val Glu Val Tyr Pro Pro
                325                 330                 335

Lys Ala Arg Gly Asp Gln Ala Asp Asp Ala Leu Arg Ala Ala Val Ala
            340                 345                 350

Glu His Leu Arg Gly Asp Glu Val Val Ile Gly Ile Asp Leu Ala Ile
        355                 360                 365

Ala Asp Gly Ala Phe Thr Val Tyr Gly Cys Asp Leu Thr Glu Gly Tyr
    370                 375                 380

Val Arg Leu Asn Ser Glu Tyr Thr Thr Glx
385                 390

<210> SEQ ID NO 9
<211> LENGTH: 556
<212> TYPE: PRT
<213> ORGANISM: Streptomyces clavuligerus

<400> SEQUENCE: 9

Met Glu Thr Thr Arg Ser Thr Thr Ala Asp Glu Gly Phe Asp Ala Gly
1               5                   10                  15

Val Arg Gly Val Val Ala Pro Thr Asp Ala Pro Gly Gly Thr Leu Arg
            20                  25                  30

Leu Val Arg Thr Asp Asp Phe Asp Ser Leu Asp Pro Gly Asn Thr Tyr
        35                  40                  45

Tyr Ala Tyr Thr Trp Asn Phe Leu Arg Leu Ile Gly Arg Thr Leu Val
    50                  55                  60

Thr Phe Asp Thr Ala Pro Gly Lys Ala Gly Gln Arg Leu Val Pro Asp
65                  70                  75                  80

Leu Ala Glu Ser Leu Gly Glu Ser Ser Glu Asp Gly Arg Val Trp Thr
                85                  90                  95

Tyr Arg Leu Arg Glu Gly Leu Arg Tyr Glu Asp Gly Thr Pro Val Val
            100                 105                 110

Ser Ala Asp Ile Lys His Ala Ile Ala Arg Ser Asn Tyr Gly Thr Asp
        115                 120                 125

Val Leu Gly Ala Gly Pro Thr Tyr Phe Arg His Leu Leu Gly Thr Glu
    130                 135                 140
```

```
Tyr Gly Gly Pro Trp Arg Glu Pro Asp Ala Asp Gly Pro Val Thr Leu
145                 150                 155                 160

Glu Thr Pro Asp Glu Arg Thr Leu Val Phe Arg Leu Arg Glu Pro Phe
                165                 170                 175

Ala Gly Met Asp Leu Leu Ala Thr Met Pro Ser Thr Thr Pro Val Pro
            180                 185                 190

Arg Asp Arg Asp Thr Gly Ala Glu Tyr Arg Leu Arg Pro Val Ala Thr
                195                 200                 205

Gly Pro Tyr Arg Ile Val Ser Tyr Thr Arg Gly Glu Leu Ala Val Leu
        210                 215                 220

Glu Pro Asn Pro His Trp Asp Pro Glu Thr Asp Pro Val Arg Val Gln
225                 230                 235                 240

Arg Ala Ser Arg Ile Glu Val His Leu Gly Lys Asp Pro His Glu Val
                245                 250                 255

Asp Arg Met Leu Leu Ala Gly Glu Ala His Val Asp Leu Ala Gly Phe
            260                 265                 270

Gly Val Gln Pro Ala Ala Gln Glu Arg Ile Leu Ala Glu Pro Glu Leu
        275                 280                 285

Arg Ala His Ala Asp Asn Pro Leu Thr Gly Phe Thr Trp Ile Tyr Cys
290                 295                 300

Leu Ser Ser Arg Ile Ala Pro Phe Asp Asn Val His Cys Arg Arg Ala
305                 310                 315                 320

Val Gln Phe Ala Thr Asp Lys Ala Ala Met Gln Glu Ala Tyr Gly Gly
                325                 330                 335

Ala Val Gly Gly Asp Ile Ala Thr Thr Leu Leu Pro Pro Thr Leu Asp
            340                 345                 350

Gly Tyr Lys His Phe Asp Arg Tyr Pro Val Gly Pro Glu Gly Thr Gly
        355                 360                 365

Asp Leu Glu Ala Ala Arg Ala Glu Leu Lys Leu Ala Gly Met Pro Asp
        370                 375                 380

Gly Phe Arg Thr Arg Ile Ala Ala Arg Lys Asp Arg Leu Lys Glu Tyr
385                 390                 395                 400

Arg Ala Ala Glu Ala Leu Ala Ala Gly Leu Ala Arg Val Gly Ile Glu
                405                 410                 415

Ala Glu Val Leu Asp Phe Pro Ser Gly Asp Tyr Phe Asp Arg Tyr Gly
            420                 425                 430

Gly Cys Pro Glu Tyr Leu Arg Glu His Gly Ile Gly Ile Ile Met Phe
        435                 440                 445

Gly Trp Gly Ala Asp Phe Pro Asp Gly Tyr Gly Phe Leu Gln Gln Ile
    450                 455                 460

Thr Asp Gly Arg Ala Ile Lys Glu Arg Gly Asn Gln Asn Met Gly Glu
465                 470                 475                 480

Leu Asp Asp Pro Glu Ile Asn Ala Leu Leu Asp Glu Gly Ala Gln Cys
                485                 490                 495

Ala Asp Pro Ala Arg Arg Ala Glu Ile Trp His Arg Ile Asp Gln Leu
            500                 505                 510

Thr Met Asp His Ala Val Ile Val Pro Tyr Leu Tyr Pro Arg Ser Leu
        515                 520                 525

Leu Tyr Arg His Pro Asp Thr Arg Asn Ala Phe Val Thr Gly Ser Phe
        530                 535                 540

Gly Met Tyr Asp Tyr Val Ala Leu Gly Ala Lys Glx
545                 550                 555
```

-continued

```
<210> SEQ ID NO 10
<211> LENGTH: 433
<212> TYPE: PRT
<213> ORGANISM: Streptomyces clavuligerus

<400> SEQUENCE: 10

Met Glu Val Ala Arg Arg Thr Gly Val Arg His Gly Thr Val Glu Arg
 1               5                  10                  15

Arg Leu Asp Arg Leu Asp Arg Ile Val Gly Leu Pro Leu Thr Leu Arg
                20                  25                  30

Ser Arg His Thr Ala Arg Leu Thr Thr Ala Gly Ser Arg Ile Leu Val
            35                  40                  45

Ala Gly Arg Arg Phe Phe His Gln Val Asp Leu Ala Ala Arg Thr His
        50                  55                  60

Ile Phe Gly His Gly Ser Glu Ala Val Asp Ala Pro Glu Val Leu Ser
 65                  70                  75                  80

Leu Val Ser Thr Glu Pro Leu Leu Asp Glu Val Val Glu Asp Ala Ala
                85                  90                  95

Ala Ser Leu Asp Leu Leu Leu Ser Val Arg His Glu Ala Pro His Gln
            100                 105                 110

Val Ala Ala Gln Leu Ala Gly Tyr Gln Val Asp Ala Ala Tyr Thr Trp
        115                 120                 125

Ser Leu Gln Ser Pro Arg His Ser Leu Glu Arg Ser Val Arg Thr Cys
    130                 135                 140

Glu Val Leu Asp Asp Pro Leu Trp Val Ile Leu Pro Arg Asp His Pro
145                 150                 155                 160

Leu Ala Ala Arg Arg Glu Val Ser Leu Ala Asp Leu Arg Asp Glu Thr
                165                 170                 175

Trp Val Ser Glu Thr Gly Pro Gly Ser Glu Ile Leu Val Thr Arg Val
            180                 185                 190

Phe Gln Leu Ala Gly Leu Thr Ala Pro Thr Arg Leu His Ile Thr Gly
        195                 200                 205

Ala Ser Val Ala Arg Gly Ile Leu Arg Arg Gly Asp Ala Ile Gly Leu
    210                 215                 220

Gly Ser Pro Thr His Pro Ala Val Gln Asp Pro Ser Leu Val Arg Arg
225                 230                 235                 240

Ser Leu Ala Glu Arg Pro Arg Arg Thr Thr Ser Leu Leu Val Asp Pro
                245                 250                 255

Thr Ile Val Pro Arg Ala Leu Ala Gly Arg Leu Ala Leu Leu Ile Ala
            260                 265                 270

Glu Val Gln Leu Arg Arg Phe Ala Glu His His Arg Asp Leu Leu Asp
        275                 280                 285

Glu Pro Trp Trp Ala Gln Trp Tyr Ala Glu Arg Thr Gly Ala Asp Ala
    290                 295                 300

Arg Arg Phe Gly Ala Gly Pro Asp Gln Gly Ser Val Pro Gly Gln Ala
305                 310                 315                 320

Glu Gly Arg Lys Leu Asp Val Asp Asp Leu His Leu Leu Gln Ala Val
                325                 330                 335

Ala Arg His Gly Ser Ile Asn Arg Ala Ala Val Leu Ser Ile Ser
            340                 345                 350

Gln Ser Ala Leu Thr Arg Arg Ile His Arg Leu Glu Gln Ser Leu Gly
        355                 360                 365

Ala Arg Leu Leu Leu Arg Ser Pro Arg Gly Thr Ser Leu Thr Gly Pro
    370                 375                 380
```

Thr Arg Gln Phe Leu Arg Gln Leu Ala Leu Tyr Glu Ala Glu Phe Arg
385                 390                 395                 400

Glu Ala Ala Leu Ala Cys Arg Ser Val Glu Arg Pro Leu Ala Gln Gly
            405                 410                 415

His Trp Pro Ile Arg Arg Gly Val Ala Ala Gly Ala Arg Met Ser Gly
            420                 425                 430

Glx

<210> SEQ ID NO 11
<211> LENGTH: 248
<212> TYPE: PRT
<213> ORGANISM: Streptomyces clavuligerus

<400> SEQUENCE: 11

Met Pro Ser Ala Leu Gln Gly Lys Val Ala Leu Ile Thr Gly Ala Ser
1               5                   10                  15

Ser Gly Ile Gly Glu Ala Thr Ala Arg Ala Leu Ala Ala Glu Gly Ala
            20                  25                  30

Ala Val Ala Ile Ala Ala Arg Arg Val Glu Lys Leu Arg Ala Leu Gly
        35                  40                  45

Asp Glu Leu Thr Ala Ala Gly Ala Lys Val His Val Leu Glu Leu Asp
    50                  55                  60

Val Ala Asp Arg Gln Gly Val Asp Ala Ala Val Ala Ser Thr Val Glu
65                  70                  75                  80

Ala Leu Gly Gly Leu Asp Ile Leu Val Asn Asn Ala Gly Ile Met Leu
                85                  90                  95

Leu Gly Pro Val Glu Asp Ala Asp Thr Thr Asp Trp Thr Arg Met Ile
            100                 105                 110

Asp Thr Asn Leu Leu Gly Leu Met Tyr Met Thr Arg Ala Ala Leu Pro
        115                 120                 125

His Leu Leu Arg Ser Lys Gly Thr Val Val Gln Met Ser Ser Ile Ala
    130                 135                 140

Gly Arg Val Asn Val Arg Asn Ala Ala Val Tyr Gln Ala Thr Lys Phe
145                 150                 155                 160

Gly Val Asn Ala Phe Ser Glu Thr Leu Arg Gln Glu Val Thr Glu Arg
                165                 170                 175

Gly Val Arg Val Val Ile Glu Pro Gly Thr Thr Asp Thr Glu Leu
            180                 185                 190

Arg Gly His Ile Thr His Thr Ala Thr Lys Glu Met Tyr Glu Gln Arg
        195                 200                 205

Ile Ser Gln Ile Arg Lys Leu Gln Ala Gln Asp Ile Ala Glu Ala Val
    210                 215                 220

Arg Tyr Ala Val Thr Ala Pro His His Ala Thr Val His Glu Ile Phe
225                 230                 235                 240

Ile Arg Pro Thr Asp Gln Val Glx
                245

<210> SEQ ID NO 12
<211> LENGTH: 409
<212> TYPE: PRT
<213> ORGANISM: Streptomyces clavuligerus

<400> SEQUENCE: 12

Met Met Asn Glu Ala Ala Pro Gln Ser Asp Gln Val Ala Pro Ala Tyr
1               5                   10                  15

```
Pro Met His Arg Val Cys Pro Val Asp Pro Pro Gln Leu Ala Gly
         20                  25                  30

Leu Arg Ser Gln Lys Ala Ala Ser Arg Val Thr Leu Trp Asp Gly Ser
             35                  40                  45

Gln Val Trp Leu Val Thr Ser His Ala Gly Ala Arg Ala Val Leu Gly
 50                      55                  60

Asp Arg Arg Phe Thr Ala Val Thr Ser Ala Pro Gly Phe Pro Met Leu
 65                  70                  75                  80

Thr Arg Thr Ser Gln Leu Val Arg Ala Asn Pro Glu Ser Ala Ser Phe
                 85                  90                  95

Ile Arg Met Asp Asp Pro Gln His Ser Arg Leu Arg Ser Met Leu Thr
                100                 105                 110

Arg Asp Phe Leu Ala Arg Arg Ala Glu Ala Leu Arg Pro Ala Val Arg
            115                 120                 125

Glu Leu Leu Asp Glu Ile Leu Gly Gly Leu Val Lys Gly Glu Arg Pro
        130                 135                 140

Val Asp Leu Val Ala Gly Leu Thr Ile Pro Val Pro Ser Arg Val Ile
145                 150                 155                 160

Thr Leu Leu Phe Gly Ala Gly Asp Asp Arg Arg Glu Phe Ile Glu Asp
                165                 170                 175

Arg Ser Ala Val Leu Ile Asp Arg Gly Tyr Thr Pro Glu Gln Val Ala
                180                 185                 190

Lys Ala Arg Asp Glu Leu Asp Gly Tyr Leu Arg Glu Leu Val Glu Glu
            195                 200                 205

Arg Ile Glu Asn Pro Gly Thr Asp Leu Ile Ser Arg Leu Val Ile Asp
        210                 215                 220

Gln Val Arg Pro Gly His Leu Arg Val Glu Glu Met Val Pro Met Cys
225                 230                 235                 240

Arg Leu Leu Leu Val Ala Gly His Gly Thr Thr Thr Ser Gln Ala Ser
                245                 250                 255

Leu Ser Leu Leu Ser Leu Leu Thr Asp Pro Glu Leu Ala Gly Arg Leu
                260                 265                 270

Thr Glu Asp Pro Ala Leu Leu Pro Lys Ala Val Glu Glu Leu Leu Arg
            275                 280                 285

Phe His Ser Ile Val Gln Asn Gly Leu Ala Arg Ala Ala Val Glu Asp
        290                 295                 300

Val Gln Leu Asp Asp Val Leu Ile Arg Ala Gly Glu Gly Val Val Leu
305                 310                 315                 320

Ser Leu Ser Ala Gly Asn Arg Asp Glu Thr Val Phe Pro Asp Pro Asp
                325                 330                 335

Arg Val Asp Val Asp Arg Asp Ala Arg Arg His Leu Ala Phe Gly His
                340                 345                 350

Gly Met His Gln Cys Leu Gly Gln Trp Leu Ala Arg Val Glu Leu Glu
            355                 360                 365

Glu Ile Leu Ala Ala Val Leu Arg Trp Met Pro Gly Ala Arg Leu Ala
        370                 375                 380

Val Pro Phe Glu Glu Leu Asp Phe Arg His Glu Val Ser Ser Tyr Gly
385                 390                 395                 400

Leu Gly Ala Leu Pro Val Thr Trp Glx
                405

<210> SEQ ID NO 13
<211> LENGTH: 11604
<212> TYPE: DNA
```

<213> ORGANISM: Streptomyces clavuligerus

<400> SEQUENCE: 13

```
gaattcgagt catcgggttc ggcgacggat gggcggttcg gccacgcacc gtcactcttc      60
gtcccctctt cacaagaact cccgatacgt ggagaagaga gcgtgaagag cgcgtccggt     120
cagggttgcc gagaaccgtc caccatgacg gagcctggta ctgacggagt cgggagaccg     180
ctcatgtccc gtgtatcgac cgcccccagc ggcaagccta ccgccgctca cgccctcctg     240
tcacggttgc gtgatcacgg tgtggggaag gtgtttgggg ttgtcggccg agaggccgcg     300
tcgattctct tcgacgaggt cgaccccatc gacttcgttc tgacccgcca cgagttcacc     360
gcgggtgtcg ccgctgatgt cctcgcgcgg atcaccggtc gccccaggc gtgctgggcc      420
accctgggcc ccggtatgac caacctctcc accggtatcg ccacgtccgt cctggaccgc     480
tcgccggtca tcgcgctcgc cgcgcagtcg gagtcgcacg acatcttccc gaacgacacc     540
caccagtgcc tggactcggt ggcgatcgtc gccccgatgt ccttgtacgc cgtggagctc     600
cagcggcccc acgagatcac cgacctcgtc gactccgccg tgaacgcggc catgaccgag     660
ccggtcgggc cctccttcat ctccctcccg gtggacctgc tcggctcctc cgagggcatc     720
gacaccaccg tccccaaccc gccggcgaac acccggcga aaccggtcgg cgtcgtcgcc      780
gacggctgga gaaggccgc cgaccaggcc gccgccctgc tcgccgaggc caagcacccg      840
gtgctcgtcg tcggagcggc cgcgatccgc tcgggcgccg tcccggcgat ccgcgccctg     900
gccgagcgcc tgaacatccc ggtcatcacg acctacatcg ccaagggtgt cctgccggtc     960
ggccacgagc tgaactacgg cgccgtcacc ggctacatgg acggcatcct caacttcccg    1020
gcgctccaga ccatgttcgc cccggtggac ctcgtcctca ccgtcggcta cgactacgcc    1080
gaggacctgc gcccgtccat gtggcagaag ggcatcgaga agaagaccgt ccgtatctcc    1140
ccgacggtca acccgatccc ccgggtctac cggcccgacg tcgacgtcgt caccgacgtc    1200
ctcgccttcg tggagcactt cgagaccgcg accgcctcct tcgggccaa gcagcgccac     1260
gacatcgagc gctgcgcgc ccggatcgcg gagttcctgg ccgacccgga gacctacgag     1320
gacggcatgc gcgtccacca ggtcatcgac tccatgaaca ccgtcatgga ggaggccgcc    1380
gagcccggcg agggcacgat cgtctccgac atcggcttct tccgtcacta cggtgtgctc    1440
ttcgcccgcg ccgaccagcc cttcggcttc ctcacctcgg cgggctgctc cagcttcggc    1500
tacggcatcc ccgccgccat cggcgcccag atggcccgcc cggaccagcc gaccttcctc    1560
atcgcgggtg acggcggctt ccactccaac agctccgacc tggagaccat cgcccggctc    1620
aacctgccga tcgtgaccgt cgtcgtcaac aacgacacca acggcctgat cgagctgtac    1680
cagaacatcg gtcaccaccg cagccacgac ccggcggtca agttcggcgg cgtcgacttc    1740
gtcgcgctcg ccgaggccaa cggtgtcgac gccaccgcg ccaccaaccg cgaggagctg     1800
ctcgcggccc tgcgcaaggg tgccgagctg gtcgtccgt tcctcatcga ggtcccggtc     1860
aactacgact ccagccgggg cggcttcggc gccctgagca tctgatcatg ggggcaccgg    1920
ttcttccggc tgccttcggg ttcctggcct ccgcccgaac gggcgggggc cgggcccccg    1980
gcccggtctt cgcgacccgg ggcagccaca ccgacatcga cacgcccag ggggagcgct     2040
cgctcgcggc gaccctggtg cacgccccct cggtcgcgcc cgaccgcgcg gtggcgcgct    2100
ccctcaccgg cgcgcccacc accgcggtgc tcgccggtga gatctacaac cgggacgaac    2160
tcctctccgt gctgccgcc ggaccgcgc cggagggga cgcggagctg gtcctgcggc       2220
tgctggaacg ctatgacctg catgccttcc ggctggtgaa cgggcgcttc gcgaccgtgg    2280
```

```
tgcggaccgg ggaccgggtc ctgctcgcca ccgaccacgc cggttcggtg ccgctgtaca      2340
cctgtgtggc gccgggcgag gtccgggcgt ccaccgaggc caaggcgctc gccgcgcacc      2400
gcgacccgaa gggcttcccg ctcgcggacg cccgccgggt cgccggtctg accggtgtct      2460
accaggtgcc cgcgggcgcc gtgatggaca tcgacctcgg ctcgggcacc gccgtcaccc      2520
accgcacctg gaccccgggc ctctcccgcc gcatcctgcc ggagggcgag gccgtcgcgg      2580
ccgtgcgggc cgcgctggag aaggccgtcg cccagcgggt caccccggc gacacccgt       2640 tggtggtgct ctccggcgga atcgactcct ccggggtcgc ggcctgtgcg caccgggcgg      2700
ccggggaact ggacacggtg tccatgggca ccgacacgtc caacgagttc cgcgaggccc      2760
gggcggtcgt cgaccatctg cgcacccggc accgggagat caccatcccg accaccgagc      2820
tgctggcgca gctcccgtac gcggtgtggg cctccgagtc ggtggacccg gacatcatcg      2880
agtacctgct cccctgaca cgcgctctacc gggcgctcga cgggccggag cgccgcatcc      2940
tcaccgggta cggcgcggac atcccctcg ggggcatgca ccgcgaggac cggctgcccg       3000
cgctggacac cgttctcgcg cacgacatgg ccaccttcga cgggctgaac gagatgtccc      3060
cggtgctgtc cacgctggcg gggcactgga ccacccaccc gtactgggac cgggaggtcc      3120
tcgatctgct ggtctcgctg gaggccgggc tcaagcggcg gcacgccgg gacaagtggg       3180 tgctgcgcgc cgcgatggcc gacgccctcc cggcggagac cgtcaaccgg cccaagctgg      3240
gcgtccacga gggctcgggc accacgtcct cgttctcccg gctgctgctg gaccacggtg      3300
tcgccgagga ccgcgtccac gaggcgaagc ggcaggtggt gcgcgagctg ttcgatctca      3360
cggtcggggg cggacggcac ccctccgagg tggacaccga cgatgtggtg cgctccgtgg      3420
ccgaccggac cgcgcggggg gcggcctagt cccgccacgg ggagcccgcc ggacgccgga      3480
cccgcgcggg accggtaccc ggggccgccc gcggactccg gcgcaccggc accctgtcc       3540 cccacccgtt gacgaccgtc ggccctcggc cctcgcggcc cctgacgacc gtcgcccgat      3600
tcccaggagg gagctgaaag cgtggagcgc atcgactcgc acgtttcacc ccgctacgca      3660
cagatcccca ccttcatgcg cctgccgcac gatccccagc cccgcggcta tgacgtggtg      3720
gtcatcggag cccctacga cggggggcacc agctaccgtc ccggcgcccg gttcggcccc      3780
caggccatcc gcagtgagtc gggcctcatc cacggtgtcg gcatcgaccg gggccccggc      3840
acgttcgacc tgatcaactg tgtcgacgcc ggggacatca atctgacgcc gttcgacatg      3900
aacatcgcga tcgacacggc gcagagccat ctgtcgggcc tgctgaaggc caacgccgcc      3960
tttctgatga tcggcggcga ccactcgctg acggtggccg ccctgcgcgc ggtcgcggag      4020
cagcacggcc cgctcgccgt ggtgcacctg gacgcgcact ccgacaccaa cccggccttc      4080
tacgggggcc ggtaccacca cggcaccccc ttccggcacg ggatcgacga gaagctgatc      4140
gacccggcgg cgatggtcca gatcggcatc cggggccaca acccgaagcc ggactcgctc      4200
gactacgccc ggggccacgg cgtccgggtg gtcacggcgg acgagttcgg cgagctgggg      4260
gtgggcggga ccgccgacct catccgcgag aaggtcggcc agcggcccgt gtacgtctcg      4320
gtcgacatcg acgtggtcga ccccgccttc gccccggta cgggcacgcc cgcgccgggc       4380
gggctcctct cgcgcgaggt gctggcgctg ctgcgctgcg tgggtgacct gaagccggtc      4440
ggcttcgacg tgatggaggt gtcaccccctc tacgaccacg gcgggatcac ttcgatcctg      4500
gccacggaga tcggtgcgga actgctctac cagtacgccc gagcccacag aacccagttg      4560
tgaaggagac atcgtgtcat ggcctctccg atagttgact gcacccgta ccgcgacgag       4620
```

-continued

```
ctgctcgcgc tcgcctccga gcttcccgag gtgccgcgcg cggacctcca tggcttcctc    4680
gacgaggcga agacgctggc cgcccgtctc ccggaggggc tggccgccgc tctcgacacc    4740
ttcaacgccg tgggcagcga ggacggttat ctgctgctgc gcgggctgcc cgtcgacgac    4800
agcgagctgc ccgagacgcc gacctccacc ccggccccgc tggaccgcaa gcggctggtg    4860
atggaggcca tgctcgcgct ggccggccgc cggctcggtc tgcacacggg gtaccaggag    4920
ctgcgctcgg gcacggtcta ccacgacgtg tacccgtcgc ccggcgcgca ctacctgtcc    4980
tcggagacct ccgagacgct gctggagttc cacacggaga tggcgtacca catcctccag    5040
ccgaactacg tcatgctggc ctgctcccgc gcggaccacg agaacgggc ggagacgctg    5100 gtcggctcgg tccgcaaggc gctgcccctg ctggacgaga agacccgggc ccgtctcttc    5160
gaccgcaagg tgccctgctg cgtggacgtg gccttccgcg gcggggtcga cgacccgggc    5220
gcgatcgcca acgtcaagcc gctctacggg gacgcgaacg acccgttcct cgggtacgac    5280
cgcgagctgc tggcgccgga ggaccccgcg gacaaggagg ccgtcgccca tctgtcccag    5340
gcgctcgacg atgtgaccgt cggggtgaag ctcgtcccg tgacgtcct catcatcgac    5400 aacttccgca ccacgcacgc gcggacgccg ttctcgcccc gctgggacgg gaaggaccgc    5460
tggctgcacc gcgtctacat ccgcaccgac cgcaatggac agctctccgg cggcgagcgc    5520
gcgggcgaca ccatctcgtt ctcgccgcgc cgctgagccc ggctccccga ggccctgggc    5580
cccggcgccg gaaccggctc ccggtcctgc ccctcaccc gccgcgcggg tgaggggca    5640 ggcccctttg tgccgggtgc cgtgcgtcct gcgagggtgc cggggcgggg gggacggcgg    5700
aggtgcccgg cggccgggtg ccgtgcgccg cccgtgggtg ctgtacagca ctccgtgtgc    5760
cgtgcgccac cccgtgcata aatttgccac tctatgggaa ataatgcaga gtgcgacggg    5820
tgaggccgtc gccgtgccct ttccgtgaca ggagacgctg acatgtccga cagcacaccg    5880
aagacgcccc ggggattcgt ggtgcacacg gcgccggtgg gcctggccga cgacggccgc    5940
cacgacttca ccgtcctcgc ctccaccgcc ccggccaccg tgagcgccgt cttcacccgc    6000
tcccgcttcg ccgggccgag cgtcgtgctg tgccggagg cggtgccga cgggcaggcg    6060 cgcggtgtgg tggtgctggc ccgcaacgcg aatgtcgcga ccggcctgga gggcgaggag    6120
aacgcgcgcg aggtgcgcga ggccgtcgcc cgggccctcg gctgccggga gggcgagatg    6180
ctgatcgcct ccaccggggt gatcggccgg cagtacccga tggagagcat ccgggagcac    6240
ctcaagacgc tggagtggcc cgccggggag ggcggcttcg accgcgcggc ccgcgccatc    6300
atgacgaccg acacccggcc caaggaggtc cgggtcagcg tcggcggggc gaccctcgtg    6360
ggcatcgcca agggcgtcgg catgctggag cccgacatgg cgacgctgct gaccttcttc    6420
gccacggacg cccggctgga cccggccgag caggaccgcc tcttccgccg ggtcatggac    6480
cgcaccttca cgcggtcag catcgacacc gacacctcca ccagcgacac ggcggtgctg    6540
ttcgccaacg gcctggcggg cgaggtcgac gccggggagt tcgaggaggc gctgcacacg    6600
gcggcgctgg ccctggtcaa ggacatcgcg agcgacggcg agggcgcggc caagctgatc    6660
gaggtccagg tcaccggcgc ccgcgacgac gcccaggcca gcgggtcgg caagaccgtc    6720 gtcaactccc cgttggtgaa gaccgccgtg cacggctgcg accccaactg gggccgggtc    6780
gccatggcga tcggcaagtg ctcggacgac accgacatcg accaggagcg ggtgacgatc    6840
cgcttcggcg aggtcgaggt ctatccgccg aaggcccggg gcgaccaggc cgacgacgcg    6900
ctgcgggccg ccgtcgcgga gcatctgcgg ggcgacgagg tggtcatcgg gatcgacctc    6960
gccatcgcgg acggggcctt caccgtctac ggctgcgacc tcaccgaggg ctatgtccgg    7020
```

```
ctgaactcgg agtacaccac ctgatccccg gacagggaac gggccgccgc cccgttccct   7080
gtccgctccc gtcccgtgtg gttataccga ccgttccccg gctatgcgca cgggacggag   7140
cggcccccgc cgggccccgc ccggccgcac gatgaggggc gatgcaaggt gacgagggca   7200
ggagggacat ggagaccact cggtcgacga ccgcggacga gggcttcgac gccggggtac   7260
ggggagtggt cgcgccgacc gacgccccgg gcgggacgct gcggctggtc cgcacggacg   7320
acttcgactc gctcgacccc ggcaacacgt actacgccta cacctggaac ttcctccggc   7380
tcatcggccg gacgctggtc accttcgaca ccgcgccggg caaggcgggc cagcggctcg   7440
tgcccgacct cgccgagtcg ctgggcgagt cctccgagga cggccgggtc tggacctacc   7500
ggctgcgcga gggcctgcgc tacgaggacg gcacgccggt cgtctcggcc gacatcaagc   7560
acgccatcgc ccgcagcaac tacggcaccg atgtcctggg cgccggtccg acctacttcc   7620
gccacctcct gggcaccgag tacggcggcc cctggcggga gccggacgcc gacggaccgg   7680
tgacgctgga gaccccggac gagcggacgc tggtcttccg gctgcgggag ccgttcgcgg   7740
ggatggatct gctggcgacc atgccgtcca ccacccccgt gccgcgcgac cgggacaccg   7800
gcgccgagta ccggctgcgg cccgtggcga ccggcccgta ccggatcgtc tcgtacaccc   7860
ggggcgagct ggccgtcctg gagcccaatc cgcactggga ccccgagacc gacccggtgc   7920
gcgtccagcg cgcctcccgg atcgaggtgc acctcggcaa ggacccgcac gaggtggacc   7980
gcatgctgct ggcgggcgag gcccatgtgg acctcgcggc cttcggtgtg cagcccgcgg   8040
cccaggagcg catcctcgcc gagccggagc tgcgcgcgca cgcggacaac ccgctgaccg   8100
gcttcacctg gatctactgc ctgtcgagcc ggatcgcccc gttcgacaat gtgcactgcc   8160
ggcgggccgt gcagttcgcc accgacaaag cggccatgca ggaggcgtac ggcggcgcgg   8220
tgggcggcga catcgcgacc accctgctgc ccccgaccct cgacggctac aagcacttcg   8280
accgctaccc ggtcggcccc gagggcaccg gcgacctgga ggccgcccgc gccgagctga   8340
agctggccgg gatgcccgac ggcttccgca ccaggatcgc cgcccgcaag gaccggctca   8400
aggagtaccg ggccgccgag gcgctggccg ccgggctcgc ccgggtcggc atcgaggcgg   8460
aggtgctgga cttcccgtcg ggcgactact tcgaccgcta cggcggctgc ccggagtatc   8520
tgcgcgagca cgggatcggg atcatcatgt tcggctgggg cgccgacttc cccgacggat   8580
acggcttcct ccagcagatc accgacgggc gcgcgatcaa ggagcgcggc aaccagaaca   8640
tgggcgagct ggacgacccg gagatcaacg cgctgctgga cgaggggcg cagtgcgccg   8700 acccggcgcg gcgcgcggag atctggcacc gcatcgacca gctcacgatg gaccacgcgg   8760
tcatcgttcc gtatctgtac ccgcggtccc tgctctaccg gcacccggac acccgcaacg   8820
ccttcgtcac cggctccttc gggatgtacg actacgtggc gctcggcgcg aagtgagcac   8880
ggggtccggc cccgggaccg tatgtcccgg ggccggaccc cgcccgttcc ccgcccggtc   8940
cggtccggac ccgtcgcgg cccgctcagc cggacatccg ggccccggcc gcgacccccgc   9000 gccggatcgc ccagtggccc tgcgccaggg gccgttccac gctgcggcag gcgagagcgg   9060
cctcgcggaa ctccgcctcg tacagcgcga gctggcgcag gaactgccgg gtcgggccgg   9120
tcaggctggt ccccgcgggg ctgcgcagca gcagccgggc gccgagggac tgctccagcc   9180
ggtgaatccg gcgggtgagc gccgactggc tgatcgacag caccgccgcg gcccggttga   9240
tgctgccgtg ccgggccacg gcctggagca gatggagatc gtccacatcc agtttgcggc   9300
cctcggcctg gccgggcacg gagccctggt cgggtcccgc cccgaagcgg cggcgtccg   9360
```

-continued

| | | | | |
|---|---|---|---|---|
| cgccggtgcg | ctccgcgtac | cactgcgccc | accagggctc | gtccagcagg tcgcggtggt | 9420 |
| gttcggcgaa | gcgccggagc | tggacctcgg | cgatcagcgc | ggccagccgt cccgccagcg | 9480 |
| cccggggcac | gatggtgggg | tcgacgagca | gactcgtggt | gcggcgcggg cgctccgcca | 9540 |
| gggagcggcg | caccagcgag | gggtcctgca | ccgccgggtg | ggtgggcgag ccgagaccta | 9600 |
| tcgcgtcccc | gcggcgcagg | atgccccggg | caaccgatgc | ccccgtgatg tggagccggg | 9660 |
| tgggcgcggt | gagcccggcc | agctggaaga | cacgtgtcac | caggatctcc gagccgggtc | 9720 |
| ccgtctcgga | cacccaggtc | tcgtcccgca | gatcggcgag | cgagacctcc cgccgggcgg | 9780 |
| ccagcggatg | gtcccggggc | aggatcaccc | acagcgggtc | gtccagcacc tcacaggtgc | 9840 |
| gcacggaccg | ctccaggctg | tgccgggggg | actggaggct | ccaggtgtag gccgcgtcca | 9900 |
| cctggtagcc | cgccagttgg | gcggcgacct | ggtgcggggc | ctcgtgccgg accgacagca | 9960 |
| gcaggtccag | cgaggccgcc | gcgtcctcca | ccacctcgtc | gagcagggt tccgtggaga | 10020 |
| ccagcgacag | cacctccggg | gcgtccacgg | cctcggagcc | atggccgaag atatgcgtcc | 10080 |
| gcgcggccag | gtcgacctgg | tggaagaacc | gccgcccggc | gacgaggatg cgggagcccg | 10140 |
| cggtggtcag | ccggggccgtg | tggcggctgc | gcagggtcag | cgggaggccg acgatccggt | 10200 |
| ccagccggtc | gagtctgcgc | tccacggtgc | cgtgccggac | acccgtccgc cgggccactt | 10260 |
| ccatgaggtc | tccgcagtgt | cccaccgcgt | ccagtaaaga | cagatcgcat cggctgacac | 10320 |
| cagcagacgt | cggttctgac | ccagagacaa | tgtcggttc | ccttttccgt caaggactgt | 10380 |
| accgctgaat | tgtccgaagt | ggctcttgaa | ttgcttcgga | atcgatccta ggcagcgccg | 10440 |
| ctcttcggat | tctcctcgcc | gggaagcgga | acgcgcccgg | ccggatggcg ggcgcgctcc | 10500 |
| gggcgccgtc | ccgggaacgg | gggacggggc | acggcacggc | cggccacccg gtccgggcgc | 10560 |
| gcggcgtgga | cctggtcggc | ggacggggtgt | cagacctggt | cggtggggcg tatgaagatc | 10620 |
| tcgtggacgt | tcgcgtggtg | cggcgcggtc | acggcgtagc | ggaccgcctc cgcgatgtcc | 10680 |
| tgggcctgga | gcttgcggat | ctggctgatc | cgctgctcgt | acatctcctt ggtggcggtg | 10740 |
| tgggtgatgt | ggccgcgcag | ctccgtgtcg | gtggtgcccg | gctcgatgac gacgacccgc | 10800 |
| acccgcgct | cggtgacctc | ctggcgcagc | gtctcgctga | acgcgttcac accgaacttc | 10860 |
| gtggcctggt | agacggccgc | gttgcggacg | ttcaccccggc | ccgcgatcga ggacatctgc | 10920 |
| accacggtgc | ccttgctgcg | cagcagatgg | ggaagggccg | cccgggtcat gtacatcagg | 10980 |
| cccaggagat | tggtgtcgat | catccgggtc | cagtcggtgg | tgtcggcgtc ctccaccggg | 11040 |
| ccgagcagca | tgatcccggc | gttgttgacg | aggatgtcga | ggccgcccag cgcctcgacg | 11100 |
| gtggaggcga | cggcggcgtc | cacccctgc | cggtcggcga | cgtcgagttc gaggacatgg | 11160 |
| accttcgccc | cggcggcggt | cagctcgtca | cccagggcgc | gcagcttctc gacccggcgc | 11220 |
| gcggcgatgg | ccacggcggc | gccctcggcg | gccagggcgc | gggccgtggc ctcgccgatg | 11280 |
| cccgagctcg | cgccgtgat | gagcgcgact | ttcccctgga | gtgcggatgg catcatttcc | 11340 |
| tccacatggt | gctgcgatcg | tgtgagcgt | atgaagaagg | ggtgagacct gccgtgccgg | 11400 |
| ggcgggttcc | gtacgccgga | ccgttgcggt | gggcacggcc | gaccgggtac ggatggccgc | 11460 |
| agttccccgg | ggagttcccg | gggaatggtg | aataccgcgg | cgctctccga tggtcttcgg | 11520 |
| aggacacccg | gggattcacc | gggaatcagc | ggccggagtt | ctccccgtcc acggcagacg | 11580 |
| ctatcagcgt | cgcattcccc | ggtg | | | 11604 |

<210> SEQ ID NO 14
<211> LENGTH: 1656

<212> TYPE: DNA
<213> ORGANISM: Streptomyces clavuligerus

<400> SEQUENCE: 14

```
tcagccggcc gcgaggttgc tgaggaactt cgcggcgacg gggcccgcgt cggcgccgcc    60
cgacccgccg tcctccagca ggaccgacca ggcgatgttc cggtcgccct ggtagccgat   120
catccaggcg tgcgtcttcg gcggcttctc ggtgccgaac tcggcggtac cggtcttggc   180
gtgcggctgt ccgccgaggc cccgcagggc gtcgccggcg ccgtcggtga cggtcgaacg   240
catcatggaa cgcagcgagt cgacgatgcc cggggccatc cggggggcct ggtgcggctt   300
cttgaccgcg tcgggcacca gcacgggctg cttgaactcg ccctgcttga cggtggcggc   360
gatggaggcc atcaccaggg gcgacgcctc gaccctggcc tgtccgatgg tggacgcggc   420
cttgtcgttc tcgctgttgg agacggggac gctgccgtcg aaggtggagg cgccgacgtc   480
ccaggtgccg ccgatgccga aggcttcggc ggcctgcttc aggctggact cggagagctt   540
gctgcgggag ttgacgaaga acgtgttgca ggagtgggcg aagctgtccc ggaaggtcga   600
gcccgcgggc agcgtgaact ggtcctggtt ctcgaagctc tggccgttga catgggcgaa   660
cttcgggcag tcggcccgct cctccgggtt catcccctgc tggagcaggg ccgcggtggt   720
gaccaccttg aaggtggagc cggcgggta gcggccctcc agcgcgcggt tcatgccgga   780
gggcacgttc gcggcggcca ggatgttgcc ggtggcgggg tcgacggcga cgatcgccgc   840
gttcttcttc gagccctcca gggccgccgc ggcggcggac tggacccgcg ggtcgatggt   900
ggtcttcacc ggcttgccct cggtgtcctt gaggccggtg agcttcttga ccacctggcc   960
ggactcacgg tccaggatca cgaccgagcg cgccgcgccg gagccgccgg tgagctgctt  1020
gtcgtagcgg gactggaggc cgccgagcc cttgccggtc ctgggtcga ccgcgccgat  1080
gatggaggcg gcctggagga cattgccgtt ggcgtcgagg atgtccgcgc gctcccgcga  1140
cttgagggcg agggtctgcc ccggaaccat ctgcggatgg atcatctcgg tgttgaacgc  1200
gaccttccac tccttgccgc cgccgacgac cttcgcggtg gagtcccagg cgtactcccc  1260
ggccccgggg aggtcattc tgacggtgaa cggtatctcc acctcgccct cggggttctt  1320
ctccccggtc ttggcggtga tctccgtctt cgtcggcttg aggttggtca tgacggattt  1380
gatcagcgac tcggcgttgt ccggggtgtc cgtcagcccg gcggccgtcg ggcgtcgcc  1440
cttctcccag cgccgagga aggtgtcgaa ctgtccggcc ccgcctcca cctcggggtc  1500
gcccgaatcc ttctcgtcgg caaccaggct ggtgtaaccc caatagccga gccccaccgt  1560
cacggccagc ccggcgacca ccgcggtggc cgcccggcca cgggagcggc gcctgccctg  1620
cggcgggtca tcgccatagt tgtcggaatg cgtcat                            1656
```

<210> SEQ ID NO 15
<211> LENGTH: 1722
<212> TYPE: DNA
<213> ORGANISM: Streptomyces clavuligerus

<400> SEQUENCE: 15

```
atgtcccgtg tatcgaccgc ccccagcggc aagcctaccg ccgctcacgc cctcctgtca    60
cggttgcgtg atcacggtgt ggggaaggtg tttgggggttg tcggccgaga ggccgcgtcg   120
attctcttcg acgaggtcga ggggatcgac ttcgttctga cccgccacga gttcaccgcg   180
ggtgtcgccc ctgatgtcct cgcgcggatc accggtcgcc cccaggcgtg ctgggccacc   240
ctgggccccg gtatgaccaa cctctccacc ggtatcgcca cgtccgtcct ggaccgctcg   300
```

| | |
|---|---|
| ccggtcatcg cgctcgccgc gcagtcggag tcgcacgaca tcttcccgaa cgacacccac | 360 |
| cagtgcctgg actcggtggc gatcgtcgcc ccgatgtcca agtacgccgt ggagctccag | 420 |
| cggccccacg agatcaccga cctcgtcgac tccgccgtga acgcggccat gaccgagccg | 480 |
| gtcgggccct ccttcatctc cctcccggtg gacctgctcg gctcctccga gggcatcgac | 540 |
| accaccgtcc ccaacccgcc ggcgaacacc cggcgaaac cggtcggcgt cgtcgccgac | 600 |
| ggctggcaga aggccgccga ccaggccgcc gccctgctcg ccgaggccaa gcacccggtg | 660 |
| ctcgtcgtcg gagcggccgc gatccgctcg ggcgccgtcc cggcgatccg cgccctggcc | 720 |
| gagcgcctga acatcccggt catcacgacc tacatcgcca agggtgtcct gccggtcggc | 780 |
| cacgagctga actacggcgc cgtcaccggc tacatggacg gcatcctcaa cttcccggcg | 840 |
| ctccagacca tgttcgcccc ggtggacctc gtcctcaccg tcggctacga ctacgccgag | 900 |
| gacctgcgcc cgtccatgtg gcagaagggc atcgagaaga agaccgtccg tatctccccg | 960 |
| acggtcaacc cgatcccccg ggtctaccgg cccgacgtcg acgtcgtcac cgacgtcctc | 1020 |
| gccttcgtgg agcacttcga gaccgcgacc gcctccttcg gggccaagca gcgccacgac | 1080 |
| atcgagccgc tgcgcgcccg gatcgcggag ttcctggcca cccggagac ctacgaggac | 1140 |
| ggcatgcgcg tccaccaggt catcgactcc atgaacaccg tcatggagga ggccgccgag | 1200 |
| cccggcgagg gcacgatcgt ctccgacatc ggcttcttcc gtcactacgg tgtgctcttc | 1260 |
| gcccgcgccg accagccctt cggcttcctc acctcggcgg gctgctccag cttcggctac | 1320 |
| ggcatccccg ccgccatcgg cgcccagatg gcccgcccgg accagccgac cttcctcatc | 1380 |
| gcgggtgacg gcggcttcca ctccaacagc tccgacctgg agaccatcgc ccggctcaac | 1440 |
| ctgccgatcg tgaccgtcgt cgtcaacaac gacaccaacg gcctgatcga gctgtaccag | 1500 |
| aacatcggtc accaccgcag ccacgacccg gcggtcaagt tcggcggcgt cgacttcgtc | 1560 |
| gcgctcgccg aggccaacgg tgtcgacgcc cccgcgccca ccaacgcgca ggagctgctc | 1620 |
| gcggccctgc gcaagggtgc cgagctgggt cgtccgttcc tcatcgaggt cccggtcaac | 1680 |
| tacgacttcc agccgggcgg cttcggcgcc ctgagcatct ga | 1722 |

<210> SEQ ID NO 16
<211> LENGTH: 1542
<212> TYPE: DNA
<213> ORGANISM: Streptomyces clavuligerus

<400> SEQUENCE: 16

| | |
|---|---|
| atgggggcac cggttcttcc ggctgccttc gggttcctgg cctccgcccg aacgggcggg | 60 |
| ggccgggccc ccgcccggt cttcgcgacc cggggcagcc acaccgacat cgacacgccc | 120 |
| caggggagc gctcgctcgc ggcgaccctg gtgcacgccc cctcggtcgc gcccgaccgc | 180 |
| gcggtggcg gctccctcac cggcgcgccc accaccgcgg tgctcgccgg tgagatctac | 240 |
| aaccgggacg aactcctctc cgtgctgccc gccggacccg cgccggaggg ggacgcggag | 300 |
| ctggtcctgc ggctgctgga acgctatgac ctgcatgcct tccggctggt gaacgggcgc | 360 |
| ttcgcgaccg tggtgcggac cggggaccgg gtcctgctcg ccaccgacca cgccggttcg | 420 |
| gtgccgctgt acacctgtgt ggcgccgggc gaggtccggg cgtccaccga ggccaaggcg | 480 |
| ctcgccgcgc accgcgaccc gaagggcttc ccgctcgcgg acgcccgccg ggtcgccggt | 540 |
| ctgaccggtg tctaccaggt gcccgcgggc gccgtgatgg acatcgacct cggctcgggc | 600 |
| accgccgtca cccaccgcac ctggaccccg ggcctctccc gccgcatcct gccggagggc | 660 |
| gaggccgtcg cggccgtgcg ggccgcgctg gagaaggccg tcgcccagcg ggtcacccc | 720 |

```
ggcgacaccc cgttggtggt gctctccggc ggaatcgact cctccggggt cgcggcctgt    780
gcgcaccggg cggccgggga actggacacg gtgtccatgg caccgacac gtccaacgag     840 ttccgcgagg cccgggcggt cgtcgaccat ctgcgcaccc ggcaccggga gatcaccatc    900
ccgaccaccg agctgctggc gcagctcccg tacgcggtgt gggcctccga gtcggtggac    960
ccggacatca tcgagtacct gctcccctg acagcgctct accgggcgct cgacgggccg    1020
gagcgccgca tcctcaccgg gtacggcgcg gacatccccc tcggggcat gcaccgcgag    1080 gaccggctgc ccgcgctgga caccgttctc gcgcacgaca tggccacctt cgacgggctg    1140
aacgagatgt ccccggtgct gtccacgctg gcggggcact ggaccaccca cccgtactgg    1200
gaccgggagg tcctcgatct gctggtctcg ctggaggccg ggctcaagcg gcggcacggc    1260
cgggacaagt gggtgctgcg cgccgcgatg gccgacgccc tccggcgga gaccgtcaac    1320 cggcccaagc tggcgtcca cgagggctcg ggcaccacg cctcgttctc ccggctgctg    1380
ctggaccacg tgtcgccga ggaccgcgtc cacgaggcga agcggcaggt ggtgcgcgag    1440
ctgttcgatc tcacggtcgg gggcggacgg caccctccg aggtggacac cgacgatgtg    1500
gtgcgctccg tggccgaccg gaccgcgcgg ggggcggcct ag                      1542
```

<210> SEQ ID NO 17
<211> LENGTH: 942
<212> TYPE: DNA
<213> ORGANISM: Streptomyces clavuligerus

<400> SEQUENCE: 17

```
gtggagcgca tcgactcgca cgtttcaccc cgctacgcac agatccccac cttcatgcgc     60
ctgccgcacg atccccagcc ccgcggctat gacgtggtgg tcatcggagc ccctacgac    120 gggggcacca gctaccgtcc cggcgcccgg ttcggcccc aggccatccg cagtgagtcg    180
ggcctcatcc acggtgtcgg catcgaccgg ggccccggca cgttcgacct gatcaactgt    240
gtcgacgccg gggacatcaa tctgacgccg ttcgacatga acatcgcgat cgacacggcg    300
cagagccatc tgtcgggcct gctgaaggcc aacgccgcct ttctgatgat cggcggcgac    360
cactcgctga cggtggccgc cctgcgcgcg gtcgcggagc agcacggccc gctcgccgtg    420
gtgcacctgg acgcgcactc cgacaccaac ccggccttct acggggccg gtaccaccac    480 ggcacccct tccggcacgg gatcgacgag aagctgatcg acccggcggc gatggtccag    540
atcggcatcc ggggccacaa cccgaagccg gactcgctcg actacgcccg ggccacggc    600 gtccgggtgg tcacggcgga cgagttcggc gagctggggg tggcgggac cgccgacctc    660 atccgcgaga aggtcggcca gcggcccgtg tacgtctcgg tcgacatcga cgtggtcgac    720
cccgccttcg cccccggtac gggcacgccc gcgccgggcg ggctcctctc gcgcgaggtg    780
ctggcgctgc tgcgctgcgt gggtgacctg aagccggtcg gcttcgacgt gatggaggtg    840
tcacccctct acgaccacgg cgggatcact tcgatcctgg ccacggagat cggtgcggaa    900
ctgctctacc agtacgcccg agcccacaga acccagttgt ga                      942
```

<210> SEQ ID NO 18
<211> LENGTH: 978
<212> TYPE: DNA
<213> ORGANISM: Streptomyces clavuligerus

<400> SEQUENCE: 18

```
atggcctctc cgatagttga ctgcaccccg taccgcgacg agctgctcgc gctcgcctcc     60
```

-continued

```
gagcttcccg aggtgccgcg cgcggacctc catggcttcc tcgacgaggc gaagacgctg      120
gccgcccgtc tcccggaggg gctggccgcc gctctcgaca ccttcaacgc cgtgggcagc      180
gaggacggtt atctgctgct gcgcgggctg ccgtcgacg acagcgagct gcccgagacg       240
ccgacctcca ccccggcccc gctggaccgc aagcggctgg tgatggaggc catgctcgcg      300
ctggccggcc gccggctcgg tctgcacacg gggtaccagg agctgcgctc gggcacggtc      360
taccacgacg tgtacccgtc gcccggcgcg cactacctgt cctcggagac ctccgagacg      420
ctgctggagt tccacacgga gatggcgtac cacatcctcc agccgaacta cgtcatgctg      480
gcctgctccc gcgcggacca cgagaaccgg gcggagacgc tggtcggctc ggtccgcaag      540
gcgctgcccc tgctggacga gaagacccgg gcccgtctct tcgaccgcaa ggtgccctgc      600
tgcgtggacg tggccttccg cggcggggtc gacgacccgg gcgcgatcgc caacgtcaag      660
ccgctctacg gggacgcgaa cgacccgttc tcgggtacg accgcgagct gctggcgccg       720
gaggaccccg cggacaagga ggccgtcgcc catctgtccc aggcgctcga cgatgtgacc      780 gtcgggtga agctcgtccc cggtgacgtc ctcatcatcg acaacttccg caccacgcac      840
gcgcggacgc cgttctcgcc ccgctgggac gggaaggacc gctggctgca ccgcgtctac      900
atccgcaccg accgcaatgg acagctctcc ggcggcgagc gcgcgggcga caccatctcg      960
ttctcgccgc gccgctga                                                   978
```

<210> SEQ ID NO 19
<211> LENGTH: 1182
<212> TYPE: DNA
<213> ORGANISM: Streptomyces clavuligerus

<400> SEQUENCE: 19

```
atgtccgaca gcacaccgaa gacgccccgg ggattcgtgg tgcacacggc gccggtgggc       60
ctggccgacg acgccgcga cgacttcacc gtcctcgcct ccaccgcccc ggccaccgtg      120
agcgccgtct tcacccgctc ccgcttcgcc gggccgagcg tcgtgctgtg ccgggaggcg      180
gtggccgacg ggcaggcgcg cggtgtggtg gtgctggccc gcaacgcgaa tgtcgcgacc      240
ggcctggagg gcgaggagaa cgcgcgcgag gtgcgcgagg ccgtcgcccg gccctcggg      300 ctgccggagg gcgagatgct gatcgcctcc accggggtga tcggccggca gtacccgatg      360
gagagcatcc gggagcacct caagacgctg gagtggcccg ccggggaggg cggcttcgac      420
cgcgcggccc gcgccatcat gacgaccgac acccggccca aggaggtccg ggtcagcgtc      480
ggcggggcga ccctcgtggg catcgccaag ggcgtcggca tgctggagcc cgacatggcg      540
acgctgctga ccttcttcgc cacggacgcc cggctgaccc cggccgagca ggaccgcctc      600
ttccgccggg tcatggaccg caccttcaac gcggtcagca tcgacaccga cacctccacc      660
agcgacacgg cggtgctgtt cgccaacggc ctggcgggcg aggtcgacgc cggggagttc      720
gaggaggcgc tgcacacggc ggcgctggcc ctggtcaagg acatcgcgag cgacggcgag      780
ggcgcggcca agctgatcga ggtccaggtc accggcgccc gcgacgacgc ccaggccaag      840
cgggtcggca agaccgtcgt caactccccg ttggtgaaga ccgccgtgca cggctgcgac      900
cccaactggg gccgggtcgc catggcgatc ggcaagtgct cggacgacac cgacatcgac      960
caggagcggg tgacgatccg cttcggcgag gtcgaggtct atccgccgaa ggcccggggc     1020
gaccaggccg acgacgcgct gcgggccgcc gtcgcggagc atctgcgggg cgacgaggtg     1080
gtcatcggga tcgacctcgc catcgcggac ggggccttca ccgtctacgg ctgcgacctc     1140
accgagggct atgtccggct gaactcggag tacaccacct ga                       1182
```

<210> SEQ ID NO 20
<211> LENGTH: 1668
<212> TYPE: DNA
<213> ORGANISM: Streptomyces clavuligerus

<400> SEQUENCE: 20

```
atggagacca ctcggtcgac gaccgcggac gagggcttcg acgccggggt acggggagtg      60
gtcgcgccga ccgacgcccc gggcgggacg ctgcggctgg tccgcacgga cgacttcgac     120
tcgctcgacc ccggcaacac gtactacgcc tacacctgga acttcctccg gctcatcggc     180
cggacgctgg tcaccttcga caccgcgccg ggcaaggcgg ccagcggct cgtgcccgac      240
ctcgccgagt cgctgggcga gtcctccgag gacggccggg tctggaccta ccggctgcgc     300
gagggcctgc gctacgagga cggcacgccg gtcgtctcgg ccgacatcaa gcacgccatc     360
gcccgcagca actacggcac cgatgtcctg gcgccggtc cgacctactt ccgccacctc      420
ctgggcaccg agtacggcgg ccctggcgg gagccggacg ccgacggacc ggtgacgctg      480
gagaccccgg acgagcggac gctggtcttc cggctgcggg agccgttcgc ggggatggat     540
ctgctggcga ccatgccgtc caccaccccc gtgccgcgcg accgggacac cggcgccgag     600
taccggctgc ggcccgtggc gaccggcccg taccggatcg tctcgtacac ccggggcgag     660
ctggccgtcc tggagcccaa tccgcactgg gaccccgaga ccgacccggt gcgcgtccag     720
cgcgcctccc ggatcgaggt gcacctcggc aaggacccgc acgaggtgga ccgcatgctg     780
ctggcgggcg aggcccatgt ggacctcgcg ggcttcggtg tgcagcccgc ggcccaggag     840
cgcatcctcg ccgagccgga gctgcgcgcg cacgcggaca cccgctgac cggcttcacc      900
tggatctact gcctgtcgag ccggatcgcc ccgttcgaca atgtgcactg ccggcgggcc     960
gtgcagttcg ccaccgacaa agcggccatg caggaggcgt acggcggcgc ggtgggcggc    1020
gacatcgcga ccaccctgct gcccccgacc ctcgacggct acaagcactt cgaccgctac    1080
ccggtcggcc ccgagggcac cggcgacctg gaggccgccc gcgccgagct gaagctggcc    1140
gggatgcccg acggcttccg caccaggatc gccgcccgca aggaccggct caaggagtac    1200
cggggccgccg aggcgctggc cgccgggctc gcccgggtcg gcatcgaggc ggaggtgctg    1260
gacttcccgt cgggcgacta cttcgaccgc tacgcggct gcccggagta tctgcgcgag     1320
cacgggatcg ggatcatcat gttcggctgg ggcgccgact tccccgacgg atacggcttc    1380
ctccagcaga tcaccgacgg gcgcgcgatc aaggagcgcg gcaaccagaa catgggcgag    1440
ctggacgacc cggagatcaa cgcgctgctg gacgaggggg cgcagtgcgc cgacccggcg    1500
cggcgcgcgg agatctggca ccgcatcgac cagctcacga tggaccacgc ggtcatcgtt    1560
ccgtatctgt acccgcggtc cctgctctac cggcacccgg acaccgcaa cgccttcgtc    1620
accggctcct tcgggatgta cgactacgtg gcgctcggcg cgaagtga                  1668
```

<210> SEQ ID NO 21
<211> LENGTH: 1299
<212> TYPE: DNA
<213> ORGANISM: Streptomyces clavuligerus

<400> SEQUENCE: 21

```
tcagccggac atccgggccc cggccgcgac cccgcgccgg atcggccagt ggccctgcgc      60
cagggccgt tccacgctgc ggcaggcgag agcggcctcg cggaactccg cctcgtacag     120
cgcgagctgg cgcaggaact gccgggtcgg gccggtcagg ctggtccccc gcgggctgcg     180
```

-continued

```
cagcagcagc cgggcgccga gggactgctc cagccggtga atccggcggg tgagcgccga      240
ctggctgatc gacagcaccg ccgcggcccg gttgatgctg ccgtgccggg ccacggcctg      300
gagcagatgg agatcgtcca catccagttt gcggccctcg gcctggccgg gcacggagcc      360
ctggtcgggt cccgccccga agcggcgggc gtccgcgccg gtgcgctccg cgtaccactg      420
cgcccaccag ggctcgtcca gcaggtcgcg gtggtgttcg gcgaagcgcc ggagctggac      480
ctcggcgatc agcgcggcca gccgtcccgc cagcgcccgg ggcacgatgg tggggtcgac      540
gagcagactc gtggtgcggc gcgggcgctc cgccagggag cggcgcacca gcgaggggtc      600
ctgcaccgcc gggtgggtgg gcgagccgag acctatcgcg tccccgcggc gcaggatgcc      660
ccgggcaacc gatgccccg tgatgtggag ccgggtgggc gcggtgagcc cggccagctg      720
gaagacacgt gtcaccagga tctccgagcc gggtcccgtc tcggacaccc aggtctcgtc      780
ccgcagatcg gcgagcgaga cctcccgccg ggcggccagc ggatggtccc ggggcaggat      840
cacccacagc gggtcgtcca gcacctcaca ggtgcgcacg gaccgctcca ggctgtgccg      900
gggggactgg aggctccagg tgtaggccgc gtccacctgg tagcccgcca gttgggcggc      960
gacctggtgc ggggcctcgt gccggaccga cagcagcagg tccagcgagg ccgccgcgtc     1020
ctccaccacc tcgtcgagca ggggttccgt ggagaccagc gacagcacct ccggggcgtc     1080
cacggcctcg gagccatggc cgaagatatg cgtccgcgcg gccaggtcga cctggtggaa     1140
gaaccgccgc ccggcgacga ggatgcggga gcccgcggtg gtcagccggg ccgtgtggcg     1200
gctgcgcagg gtcagcggga ggccgacgat ccggtccagc cggtcgagtc tgcgctccac     1260
ggtgccgtgc cggacacccg tccgccgggc cacttccat                            1299
```

<210> SEQ ID NO 22
<211> LENGTH: 744
<212> TYPE: DNA
<213> ORGANISM: Streptomyces clavuligerus

<400> SEQUENCE: 22

```
tcagacctgg tcgtgggggc gtatgaagat ctcgtggacg gtcgcgtggt gcggcgcggt       60
cacggcgtag cggaccgcct ccgcgatgtc ctgggcctgg agcttgcgga tctggctgat      120
ccgctgctcg tacatctcct tggtggcggt gtggtgatg tggccgcgca gctccgtgtc      180
ggtggtgccc ggctcgatga cgacgacccg caccccgcgc tcggtgacct cctggcgcag      240
cgtctcgctc aacgcgttca caccgaactt cgtggcctgg tagacggccg cgttgcggac      300
gttcacccgg cccgcgatcg aggacatctg caccacggtg cccttgctgc gcagcagatg      360
gggaagggcc gccggggtca tgtacatcag gcccaggaga ttggtgtcga tcatccgggt      420
ccagtcggtg gtgtcggcgt cctccaccgg gccgagcagc atgatcccgg cgttgttgac      480
gaggatgtcg aggccgccca gcgcctcgac ggtggaggcg acggcggcgt ccaccccctg      540
ccggtcggcg acgtcgagtt cgaggacatg gaccttcgcc ccggcggcgg tcagctcgtc      600 acccaggggcg cgcagcttct cgacccggcg cgcggcgatg ccacggcgg cgccctcggc      660 ggccagggcg cgggccgtgg cctcgccgat gcccgagctc gcgcccgtga tgagcgcgac      720
tttcccctgg agtgcggatg gcat                                             744
```

<210> SEQ ID NO 23
<211> LENGTH: 1227
<212> TYPE: DNA
<213> ORGANISM: Streptomyces clavuligerus

<400> SEQUENCE: 23

```
atgatgaacg aggcagcgcc tcagtccgac caggtggcac cggcgtatcc gatgcaccgg      60
gtctgcccgg tcgacccgcc gccgcaactg gccgggctgc ggtcccagaa ggccgcgagc     120
cgggtgacgc tgtgggacgg cagccaggtg tggctggtga cctcgcacgc cggggcccgg     180
gccgtcctgg gcgaccgccg cttcaccgcg gtgacgagcg cgcccggctt cccgatgctg     240
acccgcacct cccaactggt gcgcgccaac ccggagtcgg cgtcgttcat ccgcatggac     300
gacccgcagc actcccggct gcgctcgatg ctcacccggg acttcctggc ccgccgcgcc     360
gaggcgctgc gccccgcggt gcgggagctg ctggacgaga tcctgggcgg gctggtgaag     420
ggggagcggc cggtcgacct ggtcgccgga ctgacgatcc cggtgccctc gcgggtcatc     480
accctgctct tcggcgccgg tgacgaccgc cgggagttca tcgaggaccg cagcgcggtc     540
ctcatcgacc gcggctacac cccggagcag gtcgccaagg cccgggacga actcgacggc     600
tatctgcggg agctggtcga ggagcggatc gagaacccgg gcaccgacct gatcagccgg     660
ctcgtcatcg accaggtgcg gccggggcat ctgcgggtcg aggagatggt cccgatgtgc     720
cggctgctgc tggtggccgg tcacggcacc accaccagcc aggcgagcct gagcctgctc     780
agcctgctca ccgacccgga gctggccggg cgcctcaccg aggacccggc cctgctgccc     840
aaggcggtcg aggagctgct gcgcttccac tccatcgtgc agaacgggct ggccgtgcc      900 gcggtggagg acgtccagct cgacgatgtg ctcatccggg cgggcgaggg cgtggtgctg     960
tcgctgtcgg cgggcaaccg ggacgagacg gtcttccccg acccggaccg ggtggacgtg    1020
gaccgcgacg cccgccgcca tctcgccttc ggccacggca tgcaccagtg cctgggccag    1080
tggctggccc gggtggagct ggaggagatc ctcgccgcgg tgctgcgctg gatgcccggt    1140
gcccggctcg cggtgcccct cgaggagctg gacttccgtc atgaggtgtc cagttacggc    1200
ctcggcgccc tcccggtgac ctggtga                                       1227

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence:PRIMER

<400> SEQUENCE: 24
taygcncara thccnacntt yatg                                            24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence:PRIMER

<400> SEQUENCE: 25
tacgcscaga tcccsacstt catg                                            24
```